US007585941B2

(12) United States Patent
Pasternak et al.

(10) Patent No.: US 7,585,941 B2
(45) Date of Patent: Sep. 8, 2009

(54) MU OPIOID RECEPTOR SPLICE VARIANT POLYPEPTIDES, POLYNUCLEOTIDES AND METHODS OF SCREENING COMPOSITIONS

(75) Inventors: Gavril W. Pasternak, New York, NY (US); Ying-Xian Pan, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/588,679

(22) PCT Filed: Feb. 11, 2005

(86) PCT No.: PCT/US2005/004548

§ 371 (c)(1),
(2), (4) Date: May 29, 2007

(87) PCT Pub. No.: WO2005/079343

PCT Pub. Date: Sep. 1, 2005

(65) Prior Publication Data

US 2007/0258988 A1    Nov. 8, 2007

Related U.S. Application Data

(60) Provisional application No. 60/544,534, filed on Feb. 13, 2004.

(51) Int. Cl.
| | |
|---|---|
| *C07K 1/00* | (2006.01) |
| *C07K 14/00* | (2006.01) |
| *C07K 17/00* | (2006.01) |
| *C07H 21/04* | (2006.01) |
| *G01N 33/53* | (2006.01) |
| *G01N 33/567* | (2006.01) |

(52) U.S. Cl. ...................... 530/350; 536/23.5; 435/7.1; 435/7.2; 435/7.21

(58) Field of Classification Search ........................ None
See application file for complete search history.

(56) References Cited

U.S. PATENT DOCUMENTS

| | | | |
|---|---|---|---|
| 4,949,778 | A | 8/1990 | Ladner et al. |
| 6,103,492 | A | 8/2000 | Yu |
| 6,500,927 | B2 | 12/2002 | Pasternak et al. |
| 7,087,714 | B2 | 8/2006 | Pasternak et al. |

OTHER PUBLICATIONS

Rossi et al. "Antisense mapping the MOR-1 opioid receptor: evidence for alternative splicing and a novel morphine-6 beta-glucuronide receptor." FEBS Lett. 369 (2-3): 192-196 (1995).
Kaufman et al. "Characterization of the Murine μ Opioid Receptor Gene." the Hournal of Biological Chemistry 270(26): 15877-15883 (1995).
Abbadie et al. "Neurons in the dorsal column white matter of the spinal cord: Complex neuropil in an unexpected location." Proc. Natl. Acad. Sci. USA 96: 260-265 (1999).
Bare et al. "Expression of two variants of the human μ opioid receptor mRNA in SK-N-SH cells and human brain." FEBS Letters 354: 213-26 (1994).
Chen et al. "Molecular Cloning and Functional Expression of a μ-Opioid Receptor from Rat Brain," Molecular Pharmacology 44: 8-12 (1993).
Cole et al. "The EBV-Hybridoma Technique and its Application to Human Lung Cancer." Monoclonal Antibodies and Cancer Therapy 77-96 (1985).
Cote et al. "Generation of human monoclonal antibodies reactive with cellular antigens." Proc. Natl. Acad. Sci. USA 80; 2026-2030 (1983).
Delfs et al. "Expression of Mu Opioid Receptor mRNA in Rat Brain: An In Situ Hybridization Study at the Single Cell Level." The Journal of Comparative Neurology 345: 46-68 (1994).
Elliott et al. "The NMDA receptor antagonists, LY274614 and MK-801, and the nitric oxide synthase inhibitor, NG-nitro-L-arginine, attenuate analgesic tolerance to the mu-opioid morphine but not to kappa opioids." Pain 56; 69-75 (1994).
Evans et al. "Establishment in culture of pluripotential cells from mouse embryos." Nature 28 (1981).
Giros et al. "Chromosomal Localization of the Opioid Peptide and Receptor Genes in the Mouse." Life Sciences 56(18); 369-375 (1995).
Guiramandi et al. "Alternative Splicing of the Dopamine D2 Receptor Directs Specificity of Coupling to G-proteins." The Journal of Biological Chemistry 270(13); 7354-7358 (1995).
Huse et al. "Generation of a Large Combinatorial Library of the Immunoglobulin Repertoire in Phage Lambda." Science 246: 1275-1281 (1989).
Kolesnikov et al. "1-Aminocyclopropane Carboxylic Acid (ACPC) Prevents Mu and Delta opioid Tolerance." Life Sciences 55(18): 1393-1398 (1994).
Kolesnikov et al. "Blockade of tolerance to morphine but not to κ opioids by a nitric oxide synthase inhibitor." Proc. Natl. Acad. Sci. USA 90: 5162-5166 (1993).
Liang et al. "Cloning and characterization of the promoter region of the mouse μ opioid receptor gene." Brain Research 679: 82-88 (1995).
Lowry et al. "Protein Measurement with the Folin Phenol Reagent." J. Biol. Chem 193: 265-275 (1951).
Lucas et al. "New players in the 5-HT receptor field: genes and knockouts." TIPS 16: 246-252 (1995).
Lutz et al. "Opioid Receptors and their Pharmacological Profiles." Journal of Receptor Research 12(3): 267-286 (1992).

(Continued)

*Primary Examiner*—Robert Landsman
(74) *Attorney, Agent, or Firm*—Edwards Angell Palmer & Dodge LLP; Peter C. Lauro, Esq.; Melissa Hunter-Ensor, Esq.

(57) ABSTRACT

The present invention encompasses novel splice variant forms of the mu-opioid receptor-1 (MOR-1) and the polynucleotide sequences encoding the MOR-1 splice variants. The invention further encompasses methods of screening for compositions regulating the MOR-1 splice variant activities and the development of therapeutic modalities directed to regulating activity. Regulation of the MOR-1 splice variant activities may impact the physiologic process of analgesia.

19 Claims, 26 Drawing Sheets

OTHER PUBLICATIONS

Min et al. "Genomic structure and analysis of promoter sequence of a mouse μ opioid receptor gene." Proc. Acad. Sci. USA 91: 9081-9085 (1994).

Morrison et al. "Chimeric human antibody molecules: Mouse antigen-binding domains with human constant region domains." Proc. Natl. Acad. Sci. USA 81: 6851-6855 (1984).

Neuberger et al. "Recombinant antibodies possessing novel effector functions." Nature 312(13): 604-608 (1984).

Olson et al. "Endogenous Opiates: 1988." Peptides 10: 1253-1280 (1989).

Pan et al. "Cloning, Expression and Classification of a Kappa3-Related Opioid Receptor Using Antisense Oligodeoxynucleotides." Regul Pept. 54: 217-218 (1994).

Pan et al. "Dissociation of affinity and efficacy in KOR-3 chimeras." FEBS Letters 395: 207-210 (1996).

Pasternak et al. "Pharmacological Mechanisms of Opioid Analgesics." Clinical Neuropharmacology 16(1): 1-18 (1993).

Pasternak et al. "Mapping of opioid receptors using antisense oligodeoxynucleotides: correlating their molecular biology and pharmacology." TIPS 16: 344-350 (1995).

Reisine et al. "Molecular biology of opioid receptors." Trends Neurosci. 16: 506-510 (1996).

Reisine et al. "Opioid Analgesics and Antagonists." in Goodman & Gilman's the Pharmacology Basis of Therapeutics 9th Ed. McGraw-Hill: 521-555 (1996).

Robertson "Using Embryonic Stem Cells to Introduce Mutations into the Mouse Germ line." Biology of Reproduction 44: 238-245 (1991).

Rossi et al. "Antisense mapping of MOR-1 in Rats: Distinguishing between Morphine and Morphine-6β-glucuronide Antinociception[1]." The Journal of Pharmacology and Experimental Therapeutics 28(1): 109-114 (1997).

Rossi et al. "Naloxone sensitive orphanin FQ-induced analgesia in mice." European Journal of Pharmacology 311: R7-R8 (1996).

Rossi et al. Antisense mapping the MOR-1 opioid receptor: evidence for alternative splicing and a novel morphine 6β-glucuronide receptor. FEBS Letters 369: 192-196 (1995).

Sibinga et al. "Opioid Peptides and Opioid Receptors in Cells of the Immune System." Ann Rev. Immunol. 6: 219-249 (1988).

Simon et al. "Opioid Receptors and Endogenous Opioid Peptides." Medicinal Research Reviews 11(4) 357-374 (1991).

Standifer et al. "G Proteins and Opioid Receptor-Mediated Signalling." Cell Signal 9: 237-248 (1997).

Standifer et al. "Differential Blockade of Opioid Analgesia by Antisense Oligodeoxynucleotides Directed against Carious G Protein α Subunits." Molecular Pharmacology 50: 293-298 (1996).

Takeda et al. "Construction of chimaeric processed immunoglobulin genes containing mouse variable and human constant region sequences." Nature 314: 452-454 (1985).

Trujillo et al. "Inhibition of Morphine Tolerance and Dependence by the NMDA Receptor Antagonist MK-801." Science 251: 85-87 (1991).

Van Den Engh et al. "Estimating Genomic Distance from DNA Sequence Location in Cell Nuclei by a Random Walk Model." Science 257: 1410-1412 (1992).

Vanetti et al. "Cloning and Expression of a novel mouse somatostatin receptor (SSTR2B)." FEBS Letters 311(3): 290-294 (1992).

Wang et al. "μ opiate receptor: cDNA cloning expression." Neurobiology 90: 10230-10234 (1993).

Wolozin et al. "Classification of multiple morphine and enkephalin binding sites in the central nervous system." Proc. Natl. Acad. Sci. USA 78: 6181-6185 (1981).

Yasuda et al. "Cloning and functional comparison of κ and δ opioid receptors from mouse brain." Proc. Natl. Acad. Sci USA 90: 6736-6740 (1993).

Zimprich et al. "Cloning and expression of an isoform of the rat μ opioid receptor (rMOR 1B) which differs in agonist induced desensitization from rMOR1." FEBS Letters 359: 142-146 (1995)..

Du et al. "Identification of a novel splice variant of the mouse mu opioid receptor." Society for Neuroscience 695.5 (1996).

Du et al. "A splice variant of the mu opioid receptor is present in human SHSY-5Y cells." Society for Neuroscience 479.3 (1997).

Leventhal et al. "Antisense Mapping of the MOR-1 Opioid Receptor Clone: Modulation of Hyperphagia Induced by DAMGO[1]." The Journal of Pharmacology and Experimental Therapeutics. 282(3): 1402-1407 (1997).

Leventhal et al. "Antisense oligodeoxynucleotides against the MOR-1 clone alter weight and ingestive responses in rats." Brain Research 719: 78-84 (1996).

*Endocrinology: An Integrated Approach*, Nussey, S.S. and Whitehead, S.A. London: Taylor & Francis; c2001; http://www.ncbi.nlm.nih.gov/sites/entrez?db=books&doptcmdl=TOCView&term=hormone+assay+AND+endocrin%5Bbook%5D.

GeneReviews, Pagon, Roberta A., Editor-in-chief; Bird, Thomas C.; Dolan, Cynthia R.; Smith Richard J.H.; Stephens, Karen; Associate editors. Seattle (WA): University of Washington ; c1993, entitled *PROP1-Related Combined Pituitary Hormone Deficiency ( CPHD)*.

Chen, et al., Abstract, J Soc Gynecol Investig. 2004 Sep. 11(6):393-8.

Corticotropin releasing factor/CRF Elisa Kit and CRF Related products. Cosmo Bio Co., Ltd. http://www.cosmobio.co.jp/export_e/products/elisa/products_YII_20060313.asp. Downloaded Oct. 27, 2008.

HitHunterTM Cortisol Plus Assay, Detection: EFC Chemiluminescent Detection. DiscoyeRx. http://www.discoverx.com/products.php?p=19. Downloaded Oct. 27, 2008.

582701 Tesosterone EIA Kit. Cayman Chemical. http://www.caymanchem.com/app/template/Product.vm/catalog/582701/a/z. Downloaded Oct. 27, 2008.

*hMOR-1A*
   Exon 3a ↓ Exon 3b
---ACTAATCATCAGGTACGCAGTCTCTAGAATTAGGTATATCTACTGGGATGACATAAAAATTATAAGGCTT
  T  N  H  Q  V  R  S  L  * (SEQ ID NO:27)
TGTGCTAAACTAGGAGTTTAATCCATTATAGAGGATGAGAATGGAGGGAAGAGGGAAGCAAGGG (SEQ ID NO:28)

*hMOR-1B1*
   Exon 3a ↓ Exon 5a
---ACTAATCATCAGACAGAAAATAGATTTATTTCAAAAGTCATCTTTACTCAACTGTGAGCATACCAAGGGCTAATA
  T  N  H  Q  K  I  D  L  F  Q  K  S  *S#*  L  L  N  C  E  H  T  K  G  * (SEQ ID NO:29)
ATTACAATATTTTCCCGTGAAAGAATATAAGATTGGAAGC (SEQ ID NO:30)

*hMOR-1B2*
   Exon 3a ↓ Exon 5b
---ACTAATCATCAGAGAGAAGAGACAGAAATCTGACTGGTAAGAAATTGTTACCCTTTTGCCAGCATGCCA
  T  N  H  Q  R  E  R  R  Q  K  *S#*  D  W  —* (SEQ ID NO:31)
GGCTTCTGGGTTCCCTTCCCGAGCGGCCCTAGTGATCCGGCTTGCGGCCACCATGCGCCTACGGGCC--- (SEQ ID NO:32)

*hMOR-1B3*
   Exon 3a ↓ Exon 5c
---ACTAATCATCAGGACCTCCAGCCAAGTTTGTTGCTGACCAACTTGCCGGGTCGTCTTGAAAAGGGGCTT
  T  N  H  Q  G  P  P  A  K  F  V  A  D  Q  L  A  G  S  S  * (SEQ ID NO:33)
ACAGGTGTTCCAAGCCCGTGTTTATCCTGAAGTATCCCTCAACACAGAAAAACGACCTCATAACACAAAA--- (SEQ ID NO:34)

*hMOR-1B4*
   Exon 3a ↓ Exon 5d
---ACTAATCATCAGAGCTGACTATGACATGAACCCTAAAAATTCCTGTTCCC--- (SEQ ID NO:35)
  T  N  H  Q  S  * (SEQ ID NO:36)

FIG. 1B(1)

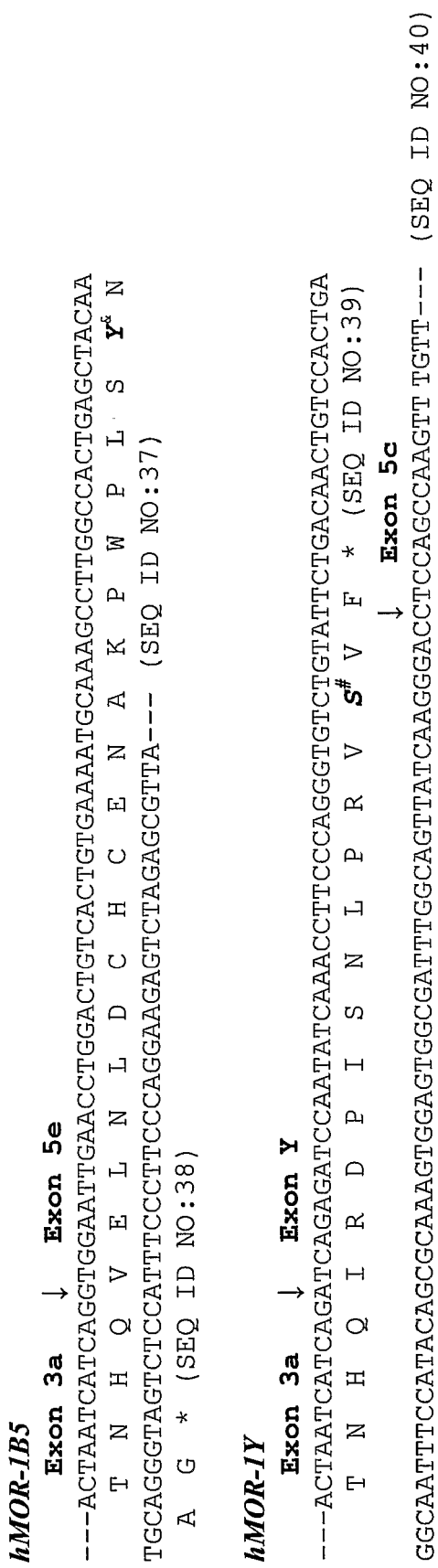
FIG. 1B(2)

: cAMP- and cGMP-dependent protein kinase phosphorylation site
@: Caseine kinase II phosphorylation site
&: Tyrosine kinase phosphorylation site hMOR-1B1 (1354 bp)

CGGAAAGGAAGCGGCTGAGGCGCTTGGAACCCGAAAAGTCTCGGTCTGGTGTCCTGGCTACCTCGCACAGCGGTGCCCGCCC
GGCCGTCAGTACCATGGACAGCAGCGCTGCCCCCACGAACGCCAGCAACTGCACTGATGCCTTGGCGTACTCAAGTTG
CTCCCCAGCCACCAACAGCCCGGTTCCTGGGTCAACTGTCCCACTTAGATGGCAACCTGTCCGACCCATGCGGTCGAAC
CGCACCGACCTGGGCGGGAGAGACAGCCTGTGTCCGCAGTCCTGTGCCCTCCATGATCACGGCCATCACGATCATG
GCCCTCTACTCCAGCTGCAGTCCATCGTGTGCGTGGTGTGGGCTCTGGGAAACTCCTGGTCATGTATGATTGTCAGATACACCAAGAT
GAAGACTGCCACCAACATCTACATTTTCAACCTTGCTCTGGCAGATGCCTTAGCCACCAGTACCCTGCCCTTCAGAGT
GTGAATTACCTAGTGATGTACGTGGTGATCGTTCGCTACACCAAGATGAAGACAGCCACCAACATCTACATCTTCAACCTTGCT
TCACCAGCATATTCACCCTCTGCACATGGCCACCATGCAAAATTATCAATGCTCAACTGGATCCTCTCTTCAGCCATGGGTCTCCTGTAATGTTCAT
CGTACTCCCGGAAATGCCAAAATTATCAATGTCTGCAACTGGATCCTCTCTTCAGCCATTGGTCTCCTGTAATGTTCAT
GGCTACAACAAAATACAGGCAAGGTTCCATGCGCCTTCGCCTTCATTATGCCAGTGCGTGCTATGGATCAGGATGTCTTGCG
CTGAAGATCTGTGTTTTCATCTTCGCCATGCCATGTCTCATCGTGTCTGCTCCAAAGAAAAAGGACAGGAATCTTCAATTCACATCGTCATCATCAAACAGCTGCCTTCCAACCAGTCCTTATGCA
GGTGGTGGTGTCTGTGTTCATCGTCTGTTTCTTGGCACTCGTTGGCACTCGTGCTAAAGCGATGGTTACAATCCAGAAA
CTACGTTCCAGACTGTTTCTTGGCACTCGTGCTAAAGCGATCTGCCTCCCAACCAGTCCTTATGCA
TTTCTGGATGAAACTTCAAAACGATCTCAGAGATGCTTCAGAGAGTTCGTATCCCACGGCCAATACAGTGGATAGAACTAATCATCAGAAATAGATT
CTCGAATTCGTCGAGAACTAGAGAGAACACCTCCACGGCCAATACAGTGGATAGAACTAATCATCAGAAATAGATT
TATTTCAAAAGTCATCTTTACTCAACTGTGAGCATACCAAGGGCTAATAATTACAATATTTTCCGTGAAAGAATATAA
GATTGGAAGC (SEQ ID NO:50)

hMOR-1B1 (406 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYVIVRYTKMKTATNIYIFNLALADALATSTLPFQSVNYLMGTWPFGTILCKIVISIDYYNMFTSIFTLCTMSVDR
YIAVCHPVKALDFRTPRNAKIINVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAFIVCWTPIHIYVIIKALVTIPETTFQTVSWHFCIALGYTNSCLNPV
LYAFLDENFKRCFREFCIPTSSNIEQQNSTRIRQNTRDHPSTANTVDRTNHQKIDLFQKSSLLNCEHTKG (SEQ ID NO:51)

FIG. 3A hMOR-1B2 (2218 bp)

CGGTGCTCCTGGCTACCTCGCACAGCGGTGCCGCCCGGCCGTCAGTACCATGGACAGCAGCGCTGCCCCACGAACG
CCAGCAATTGCACTGATGCCTTGGCGTACTCAAGTTGCTCCCAGCCACCCAGCCCCGGTTCCTGGGTCAACTTGTCCCA
CTTAGATGCAACCTGTCCGACCATGCGGTCCGAACCGACCTGGGCGGGAGAGACAGCCTGTGCCTCCGAC
CGGCAGTCCCTCCATGATCACGGCCATCACCCTCTACTCCATCGTGTGCGTGGTGGGCTCTGTGGGCTCTCTGGAAAC
TTCCTGTCATGTATGTGATTGTCAGATACACCAAGATGAAGACTGCCAACATCTACATTTCAACCTTGCTCTGGC
AGATGCCTAGCCACCAGTACCCTGCCCTTCCAGAGTGTGAATTACCAGCATATTCACCCTCTGCCACCATGGAACCATCCTT
TGCAAGATAGTGATCTCCATAGATTACTATAACATGTTCACCGTACTCCCGAAATGCCAAAATTATCAAGTCTGCAACTG
ACATTGCAGTCTGCCACCCTGTCAAGGCCTTAGATTTCCTGTAATGTTCATGGCAAGGTTCCATAGATTGTACAC
GATCCTCTCTTCAGCCATGGTCTTCTCGTGAAAACCTGCTGAAGATCTGTGTTTCATCTTCGCCTTCATTATGCCAGTG
CTCATCATTACCGTGTGCTATGGACTGATGATCTTGCGCCTCAAGAGTGTGCGTCTGTGTGTCCGACTCCCATTCACAT
ACAGGAATCTTCGAAGGATCACCAGGATGGTGCTGTGGTCAATCCCAGAAACTACGTTCTTCTTGGCACTCTCTGCATTGCTCTAG
TTACGTCATCATTAAAGCCTTGGTTACAATCCCAGTCCTTTATGCATTTCTGGATGAAAACTTCAAACGATGCTTCAGAGTTCTG
GTTACACAAAGCTGCCTCAACATTGAGAACCTCTGCCTGATGCGCAAAATTGAACTCCACTGAATTGCAGCGAACAGACAGACCCCTCCACGGCC
TATCCCAACCTCTTCCAACATTGAGAACTAATCATCAGAGAACAGAGAAGAACAGAAATCTGACTGGTAAGAAATTGTTACCCTTTGCCA
AATACAGTGGATAGAACATCATGGAGCTTCCCTTCCCTGAGCCCTGATCCGGCACCTAGTGATAAACATAGGCATTAGCTACTCTG
GCATGCCAGGCTTCTGGGTTCCATTCCCCAGAGCAAAACACATGTGATAAAACATGGGTTCCATCATCTTTAATCCGACCTCTGACTTGCAGT
TGCATCATAAAGGAAATTTTTTCTTCAGAACTAGCTTAAATTGCCCCCAGTTGGAAAACAGTGCCTCTGAGTAACAGAAAGATCAAGGAGGCCAGAGAA
CTTAGCACGTGCTCTCTTGGGCAAAAGGGTGAAGGTGAAATGATCAAGGAAGTGAATGCTTGTAGAGAAAATTAGTGCAGAAACT
AATGTGCCAGTGGAAGGGTGCTTCTCGGTAGGCAAAGATCTTTTCCAGCAATCCTATTAGTCTCAAGTTCCCTTTTA
GTAGAAGTTCAGCAGCAGTCCCCATGTCCCGGATCCGTACATGTCCAACCCTGCCATCCACAGCCATCAGCAAGAGTGCA
GGGAGGAGAAAAAGCTCCCCATGTCCCGCGATCCGTACATGTCCAACCCTGCCATCCACAGCCATCAGCAAGAGTGCA
AGACAGATTAATCCAAGAGAATAGCAATTAGAAGAGACCTCTAAGCATCAAAGCGTCTTCTTAGCCAAGAGGGACTTTTAAACT
GGAGGTTCTCCTAACACCTCTAAAATCTTAGAAGAGAATCATGGAGGAATGCTTGATAACCCTGGTGATAAGATAAAAACCAAGC
TTTTAATTGACTCCCATCTTAAACAGTTGCAATCCATGAAGGCTTGAGAGAAAATTTTAGTCAAAATCCAACTATAGAA
ATACTAGAAGTGTTCTCTAAAATTAAAAATACAGTAGTTGCTAGAGAAAATTTTATTTCATGGAGATTTATTTCAAAAATCCAATGATGATAAAA
ACATAGAAATGTGAGAGGTAGCACATAAGAAATAAGTCATGGGATTTATTTTCATGGACCAGCAATATGATGATAAAA
GCCATCTAACC (SEQ ID NO:52)

FIG. 3B(1)

hMOR-1B2 (397 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYVIVRYTKMKTATNIYIFNLALADALATSTLPFQSVNYLMGTWPFGTILCKIVISIDYYNMFTSIFTLCTMSVDR
YIAVCHPVKALDFRTPRNAKIINVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALVTIPETFQTVSWHFCIALGYTNSCLNPV
LYAFLDENFKRCFREFCIPTSSNIEQQNSTRIRQNTRDHPSTANTVDRTNHQRERRQKSDW
(SEQ ID NO:53)

FIG. 3B(2)

hMOR-1B3 (2483 bp)

```
CGGTGCTCCTGGCTACCTCGCACAGCGGGTGCCCGGCCGTCAGTACCATGGACAGCAGCGCTGCCCCACGAACG
CCAGCAATTGCACTGATGCCTTGGCGTACTCAAGTTGCTCCCAGCAACCCGGTTCCTGGGTCAACTTGTCCCA
CTTAGATAGCCAACCTGTCCGAACCGCACCGACCCTGGGCGGCGGAGAGACAGCCTGTGCCCTCCGAC
CGGCAGTCCCTCCATGCTCGATCACGGCCATCAACGCAAGATCATGGCCCTCCATCCATGGCCGCTGTGGGCTCTTCGAAAC
TTCCTGGTCATGTATGTGATTGTCAGATACACCAAGATGAAGACTGCCAACATCTACATTTTCAACCTTGCTCTGGC
AGATGCCTTAGCCACCAGTACCCTGCCCTTCCAGAGTGTGAATTACCTGTGAACATGGAACATGCCATTGGAACCATCCTT
TGCAAGATAGTGATCTCCATAGATTACTATAACCAGCATATTCACCTGCCACCATGAGTGTTGATCGAT
ACATTGCAGTCTGCCACCCTGTCAAGGCCTTAGATTCCGTACTCCCGAAAATGCCAAAATTATCAATGTCTGCAACTG
GATCCTCTCTTTCAGCACTTGGTCTCTTCCTGTAATGTTCATGCTACAACAAATACAGGCAAGGTTCCATCTTCGCCTTCATTATGCCAGTG
TAACATTCTCTCATCCAACCTGGTACTGGGAAAACCTGCTGAAGATCTGTTTTCATCTTCGCCTTCATTATGCCAGTG
CTCATCATTACCGTGTGTCTATGGAGGATCACCAGGATGGTGCTGGTGGTGCTGTGTCATCGTCTGTGTCAGACTGTTTCTGGCACTTCTGCATTGCTCTAG
ACAGGAAATCTTCGAAGGATCACCAGGATGGTGCTGGTGGTGCTGTGTCATCGTCTGTGTCAGACTGTTTCTGGCACTTCTGCATTGCTCTAG
TTACGTCATCATTAAAGCCTGGTTACAATCCCAGTCCTTTATGCGTTCTCTGATGAAACTTCAAACGATCTTCAGAGAGTTCTG
GTTACACAAACCCTCTTCCAAACATTGAGCAACAACTCCACTGAATTCGTCAGAACACTAGAGACCCTCCAGGCC
TATCCCAATAGAGGATAGAACTAATCATCAGGGACCTCAGTTGTTGTGCTGACCAAGTATCCCTCAACACAGAAACGACCTCATAACACAAAT
GGGGCTTACAGTGTTCCAAGCCCGTGTTTATCCTGAAGTATCCCTCAACACAGAAACGACCTCATAACACAAAT
ACACCAGCTTAAAAAATAGCCTTAAAATCAAAACTTTACAGGAGATAAACACTGATTTTTTAT
TTTATTTTTATTTATTTATTTGCCAGCATGCCATCATTCATCAACCGTTGCACAGCAGCTTAAATTGCCCCTGAGCGGCCCTGATCGGCTTG
CGGCACCATGCCCTACGGGCAAGCTGCCTTAGCTCTGCTTGCCAGAGCTGCAATCATAAGGAGGCCCTGATCGGCTTG
TAAAACATAGGCATTAGTACTCTGCAGTTTCAACACGTGCCAGTGGAAGGTGAAATGATCAAGGAGGCCAGAGAAA
CTTTAATCGACCTCTGACTTGCAGTTGCAGGAAAAAACGTGCCAGTGGAAGGTGAAATGATCAAGGAGGCCAGAGAAA
GAAAGGAAAAAGGAGGAGCAACACTGTAGAAGTTCAGGCAGTCGCTCCAACCCTGCCGTCC
GACTCACCTATTGAGGCAACACTGTAGAAGTTCAGGCAGTCGCTCCAACCCTGCCGTCC
TTAGCTCTCAAGTTTCCCTTTTAGGGAGGAAAAGCTCCCATGCCGTACATGTCCAATCCCATAGCATCAAAGCTGTTC
ACAGCCATCAGCAAAGAGTGCAAGACAGATTAATCCAAAGAGAATAGCGATTAATATCCCATAGCATCAAAGCTGTTC
TTAGCCAAGGGACTTTAACGAGAGGGTCTCTAACACCCTAAATCTTAGAAGACTCTAACCATCCTAAGTAGGG
CCTCTAACCCGCTTTATAAACTTTAATTGACTCCCATCTTAACAGTTGCAATCCATGGAGGAATGCTTGATAACCTCG
GTGATAAGATAAAACCAAGCATACTAGAAGTGTCTCTAAATTAAAATACAGTAGTGCTAGAGAAAATTTTA
```

FIG. 3C(1)

GTCCAAAATCCAACTATAGAAACATAGAAATGTGAGAGGCAGCACATAAGAAATAAGTCATGGGGATTTTATTTCAT
GGACCAGCAATATGATGATAAAAGCCATCTAACC (SEQ ID NO:54)

hMOR-1B3 (403 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYVIVRYTKMKTATNIYIFNLALADALATSTLPFQSVNYLMGTWPFGTILCKIVISIDYYNMFTSIFTLCTMSVDR
YIAVCHPVKALDFRTPRNAKIINVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALVTIPETFQTVSWHFCIALGYTNSCLNPV
LYAFLDENFKRCFREFCIPTSSNIEQQNSTRIRQNTRDHPSTANTVDRTNHQGPPAKFVADQLAGSS (SEQ ID NO:55)

FIG. 3C(2)

hMOR-1B4 (1251 bp)

CGGTGCTCCTGGCTACCTCGCACAGCGGGTGCCCGGCCGTCAGTACCATGGACAGCAGGCTGCCCCACGAACG
CCAGCAATTGCACTGATGCCTTGGCGTACTCAAGTTGCTCCCAGCACCACCCAGCCGTTCCTGGGTCAACTTGTCCA
CTTAGATGGCAACCTGTCCGACCCATGCGGGTCCGAACCGACCGGGCGGGAGAGACAGCCTGTGCCCTCCGAC
CGGCAGTCCCTCCATGATCACGGCCATCACGATCATGGCCCTCTACTCCATCGTGTGCGTGGTGGGCTCTTCGGAAAC
TTCCTGGTCATGTATGTGATTGTCAGATACACCAAGATGAAGACTGCCACCAACATCTACGTTTTCAACCTTGCTCTGGC
AGATGCCTTAGCCACCAGTACCCTGCCCTTCCAGAGTGTGAATTACCTAATGGGAACATGGCCATTTGGAACCATCCTT
TGCAAGATAGTGATCTCCATAGATTACTACAACATGTTCACCAGCATATTCACCCTGTGCACCATGAGTGTTGATCGAT
ACATTGCAGTCTGCCACCCTGTCAAGGCCTTAGATTTCCGTACTCCCCGAAATGCCAAAATTATCAATGTCTGCAACTG
GATCCTCTCTTCAGCCATTGGTCTTCCTGTAATGTTCATGGCTACAACCTGTAAACAAATACAGGCAAGGTTCCATAGATTGTACAC
TAACATTCTCATCCAACCTGTGGGAAAACCTGTGAAGATCTGTGTTTTCATCTTCGCCTTCATTATGCCAGTG
CTCATCATTACGGTGTGCTATGGACTTATGATCCTTCGGCCTCAAGAGTGTCCGCATGCTCTCTGCTCAAGAAAAGG
ACAGGAATCTTCGAAGGATCACCAGGATGGTGCTGGTGGTTGTTGTGGCTGTTCATCATGTTCTTGGCCACTCTTCTGCATTCACAT
TTACGTCATCATTAAAGCTCTTGTTACAATCCCAGAAATCACGTTCCAGACTGTTCTTCGACACTTCTGCATTGCTCTAG
GTTACACAAACAGCTGCCTCAACCCCTCTCCAACCATTGAGCAACAAACCTCACTGTCAGAACTCAAACGATGCTTCAGAGAGTTCTG
TATCCCAACCTCTTCCAACTAATCATCAGAGCTGACTATGACCATGAACCCTAAAATTCCTGTTCCC (SEQ ID NO:56)

hMOR-1B4 (389 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYVIVRYTKMKTATNIYVFNLALADALATSTLPFQSVNYLMGTWPFGTILCKIVISIDYYNMFTSIFTLCTMSVD
RYIAVCHPVKALDFRTPRNAKIINVCNWILSSAIGLPVMFMATTKYRQGSIDCTLTFSHPTWYWENLLKICVFIFAFIMPVLIIT
VCYGLMILRLKSVRMLSGSKEKDRNLRRITRMVLVVVAVFIVCWTPIHIYVIIKALVTIPETTFQTVSWHFCIALGYTNSCLNP
VLYAFLDENFKRCFREFCIPTSSNIEQQNSTRIRQNTRDHPSTANTVDRTNHQS (SEQ ID NO:57)

FIG. 3D hMOR-1B5 (1402 bp)

CGGTGCTCCTGGCTACCTCGGCACAGGCGGTGCCCGGCCCCGTCAGTACCATGGACAGCAGCGCTGCCCCACGAACG
CCAGCAATTGCACTGATGCCTTGGCTACTCAAGTTGCTCCCAGCACCCAGCCCCGTTCCTGGTCAACTTGTCCCA
CTTAGATGGCAACCTGTCCGACCCATGGGTCCGAACCGATCATGAACCGACCTGGGCGGGAGAGACAGCCTGTGCCCTCCGAC
CGGCAGTCCCTCCATGATCACGGCCATCACCATAATGGCCCTCTACTCCATGTGCTGTGGGCTCTTCGAAAC
TTCCTGGTCATGTATGTGATTGTCAGATACACCAAGATGAAGACTAACACATCTACATTTCAACCTGCTCTGGC
AGATGCCTTAGCCACCAGTACCCTCCCTCCAGAGTGTGAATTACCTAATGGGAACATGGCCATTTGAACCATCCTT
TGCAAGATAGTGATCTCCATAGATGTTCACCAGCATATTCCCCTCTGCACCAGAGTGTTGATGAT
ACATTGCAGTCTGCCACCTGTCAAGGCCTTAGATTTCCGTAATGTTCATGGCTCTGTAATGCTGGCTACACAACAAATACAGGCAAGTTCCATAGATTGTACAC
GATCCTCTTCAGCCATTGGTCTTCCTGTAATGTTGTTCATGGCTACAACAAATACAGGCAAGTTCATCTTCGCCTTCATTATGCCAGTG
TAACATTCTCTCATCCAACCTGGTGTGCTATGGACTGTGCGCTCAAGAGTGTCGCTGTGTGTGTGCTCTCCTGGCTCTGACTCCATTCACAT
ACAGGAATCTTCGAAGGATCACCAGATGGTGGTGCTCCAGAAACTACGTTTCTTGGCACTTCTCTGCATTGCTCTAG
TTACGTTCATCATTAAAGCTGCCTACAACCAGTCCTTTAATGCATTTCCTGAGAACGATGCTTCAAACGATGCTTCAGAGAGTTCTG
GTTACAACAAACAGCTCCCAACATTGAGCAACAAAACTCCACTCAGTGGAATTGAACCTGGACTGTCACTGAACCTTTGGCCACTG
TATCCCAACCTCTTCCAACATTGAGCAACAAAACTCCACTCAGTGGAATTGAACCTGGACTGTCACTGAACCTTGGCCACTG
AATACAGTGGATAGAACTCATCAGGTGTCTCCATTCCCCTTCCCCAGGAAGAGACCCTAAAATGCAAAGCCTTGGCCACTG
AGCTACAATGCAGGTAGTCCATTCCCCTTCCCCAGGAAGAGACCCTAAAATTCCTGTTCCC (SEQ ID NO:58)
ACTATTCATATGATTTTAGAGCTGACTATGACATGAACCCTAAAATTCCTGTTCCC (SEQ ID NO:58)

hMOR-1B5 (410 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYVIVRYTKMKTATNIYIFNLALADALATSILPFQSVNYLMGTWPFGTILCKIVISIDYYNMFTSIFTLCTMSVDR
YIAVCHPVKALDFRTPRNAKIINVCNWILSSAIGLPVMFMATKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALVTIPETTFQTVSWHFCIALGYTNSCLNPV
LYAFLDENFKRCFREFCIPTSSNIEQQNSTRIRQNTRDHPSTANTVDRTNHQVELNLDCHCENAKPWPLSYNAG (SEQ ID NO:59)

FIG. 3E hMOR-1Y (2601 bp)

```
CGGTGCTCCTGGCTACCTCGCACAGCGGTGCCCGCCGGTGCCCTCAGTACCATGGACAGCAGCGCTGCCCCACGAACG
CCAGCAATTGCACTGATGCCTTGCCGTCAAGTTGCTCCCCAGCCAGCCGGTTCCTGGGTCAACTTGTCCCA
CTTAGATGGCAACCTGTCCGACCCATGCGGTCCGAACCCACCGACCTGGGCGGGAGAGACAGCCTGTGCCCTCCGAC
CGGCCAGTCCCTCCATGATCACGATCATGCCCTCTACTCCATCGTGTGCGTGGTGGGGCTCTTCGGAAAC
TTCCTGGTCATGTATGTGATTGTCAGATACACCAAGATGAAGACTGCCACCAACATCTACATTTTCAACCTTGCTCTGGC
AGATGCCTTAGCCACCAGTACCCTGCCCTTCCAGAGTGTGAATTACCTGATGGGAACATGGCCATTTGAACCATCCT
TGCAAGATAGTGATCTCCATAGATTACTATAACATGTTCACCAGCATATTCACCCTGTGCACCATGAGTGTTGATCGAT
ACATTGCAGTCTGCCACCCTGTGAAGGCCCTTAGATGGTCTTCCTGTAAATGTTCATGGCAACAAATATCAAGTTCCATAGATTGTACAC
GATCCTCTTCAGCACTTGGTCTTCCTGTACTGGAAACCTGCTGAAATCTGTGTTTTTCATCTTCGCCTTCATTATGCCAGTG
TAACATTCTCTCATTACCGTGTCTATGACTGAGATCACCAAGGATGTGTGTGGTGCTGGTGTGTTGTCATGATGTTTCATTCACAT
ACAGGAATCTTGAAGGATCACCAAGGATGTGGTGGTCCAGAAACTACGTTCTTCAGTGACATGCTTCAGAGAGTTCTG
TTACGTCATCATCATTAAGCCTGCTCAACCCAGTTCATTTATGCGAAACTCCACTCGAAATTCGTCAGAACCTGAGATTCAAAAACCTCAAACGATGCTTCAGAGAGTTCTG
GTTACAACAAACCTCTTCCAACATTGAGCAACAAACTCCACTCGAAATTCGTCAGAACTAGAGACCACCCCTCCACGGCC
TATCCAACCTCTCCAACATTGAGCAATCATCAGAGAATCCAATATCAAACCTTCCCAGGGTGTCTGTATTCTGACAACTGT
AATACAGTGGATAGAACTTCCATACACAGGCAAAGTGGAGTGGCCAAAGTGGGGGCTTACAGGTGTCCAAGCCTGCAGTATCAAGGACCTCCAGCCAAGTTGTGTG
CCACTGAGGCAATTCCCATACAGGCAAAGTGGAGTGGGGGCTTACAGGTGTCCAAGCCTGCAGTTATCAAGGACCTCCAGCCAAGTTGTGTG
CTGACCAACTGCCGTCGTCATAACGACCTCATAAGCCTTGAAAGGGGGTCGTCTGAATTATTTTATATTTTATTGCCAGATGCCAGGCTTCTGGGTTCC
ACACAGAGAAAACGAAGAAGACAGAAATCTGACTGGTAAAGAAAATTGTTACCCTTTGTACCCTTTGCCAGCATGCCAGGCTTCTGGGTTCC
CACAGAGAGAAGAAGAAGACAGAAATCTGACTGGTAAAGAAAATTGTTACCCTTTGTACCCTTTGCCAGCATGCCAGGCTTCTGGGTTCC
CTTTCCCTGAGCGGGCCCTAGTGATCCGGCTTGCGCAACATGTGATAAAACATAGCCAAGCTGCATCATAAAGGAAATTTTT
TTTTCATTCTGGCCAATTTGCCCTCCAGATGGGGTCCATCATCTTAATCGACCTCTGACTTGCAGTTTCACCACGTGCTCTCTGG
TAGCTTAAATTTGCCCTCCAGATGGGGTCCATCATCTTAATCGACCTCTGACTTGCAGTTTCACCACGTGCTCTCTGG
CAAAACAGTTGGCAAAAGGATCTTTTCCGGCAATCCTATTAGCTCTCAAGTTCCCCTTTTAGGGAGGAAAAAGCTCCCAT
GGGAAGGTGAAATGATCAAGGAGGCCAGAGTAACAGAGACTCACCTATTGCAGCAACACTGTAGAAGTTCAGGCAGCTGC
TTCTCGGGTAGCAAAAGGATCTTTTCCGCAATCCTATTAGCTCTCAAGTTCCCCTTTTAGGGAGGAAAAAGCTCCCAT
GTCCCGCGATCCTGTACATGTCCAACCCTGTCAAGCTGTCTTAGCACAGCAGCAAAGAGGGACTTTAACGAGAGGGGTCTTAACACCCTA
ATAGCAATTAATATCCCATAGCATCAAGCTGTCTTAGCACAGCAGCAAAGAGGGACTTTATAAACTTTTAATTGAACTTTAATGACTCCATCTTAAC
AATCTTAGAAGAGACCCTAACCATCCTAAGTAGGGCCTCTAACCCCGCTCTAACCCCGCTCTTATAAACTTTTAATTGAACTCCATCTTAAC
```

FIG. 3F(1)

AGTTGCAATCCATGGAGGAATGCTTGATAACCTCGGTGATAAGATAAAAAAACCAAGCATACTAGAAGTGTCTCTAAA
ATTAAAATACAGTAGTTGCTAGAGAAAAATTTTAGTCCAAAAATCCAACTATAGAAACATAGAATGTGAGAGGTAGC
ACATAAGAAATAAGTCATGGGGATTTTATTTCATGGACCAGCAATATGATGATAAAGCCATCTAACCAAGGGC
(SEQ ID NO:60)

hMOR-1Y (402 aa)

MDSSAAPTNASNCTDALAYSSCSPAPSPGSWVNLSHLDGNLSDPCGPNRTDLGGRDSLCPPTGSPSMITAITIMALYSIVCVV
GLFGNFLVMYYVIVRYTKMKTATNIYFNLALADALATSTLPFQSVNYLMGTWPFGTILCKIVISIDYYNMFTSIFTLCTMSVDR
YIAVCHPVKALDFRTPRNAKIINVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALVTIPETFQTVSWHFCIALGYTNSCLNPV
LYAFLDENFKRCFREFCIPTSSNIEQQNSTRIRQNTRDHPSTANTVDRTNHQIRDPISNLPRVSVF (SEQ ID NO:61)

FIG. 3F(2)

```
hMOR-1      (1) MDSSAAPTNASNCTDALAYSSCSPAPSPGSWVNLSHLDGNLSDPCGPNRTDLGGRDSLCP
hMOR-1A     (1) MDSSAAPTNASNCTDALAYSSCSPAPSPGSWVNLSHLDGNLSDPCGPNRTDLGGRDSLCP
hMOR-1B1    (1) MDSSAAPTNASNCTDALAYSSCSPAPSPGSWVNLSHLDGNLSDPCGPNRTDLGGRDSLCP
hMOR-1B2    (1) MDSSAAPTNASNCTDALAYSSCSPAPSPGSWVNLSHLDGNLSDPCGPNRTDLGGRDSLCP
hMOR-1B3    (1) MDSSAAPTNASNCTDALAYSSCSPAPSPGSWVNLSHLDGNLSDPCGPNRTDLGGRDSLCP
hMOR-1B4    (1) MDSSAAPTNASNCTDALAYSSCSPAPSPGSWVNLSHLDGNLSDPCGPNRTDLGGRDSLCP
hMOR-1B5    (1) MDSSAAPTNASNCTDALAYSSCSPAPSPGSWVNLSHLDGNLSDPCGPNRTDLGGRDSLCP
hMOR-1O     (1) MDSSAAPTNASNCTDALAYSSCSPAPSPGSWVNLSHLDGNLSDPCGPNRTDLGGRDSLCP
hMOR-1X     (1) MDSSAAPTNASNCTDALAYSSCSPAPSPGSWVNLSHLDGNLSDPCGPNRTDLGGRDSLCP
hMOR-1Y     (1) MDSSAAPTNASNCTDALAYSSCSPAPSPGSWVNLSHLDGNLSDPCGPNRTDLGGRDSLCP
Consensus   (1) MDSSAAPTNASNCTDALAYSSCSPAPSPGSWVNLSHLDGNLSDPCGPNRTDLGGRDSLCP 61                                                       120
hMOR-1     (61) PTGSPSMITAITIMALYSIVCVVGLFGNFLVMYVIVRYTKMKTATNIYIFNLALADALAT
hMOR-1A    (61) PTGSPSMITAITIMALYSIVCVVGLFGNFLVMYVIVRYTKMKTATNIYIFNLALADALAT
hMOR-1B1   (61) PTGSPSMITAITIMALYSIVCVVGLFGNFLVMYVIVRYTKMKTATNIYIFNLALADALAT
hMOR-1B2   (61) PTGSPSMITAITIMALYSIVCVVGLFGNFLVMYVIVRYTKMKTATNIYIFNLALADALAT
hMOR-1B3   (61) PTGSPSMITAITIMALYSIVCVVGLFGNFLVMYVIVRYTKMKTATNIYIFNLALADALAT
hMOR-1B4   (61) PTGSPSMITAITIMALYSIVCVVGLFGNFLVMYVIVRYTKMKTATNIYIFNLALADALAT
hMOR-1B5   (61) PTGSPSMITAITIMALYSIVCVVGLFGNFLVMYVIVRYTKMKTATNIYIFNLALADALAT
hMOR-1O    (61) PTGSPSMITAITIMALYSIVCVVGLFGNFLVMYVIVRYTKMKTATNIYIFNLALADALAT
hMOR-1X    (61) PTGSPSMITAITIMALYSIVCVVGLFGNFLVMYVIVRYTKMKTATNIYIFNLALADALAT
hMOR-1Y    (61) PTGSPSMITAITIMALYSIVCVVGLFGNFLVMYVIVRYTKMKTATNIYIFNLALADALAT
Consensus  (61) PTGSPSMITAITIMALYSIVCVVGLFGNFLVMYVIVRYTKMKTATNIYIFNLALADALAT
```

FIG. 4(1)

|          |       |                                                                                  |
|----------|-------|----------------------------------------------------------------------------------|
| hMOR-1   | (121) | STLPFQSVNYLMGTWPFGTILCKIVISIDYYNMFTSIFTLCTMSVDRYIAVCHPVKALDF |
| hMOR-1A  | (121) | STLPFQSVNYLMGTWPFGTILCKIVISIDYYNMFTSIFTLCTMSVDRYIAVCHPVKALDF |
| hMOR-1B1 | (121) | STLPFQSVNYLMGTWPFGTILCKIVISIDYYNMFTSIFTLCTMSVDRYIAVCHPVKALDF |
| hMOR-1B2 | (121) | STLPFQSVNYLMGTWPFGTILCKIVISIDYYNMFTSIFTLCTMSVDRYIAVCHPVKALDF |
| hMOR-1B3 | (121) | STLPFQSVNYLMGTWPFGTILCKIVISIDYYNMFTSIFTLCTMSVDRYIAVCHPVKALDF |
| hMOR-1B4 | (121) | STLPFQSVNYLMGTWPFGTILCKIVISIDYYNMFTSIFTLCTMSVDRYIAVCHPVKALDF |
| hMOR-1B5 | (121) | STLPFQSVNYLMGTWPFGTILCKIVISIDYYNMFTSIFTLCTMSVDRYIAVCHPVKALDF |
| hMOR-1O  | (121) | STLPFQSVNYLMGTWPFGTILCKIVISIDYYNMFTSIFTLCTMSVDRYIAVCHPVKALDF |
| hMOR-1X  | (121) | STLPFQSVNYLMGTWPFGTILCKIVISIDYYNMFTSIFTLCTMSVDRYIAVCHPVKALDF |
| hMOR-1Y  | (121) | STLPFQSVNYLMGTWPFGTILCKIVISIDYYNMFTSIFTLCTMSVDRYIAVCHPVKALDF |
| Consensus| (121) | STLPFQSVNYLMGTWPFGTILCKIVISIDYYNMFTSIFTLCTMSVDRYIAVCHPVKALDF |

|          |       |                                                                                  |
|----------|-------|----------------------------------------------------------------------------------|
| hMOR-1   | (181) | RTPRNAKIINVCNWILSSAIGLPVMFMATTKYRQGSIDCTLTFSHPTWYWENLLKICVFI |
| hMOR-1A  | (181) | RTPRNAKIINVCNWILSSAIGLPVMFMATTKYRQGSIDCTLTFSHPTWYWENLLKICVFI |
| hMOR-1B1 | (181) | RTPRNAKIINVCNWILSSAIGLPVMFMATTKYRQGSIDCTLTFSHPTWYWENLLKICVFI |
| hMOR-1B2 | (181) | RTPRNAKIINVCNWILSSAIGLPVMFMATTKYRQGSIDCTLTFSHPTWYWENLLKICVFI |
| hMOR-1B3 | (181) | RTPRNAKIINVCNWILSSAIGLPVMFMATTKYRQGSIDCTLTFSHPTWYWENLLKICVFI |
| hMOR-1B4 | (181) | RTPRNAKIINVCNWILSSAIGLPVMFMATTKYRQGSIDCTLTFSHPTWYWENLLKICVFI |
| hMOR-1B5 | (181) | RTPRNAKIINVCNWILSSAIGLPVMFMATTKYRQGSIDCTLTFSHPTWYWENLLKICVFI |
| hMOR-1O  | (181) | RTPRNAKIINVCNWILSSAIGLPVMFMATTKYRQGSIDCTLTFSHPTWYWENLLKICVFI |
| hMOR-1X  | (181) | RTPRNAKIINVCNWILSSAIGLPVMFMATTKYRQGSIDCTLTFSHPTWYWENLLKICVFI |
| hMOR-1Y  | (181) | RTPRNAKIINVCNWILSSAIGLPVMFMATTKYRQGSIDCTLTFSHPTWYWENLLKICVFI |
| Consensus| (181) | RTPRNAKIINVCNWILSSAIGLPVMFMATTKYRQGSIDCTLTFSHPTWYWENLLKICVFI |

FIG. 4(2)

```
              241                                                                    300
hMOR-1    (241) FAFIMPVLIITVCYGLMILRLKSVRMLSGSKEKDRNLRRITRMVLVVVAVFIVCWTPIHI
hMOR-1A   (241) FAFIMPVLIITVCYGLMILRLKSVRMLSGSKEKDRNLRRITRMVLVVVAVFIVCWTPIHI
hMOR-1B1  (241) FAFIMPVLIITVCYGLMILRLKSVRMLSGSKEKDRNLRRITRMVLVVVAVFIVCWTPIHI
hMOR-1B2  (241) FAFIMPVLIITVCYGLMILRLKSVRMLSGSKEKDRNLRRITRMVLVVVAVFIVCWTPIHI
hMOR-1B3  (241) FAFIMPVLIITVCYGLMILRLKSVRMLSGSKEKDRNLRRITRMVLVVVAVFIVCWTPIHI
hMOR-1B4  (241) FAFIMPVLIITVCYGLMILRLKSVRMLSGSKEKDRNLRRITRMVLVVVAVFIVCWTPIHI
hMOR-1B5  (241) FAFIMPVLIITVCYGLMILRLKSVRMLSGSKEKDRNLRRITRMVLVVVAVFIVCWTPIHI
hMOR-1O   (241) FAFIMPVLIITVCYGLMILRLKSVRMLSGSKEKDRNLRRITRMVLVVVAVFIVCWTPIHI
hMOR-1X   (241) FAFIMPVLIITVCYGLMILRLKSVRMLSGSKEKDRNLRRITRMVLVVVAVFIVCWTPIHI
hMOR-1Y   (241) FAFIMPVLIITVCYGLMILRLKSVRMLSGSKEKDRNLRRITRMVLVVVAVFIVCWTPIHI
Consensus (241) FAFIMPVLIITVCYGLMILRLKSVRMLSGSKEKDRNLRRITRMVLVVVAVFIVCWTPIHI 301                                                                    360
hMOR-1    (301) YVIIKALVTIPETTFQTVSWHFCIALGYTNSCLNPVLYAFLDENFKRCFREFCIPTSSNI
hMOR-1A   (301) YVIIKALVTIPETTFQTVSWHFCIALGYTNSCLNPVLYAFLDENFKRCFREFCIPTSSNI
hMOR-1B1  (301) YVIIKALVTIPETTFQTVSWHFCIALGYTNSCLNPVLYAFLDENFKRCFREFCIPTSSNI
hMOR-1B2  (301) YVIIKALVTIPETTFQTVSWHFCIALGYTNSCLNPVLYAFLDENFKRCFREFCIPTSSNI
hMOR-1B3  (301) YVIIKALVTIPETTFQTVSWHFCIALGYTNSCLNPVLYAFLDENFKRCFREFCIPTSSNI
hMOR-1B4  (301) YVIIKALVTIPETTFQTVSWHFCIALGYTNSCLNPVLYAFLDENFKRCFREFCIPTSSNI
hMOR-1B5  (301) YVIIKALVTIPETTFQTVSWHFCIALGYTNSCLNPVLYAFLDENFKRCFREFCIPTSSNI
hMOR-1O   (301) YVIIKALVTIPETTFQTVSWHFCIALGYTNSCLNPVLYAFLDENFKRCFREFCIPTSSNI
hMOR-1X   (301) YVIIKALVTIPETTFQTVSWHFCIALGYTNSCLNPVLYAFLDENFKRCFREFCIPTSSNI
hMOR-1Y   (301) YVIIKALVTIPETTFQTVSWHFCIALGYTNSCLNPVLYAFLDENFKRCFREFCIPTSSNI
Consensus (301) YVIIKALVTIPETTFQTVSWHFCIALGYTNSCLNPVLYAFLDENFKRCFREFCIPTSSNI
```

FIG. 4(3)

```
             361                                                              420
hMOR-1    (361) EQQNSTRIRQNTRDHPSTANTVDRTNHQLENLEAETAPLP------------------------
hMOR-1A   (361) EQQNSTRIRQNTRDHPSTANTVDRTNHQVRSL----------------------------------
hMOR-1B1  (361) EQQNSTRIRQNTRDHPSTANTVDRTNHQKIDLFQKSSLLNCEHTKG--------------------
hMOR-1B2  (361) EQQNSTRIRQNTRDHPSTANTVDRTNHQRERRQKSDW-----------------------------
hMOR-1B3  (361) EQQNSTRIRQNTRDHPSTANTVDRTNHQGPPAKFVADQLAGSS-----------------------
hMOR-1B4  (361) EQQNSTRIRQNTRDHPSTANTVDRTNHQS-------------------------------------
hMOR-1B5  (361) EQQNSTRIRQNTRDHPSTANTVDRTNHQVELNLDCHCENAKPWPLSYNAG----------------
hMOR-1O   (361) EQQNSTRIRQNTRDHPSTANTVDRTNHQPPLAVSMAQIFTRYPPPTHREKTCNDYMKR--------
hMOR-1X   (361) EQQNSTRIRQNTRDHPSTANTVDRTNHQCLPIPSLSCWALEHGCLVVYPGPLQGPLVRYD
hMOR-1Y   (361) EQQNSTRIRQNTRDHPSTANTVDRTNHQIRDPISNLPRVSVF------------------------
Consensus (361) EQQNSTRIRQNTRDHPSTANTVDRTNHQ 421                                  446
hMOR-1    (401) ------------------------------------ (SEQ ID NO:62)
hMOR-1A   (393) ------------------------------------ (SEQ ID NO:63)
hMOR-1B1  (407) ------------------------------------ (SEQ ID NO:51)
hMOR-1B2  (398) ------------------------------------ (SEQ ID NO:53)
hMOR-1B3  (404) ------------------------------------ (SEQ ID NO:55)
hMOR-1B4  (390) ------------------------------------ (SEQ ID NO:57)
hMOR-1B5  (411) ------------------------------------ (SEQ ID NO:59)
hMOR-1O   (419) ------------------------------------ (SEQ ID NO:64)
hMOR-1X   (421) LPAILHSSCLRGNTAPSPSGGAFLLS (SEQ ID NO:65)
hMOR-1Y   (403) ------------------------------------ (SEQ ID NO:61)
Consensus (388)                                      (SEQ ID NO:66)
```

FIG. 4(4)

rMOR-1A

Exon 3a → Exon 3b

----AACCACCAGGTATGTGCTTTCTAGAATTACGGATAACATATAAAAATACCATATCTGGTA
     N  H  Q  V  C  A  F  *  (SEQ ID NO:67)

CCAGTCTAAGATTTAAATCTTTAAGAAGGTCAGTAACTTGAGGCAAAGTCC (SEQ ID NO:68)

rMOR-1C1

Exon 3a → Exon 7

----AACCACCAGCCCTGGCAGTCAGCGTGGCCCAGATCTTTACAGGATATCCTTCTCCG
     N  H  Q  P  A  L  A  V  S  V  A  Q  I  F  T  G  Y  P  S  P
                                          → Exon 8

ACTCATGGTGAAAAACCCTGCAAGAGTTACAGGGACAGAGTTACAGAGACCCTGTGGAAGAACGTGGT
 T  H  G  E  K  P  C  K  S  Y  R  D  R  P  R  P  C  G  R  T  W

CTTTGAAATCGCGTGCAGAATCCAATGTGGAGCACTTCCATTGTGGAGCCCGCCATTAATCTATAA
 L  K  S  R  A  E  S  N  V  E  H  F  H  C  G  A  A  L  I  Y  N
 → Exon 9a CAATGTGAATTTCATCTAAACACAGGGATGTGCTAGTGAGAAGTTTGGAGGTGCAGGC (SEQ ID NO:69)
 N  V  N  F  I  *  (SEQ ID NO:70)

FIG. 5(1)

rMOR-1C2

Exon 3a → Exon 7
----AACCACCAGCCCTGGCAGTCAGGCGTGGCCCAGATCTTTACAGGATATCCTTCTCCG
    N  H  Q  P  A  L  A  V  S  V  A  Q  I  F  T  G  Y  P  S  P
                                              → Exon 8
ACTCATGGTGAAAAACCCTGCAAGAGTTACAGGGACAGACCCTGTGGAAGAACGTGGT
 T⁰ H  G  E  K  P  C  K  S⁰ Y  R  D  R  P  R  P  C  G  R  T  W
CTTTGAAATCGCGTGCAGAATCCAATGTGGAGCACTTCCATTGTGGAGCCGCATTAATCTATAA
 S↔ L  K  S⁰ R  A  E  S⁰ N  V  E  H  H  F  H  C  G  A  A  L  I  Y  N
                        → Exon 9b
CAATGAACTAAAAATAGGGCCAGTGTCCTGGCTCCAGATGCCTGCGCACGTGCTCGTGCGCCCC
 N  E  L  K  I  G  P  V  S  W  L  Q  M  P  A  H  V  L  V  R  P
TGGTAATGAACACGGGCTCCGATTCTGAATATCCTTCTGTG (SEQ ID NO:71)
 W  *  (SEQ ID NO:72)

rMOR-1D

Exon 3a → Exon 8
----AACCACCAGACCCTGTGGAAGAACGTGGTCTTTGAAATCGCGTGCAGAATCCAA
    N  H  Q  T  *  (SEQ ID NO:73)                → Exon 9b
TGTGGAGCACTTCCATTGTGGAGCCGCATTAATCTATAACAATGAACTAAAAATAGGGCCAGTG
TCCTGGCTCCAGATGCCTGCGCACGTGCTCGTGCGCCCCTGGTAATGAACACGGGCTCCGATTC
TGAATATCCTTCTGTG (SEQ ID NO:74)

FIG. 5(2)

rMOR-1B2

Exon 3a    ↓    Exon 5b
----AACCACCAGGAGCCCTCAGTCAGTAGAGACATGATGTGAATGAACCAACTGATTAAACAAG
    N   H   Q   E   P   Q   S   V   E   T   *   (SEQ ID NO:75)
GTTTTCTGAACACTGAAACACAAATGTAGAGGTTACTAGAGAAATTGTAGCCTGAAAATTCAATTACGGAAACCAAATGAGT
GTGAGTGTATACATTTTAAGGCCTGGGACTAAAGAAATGTTAGCCCTCACACAGACAGGCCTCACACTTCAGTAATGAGCAAATTAGA
CAAAGACAATTCTAGAGCCTGGGACTAAAGAAATGTTAGCCCTCACACAGACAGGCCTCACACTTCAGTAATGAGCAAATTAGA
TTAGTGAGAAAGATGGAGGAAAGACTCGAAATATTTTCATATCTTCCTGTGGAACTCCACAAGAAAACCAATAGAATAAACCAACCTGC
TGGACCCCTTGGTGGCTCTTACC (SEQ ID NO:76)

rMOR-1E

Exon 3a    ↓    Exon E
----AACCACCAGGGAGGAGCAGAGTTATGAGGATTAATACAAAAAGACTACCACGTCCTTCAGAGG
    N   H   Q   G   A   E   L   *   (SEQ ID NO:77)
AGCAGCCAGAGGGAGGCCTTGGCCCCCACAATGGTAGGTGCTCCCCACTGTTGCTCTCCCCATCACACACATCTCTCACTGTTCCCTTTGT
TTTCAGCTATGGCTACCCGGCATAGCCTTTCAGTCTTTCTGACTTGACCTCAGATTTATGCAATACAACCTAGATGATCCGCCTCA
GGAGACAGGAATGCTCATACCGAAGTGTGGCTAATGCAATATTAACAAATTTATCTCCCTGCTTCCAGCTCATTGTTATCCACATCAACACATAACCCTTTA
GCAGAGTCATCCCCACTCTCTCTCTCTCCACTCTCTCTCTTGCCCTGCACTTTGAAAGGGTAAGGATTTAAATTGATTTTTTTCTTC
CTCTGTTGCCTTCTCTCTCTCTTTTAGGGGTTTTCAAACTCTCGCCTGCACTTTGAAAGGGTAAGGATTTAAATTGATTTTTTTCTTC
CTTTTTCTAAGCAGCCCTCTTTTTAGGGGATAACATTCTAGAGCAAGCAATTGAAACTATCTATACAAACTGAGCTTCAAATCTTTGCATTTAAATATTT
TGCTTTCATTGGAGAGAAAGGAAGAGCATAGGAAAAGCTTCCTAGGACACTGTTGGGCCTTCTTATCCTGCTTGTCCTGCTTCCCTCCCAGGCT
TGTAGGGGTGTGCTTGGTAGCTTCCTAGGACACTGTTGGGCCTTCTTATCCTGCCTGACCCACCTGCCTGACCCTTCCTCTAATGGTC
AACCCTCTCTATTCCAGCACACATTCCTGTTTC (SEQ ID NO:78)

FIG. 5(3)

rMOR-1B2 (1628 bp)

GTTACAGCCTACCTAGTCCGCAGCAGGCCTTCAGCACCATGGACAGCAGCACCGGCCCAGGGAACACCAGGACTGCT
CAGACCCCTTAGCTCAGGCAAGTTGCTCCCCAGGCTCTGCTCCAACTTGTCCCACGTTGATGGCAACCAGTC
CGATCCATGCGGTCTGAACCGGCACCGGGCTTGGCGGAACGACAGCTGTGCCCTCAGACGCAGCCTTCCATGGT
CACAGCCATTACCATCATGGCCCTCTACTCTGTGTGTGTAGTGGGCCTCTTCGGAAACTTCCTGGTCATGTATGTGA
TTGTAAGATACACCAAAATGAAGACTGCCACCAACATCTACATTTTCAACCTGGCAGACGCCTTAGCGACCAG
TACACTGCCCTTCAGAGTGTCAACTACCTGATGGGAACATGGCCCTTCGGAACATCCTCTGCAAGATCGTGATTTCA
ATAGATTACTACAACATGTTCACCAGCATATTCACCCTCTGCACCATGAGCGTGGACCGCTACATTGCTGTCTGCCACC
CAGTCAAGCCCTGGATTTCCGTACCCCGCAAATGCCAAATACAGGCAGGGTCATAGATTGCACCCTCACGTCTCCACCCA
CGGTCTGCCTGTAATGTTCATGGCAACCTCAAGTCAAGAGCGTTCGCATGCTATCGGGCTGCGTATTATCGTCTGCTGGA
ACCTGGTACTGGGAGAACTCGATCTTACGACTCAGAAACCACATTTCCTGGATGAAAACTTCAAGGACATGTCTTGGTTACACGAACAGCT
GATCACCCGGATGGTCGTGGTGTCCAGAGAACCACATTTCCTGGATGAAAACTTCAAGGACATGTCTTGCATCCAACCTC
GCGCTGATCACGAGTTCTTTTACGCCTTCATCATGCCTGTCGTCGGGGATGTCAAGAGAGGTCTGCATCCAACCTC
GTCCAACTAACCACCAGGAGCCTCAGTAGAGAGCTCAGTGAGTTACTAGAGGAACATCCCTCCACGTGATTAAACAAGGTTTCTGAAC
TCGAACTAACCACCAACACAACAAAATGTAGAGTTACTAGAGGTTACTAGAGAGATTTTATTTCATGACTAACAACATGACCCAAAGCACCCTAAACTGTGGT
ACTGAAATACAACACAACAAATGTAGAGGTTACTAGAGAGATTTTATTTCATGACTAACAACATGACCCAAAGCACCTAAACTGTGGT
GTGAGTGTATACATTTTAAGGCCTCAGAGAGAGCCTGGACTAAAGATGAGAAAGATGAGGAAAGACTGAAATATTTCATATCTTCCTGTGAACTC
GATTAGAGTTACAAAGACAATTCTAGAGCCTGGACTAAAGATGAGAAAGACTGAAATATTTCATATCTTCCTGTGAACTC
TAATGGAATGAGCAAATTAGATTAGTGAGAAAGATGGAGAAAGACTGAAATATTTCATATCTTCCTGTGAACTC
CACAAGAAAACCAATAGAATAAACCAACCTGCTGACCCTTGGTGGCTCTTACC (SEQ ID NO:79)

rMOR-1B2 (394 aa)

MDSSTGPGNTSDCSDPLAQASCSPAPGSWLNLSHVDGNQSDPCGLNRTGLGGNDSLCPQTGSPSMVTAITIMALYSIVCVVG
LFGNFLVMYVIVRYTKMKTATNIYIFNLALADALATSTLPFQSVNYLMGITWPFGTILCKIVISIDYYNMFTSIFTLCTMSVDRY
IAVCHPVKALDFRTPRNAKIVNVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALITIPETFQTVSWHFCIALGYTNSCLNPVL
LRLPGMKTSSDASEEFCIPTSSTIEQQNSTRVRQNTREHPSTANTVDRTNHQEPQSVET (SEQ ID NO:80)

FIG. 6A rMOR-1C1 (1433 bp)

GTTACAGCCTACCTAGTCCGCAGCAGGCCTTCAGCACCATGGACAGCAGCACCGGCCCAGGAACACCAGCGACTGCT
CAGACCCCTTAGCTCAGGCAAGTTGCTCCCCAGCACCTGGCTCCTGCTCAACTGTCCACGTTGATGGCAACCAGTC
CGATCCATGCGGTCTGAACCGGCTTGGGCGGAACGACAGCCTGTGCCCTCAGACCGGCAGCCCTTCCATGGT
CACAGCCATTACCATCATGGCCCTCTACTCTATCGTGTGTGTAGTGGGCCTCTTCGGCAAACTTCCTGTCATGTATGTGA
TTGTAAGATACACCAACAAATGAAGACTGCCACCAACATCTACATTTCAACCTTGCTCTGGCAGACGCCTTAGGACCAG
TACACTGCCCTTTCAGAGTGTCAACTACCTGATGGGAACATGCCCCTCTGCAACCATCCTCTGCAAGATCGTGATCTCA
ATAGATTACTACAACATGTTCACCAGCATATTCACCCTCTGCACCATGAGCGTGGACCGCTACATTGCTGTCTGCCACC
CAGTCAAAGCCCTGGATTTCAGGATTACCCCCGCAACACAAATACAGGCAGGGTCCATAGATTGCACCCTCACGTTCTCCCACCA
CGGTCTGCCTGTAATGTTCATGGCAACCTGCTCAAAATCTGTGTCTTTATCTTCGCTTTCATGATTCCTGTCCTGACTGTG
ACCTGGTACTGGGAGAATCTTACGACTCAAGAGCGTTCGCATGCTATCGTCTGCTGACCATTCCTGGCACTTGCTTTGGGTTACGAACAGCT
TTACGGCCTGATGATCATCAGAACCACATTCCAGAACCGTTCCTGGCACTTCAGAGGATGCTTCATCCAACCTCGTCC
GCCTGAATCCAGTTCTTTACGCCTTCCTGGATGAAAACTTCAAGCGATGCTTCAGAGAGTTCTGCATCCCAACCTCGTCC
ACGATGAACAGCAAAACTCCACTGAGTCCGTCAGCCCTGGCAGTCCAGGACAACATCCCTCCAGGCTAATACAGTGGATCGA
ACTAACCACCAGGACGTTACAGGACAGACCTAGACCCTGAATCGCGTGCAGAATCCAATGTGG
CCTGCAAGAGTTACAGGACAGACCGGCATTAATCTATAACAATGTGAATTTCATCTATAAACACAGGATGTGCTAGTGAGAAGTT
TGGAGGTGCAGGC (SEQ ID NO:81)

rMOR-1C1 (451 aa)

MDSSTGPGNTSDCSDPLAQASCSPAPGSWLNLSHVDGNQSDPCGLNRTGLGGNDSLCPQTGSPSMVTAITIMALYSIVCVVG
LFGNFLVMYVIVRYTKMKTATNIYIFNLALADALATSTILPFQSVNYLMGTWPFGTILCKIVISIDYYNMFTSIFTLCTMSVDRY
IAVCHPVKALDFRTPRNAKIVNVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALITPETTFQTVSWHFCIALGYTNSCLNPVL
YAFLDENFKRCFREFCIPTSSTEQQNSTRVRQNTREHPSTANTVDRTNHQPALAVSVAQIFTGYPSPTHGEKPCKSYRDRPRP
CGRTWSLKSRAESNVEHFHCGAALIYNNVNFI (SEQ ID NO:82)

FIG. 6B rMOR-1C2 (1480 bp)

GTTACAGCCTACCTAGTCCGCAGCAGGCCTTCAGCACCATGGACAGCAGCACCGGCCCCAGGGAACACCAGGACTGCT
CAGACCCCTTAGCTCAGGCAAGTTGCTCCCCAGGGCTCCTGGCTCCTGTCCCACGTTGATGGCAACCAGTC
CGATCCATGGGTCTGAACCGCACCGGGCTTGGGCGAACGACAGCCTGTGCCCTCAGACCGGCAGCCCTTCCATGGT
CACAGCCATTACCACCATGGCCCTCTATCGTGTGTGTAGTGGGCCTCTGGCCTTCAACTTGCTCTGGCAGACGCCTTAGCGACCAG
TGTAAGATACACCAAAATGAAGACTGCAGTGTCAACTACCAGCATATTCACCTGGAACATGGCCCTTCGGAACCATCCTGCAAGATCGTGATCTCA
TACACTGCCCTTTCAGAGTGTCAACTACCAGCATATTCACCCTGCAACCTCTGCAACCATGAGCGTGGAACCGCTACATGCTGTCTGCCACC
ATAGATTACTACAACATGTTCACCAGCATATTCACCCTGCAACCTCTGCAACCATGAGCGTGGAACCGCTACATGCTGTCTGCCACC
CAGTCAAGCCCTGTAAGTGTCATGGCAACCACAAATCTGTCTTTATCTCGCTTCATCGCCGGTCATCATCACTGTGTG
CGGTCTGCCTGTAAGTGTCATGGCAACCACAAATCTGTCTTTATCTCGCTTCATCGCCGGTCATCATCACTGTGTG
ACCTGGTACTGGGAGAATCTTACGACTCAAGAGCGTTCGCATGCTATCGTCTGTCGGACACTTCGGGAAGGACGAATCTGCGCAG
TTACGGCCTGATGATCTTACGACTCAAGAGCGTTCGCATGCTATCGTCTGTCGGACACTTCGGGAAGGACGAATCTGCGCAG
GATCACCCGGATGGTGCGATTCCAGAAACCACATTCAGACCGTTCCTGGCACTTCTGCATTGCTTTGGGTTACAGAACAGT
GCGCTGATCACGATTCCAGAAACCACATTCAGACCGTTCCTGGCACTTCTGCATCCCAACCTCGTCC
GCCTGAATCGAACAGCAAAACTCCACTGCGAGTCGTCAGAACACTAGGGAACATCCCTCCACGGCTAATACAGTGGATCGA
ACGATGAACAGCAAAACTCCACTGCGAGTCGTCAGAACACTAGGGAACATCCCTCCACGGCTAATACAGTGGATCGA
ACTAACCACCAGCCAGCCCTGGACAGAGACCTAGAACGGCATTAATCTATAAACAATGAAACTAAAAATAGGGCCAGTGTCCTGGCTCCAGATGCCTGC
CCTGCAAGAGTTACAGGGACAGAGACCTAGAACGGCATTAATCTATAAACAATGAAACTAAAAATAGGGCCAGTGTCCTGGCTCCAGATGCCTGC
AGCACTTCCATTGTGGAGCCCCCTGGTAATGAACACGGGCTCCGATTCTGAATATCCTTCTGTG (SEQ ID NO:83)
GCACGGTGCGTGCGCCCCCTGGTAATGAACACGGGCTCCGATTCTGAATATCCTTCTGTG (SEQ ID NO:83)

rMOR-1C2 (468 aa)

MDSSTGPGNTSDCSDPLAQASCSPAPGSWLNLSHVDGNQSDPCGLNRTGLGGNDSLCPQTGSPSMVTAITIMALYSIVCVVG
LFGNFLVMYVIVRYTKMKTATNIYFNLALADALATSTLPFQSVNYLMGTWPFGTILCKIVISIDYYNMFTSIFTLCTMSVDRY
IAVCHPVKALDFRTPRNAKIVNVCNWILSSAIGLPVMFMATTKYRQGSIDCTLTFSHPTWYWENLLKICVFIFAFIMPVLIITV
CYGLMILRLKSVRMLSGSKEKDRNLRRITRMVLVVVAVFIVCWTPIHIYVIIKALITPETTFQTVSWHFCIALGYTNSCLNPVL
YAFLDENFKRCFREFCIPTSSTIEQQNSTRVRQNTREHPSTANTVDRTNHQPALAVSVAQIFTGYPSPTHGEKPCKSYRDRPRP
CGRTWSLKSRAESNVEHFHCGAALIYNNELKIGPVSWLQMPAHVLVRPW (SEQ ID NO:84)

FIG. 6C rMOR-1D (1385 bp)

GCCTACCTAGTCCGCAGCAGGCCTTCAGCACCATGGACAGCAGCACCGGCCCAGGGAACACCAGCGACTGTCAGACC
CCTTAGCTCAGGCAAGTTGCTCCCCAGCACCACCTGGCTCCTGGCTCAACTTGTCCCACGTTGATGGCAACCAGTCCGATCC
ATGCGGTCTGAACCGCACGGGCTTGGCGGGAACGACAGCCTGTGCCCTCAGACGCCAGCCCTTCCATGGTCACAGC
CATTACCATCATGGCCCTCTACTCTATCGTGTGTGTAGTGGACATCTACATTTTCAACCTTGCTCTGGCAGACGCCTTAGGGACCAGTACACT
GATACACCAAAATGAAGACTGCCAACTACCTGATGGGAACATGCCCCTTCGAACCATCCTGCCAAGATCGTGATCTCAATAGAT
GCCCTTTCAGAGTGTCAACTACCTGATGGGAACATGGGAACATGCCCCTTCGAACCATCCTGCCAAGATCGTGATCTCAATAGAT
TACTACAACATGTTCACCAGCATATTCACCCTCTGCACCATGAGCGTGGACCGTACCATTGCTGTCTGCCACCAGTCA
AAGCCCTGGATTTCCGTACCCCCGCAACCACAAATGCCAAAATCGTCAACTGTCAACTGTCCATCCTCTCTTCTGCCATCGGTCT
GCCTGTAATGTTCATGGCAACCTGCTCTCAAAATCTGTGTCTTGTCTTTCGCTATCATGCCGTTCATGATCAGGACAGGGTCCATAGATTGCACCCTCACGTTCTCCCACCTGG
TACTGGGAGAACCTTCTACGACTTAAGAGCGTTCGCATCGAGCGTTGTGATTATCGTCGGTGCTGTCGGTCTGGAACCATTCAGAGACAGGAATCTGCGCAGGATCAC
CGGATGGTGCGAAACCATTTCAGAACCGTTCCTGCAGTTCCTGCACTTCTGAAGCAGCGCGGTATAGGAAGGCGCTG
ATCACGATTCCAGAAACCATTTCAGAACCGTTCCTGCAGTTCCTGCACTTCTGAAGCAGCGCGGTATAGGAAGGCGCTG
ATCCAGTTCTTTACGCCTTCCTGATGAAAACTTCAAGCCGATGCTTCAAGAGAGTTCTGCATCCAACCTGCTCGTCCACGATC
GAACAGCAAAACTCCACTGCAGTCCGTCAGAACACTAGGGAACATCCCTCCACGGCTAATACAGTGGATCGAACTAAC
CACCAGACTCAGACCCTGTGGAAGAACGTGGTCTTGAAATGCGGTCGAGAATCCAATGTGGAGCACTTCCATTGTGGA
GCGCATTAATCTATAAACAATGAAGACTAAAAATAGGGCCAGTGCCTCCAGATGCCTGGCCACGTGCTGTCGTGCGCC
CCTGGTAATGAACACGGGCTCCGATTCTGAATATCCTTCTGTG (SEQ ID NO:85)

rMOR-1D (387 aa)

MDSSTGPGNTSDCSDPLAQASCSPAPGSWLNLSHVDGNQSDPCGLNRTGLGGNDSLCPQTGSPSMVTAITIMALYSIVCVVG
LFGNFLVMYIVRYTKMKTATNIYIFNLALADALATSTLPFQSVNYLMGTWPFGTILCKIVISIDYNMFTSIFTLCTMSVDRY
IAVCHPVKALDFRTPRNAKIVNVCNWILSSAIGLPVMFMATTKYRQGSIDCILTFSHPTWYWENLLKICVFVFAFIMPVLIITV
CYGLMILRLKSVRMLSGSKEKDRNLRITRMVLVVVAVFIVCWTPIHIYVIKALITPETFQTVSWHFCIALGYTNSCLNPVL
YAFLDENFKRCFREFCIPTSSTIEQQNSTRVRQNTREHPSTANTVDRITNHQT (SEQ ID NO:86)

FIG. 6D rMOR-1E (2078 bp)

GTTACAGCCTACCTAGTCCGCAGCAGGCCTTCAGCACCACCATGGACAGCAGCACCGGCCCAGGGAACACCAGCGACTGCT
CAGACCCCTTAGCTCAGGCAAGTTGCTCCCCAGCAGTTGTCCCACGTTGATGGCAACCAGTC
CGATCCATGCGGTCTGAACCGCACCGGGCTGGCCGGAACGACAGCCTGTGCCCTCAGACCGGCAGCCTTCCATGGT
CACAGCCATTACCATCATGCCCTCTACTCTATGCCACCAACATCTACATTTCAACCTTGTCTGCAGACGCTTAGCGACCAG
TTGTAAGATACACCCAAAATGAAGACTGCCACCAACTGATGGGAACATGGCCCTTCGGAACATCCTCTGCAAGATGTGATCTCA
TACACTGCCCTTTCAGAGTGTCAACTGATGTGTCACCAGCATATTCACCCCTGCACGAGCGTGGACCGCTACATTGCTGTGTCTGCCACC
ATAGATTACTACAACATGTTCACCAGCATATTCACCCCTGCACGAGCGTGGACCGCTACATTGCTGTGTCTGCCACC
CAGTCAAAGCCCTGATTTCCGTACCCCGAAAATGCCAAAATCGTCAACGTCTGCAACTGGATCCTCTCTCTGCCAT
CGGTCTGCCTGTAATGTTCATGCAACCAGAACCTGCTCAAATCTGTCTTTATCTTCGGCTCCAAGAGGCGCTCCAACCA
ACCTGGTACTGGGAGAGATCTTACGACTCAAGAGCGTTCATCATGCGGTCCTCATCATCACTGTGTG
TTACGGCCTGATGATGATCTTCCAGAAACCACATTTCAGACCGTTCCTGGCACTCTGCATTGCTTGGGTTACACGAACAGCT
GCGCTGATCACGATCCAGAATTCCAGTTCTTTTACGCCTTCTCTGGATGAAACTTCAAGCATCTCACCAACCTCGTCC
GCCTGAATCACGAGTTCTTTTACGCCTTCTCTGGATGAAACTTCAAGCATGTCTCAGAGAGTTCTGCATCCAACCTCGTCC
ACGATCGAACAGCAAACTCCAGTCGAGTCCGTCAGAACACTAGGGAACATCCCTCCAGCGCTAATACAGTGGATCGA
ACTAACCACCAGGAGCAGAGTTATGAGGATGCCCCATCTTATTCAGTCTTTCTGACTGACCTCTCCACTCTCTCACTGTTCCCTTGTTTTCA
GGGCCCTGGCCCCACAATGGTAGGGCTCTCCCACTCTTTATTCAGTCTTTCTGACTGACCTCTAATGCAATACACGTGAGCCAACACCCCAGAGAG
GCTATGGCTACCCGGCATAGCTCATACCGAAGTGGGAAGTGTGCCAAGGCTCAATACAACTAGATGGATCCGC
CTCAGGAGACAGGAATGGCGGCAGAGAATCCCCCCACTCAAAGGCAAGCAATTATTAACAAATTTATCTCCTGCTTCCAGCTCAGA
CATGGTGGTAATGGCGGCAGAGAATCCCCCCACTCAAAGGCAAGCAATTATTAACAAATTTATCTCCTGCTTCCAGCTCAGA
AATCAGCCAGAGACAGATCACAACACATAAGCAGCCCTTTTCTACTTTCTCTTCTTTCAACTCTCGCCTGC
CATTGTTATCCACATCAACACACATAAGCAGCCCTTTTCTACTTTCTCTTCTTTCTTTCAACTCTCGCCTGC
ACTTTGAAAGGGTAAGGATTTAAATTGATTTTTTCTCTTTGGCATTTAAATATTTGCTTTCATTGGAGAAAGGAAGAGCATA
TGAAACTATCTATACAAACTGAGCTTCAAATCTTTGGCATTTAAATATTTGCTTTCATTGGAGAAAGGAAGAGCATA
GGAAAGCTTGGCTTCCTCCCTCCCAGGTCCTTGTCTTCCCCTAGGTCCTTGTCTTCCCCAGGCTGTAGGGTGTGGCTGCTTG
GTAGCTTCCTCTAGGACACTGTTGGGCCTTCTTATCCTGCCTGACCCACCTGACCTTCCTCCTAATGGTCAACCTCTCTATT
CCAGCACATTCCTGTTTC (SEQ ID NO:87)

FIG. 6E(1)

rMOR-1E (390 aa)

MDSSTGPGNTSDCSDPLAQASCSPAPGSWLNLSHVDGNQSDPCGLNRTGLGGNDSLCPQTGSPSMVTAITIMALYSIVCVVG
LFGNFLVMYVIVRYTKMKTATNIYIFNLALADALATSTLPFQSVNYLMGTWPFGTILCKIVISIDYYNMFTSIFTLCTMSVDRY
IAVCHPVKALDFRTPRNAKIVNVCNWILSSAIGLPVMFMATTKYRQGSIDCTLTFSHPTWYWENLLKICVFIFAFIMPVLIITV
CYGLMILRLKSVRMLSGSKEKDRNLRGITRMVLVVVAVFIVCWTPIHIYVIIKALITIPETTFQTVSWHFCIALGYTNSCLNPVL
YAFLDENFKRCFREFCIPTSSTIEQQNSTRVRQNTREHPSTANTVDRTNHQGAEL (SEQ ID NO:88)

FIG. 6E(2)

MU OPIOID RECEPTOR SPLICE VARIANT POLYPEPTIDES, POLYNUCLEOTIDES AND METHODS OF SCREENING COMPOSITIONS

RELATED APPLICATIONS/PATENTS & INCORPORATION BY REFERENCE

This application is filed under 35 U.S.C. § 371 as the U.S. national phase application of International Application PCT/US05/04548, having an international filing date of Feb. 11, 2005 and designating the U.S. and claiming priority to U.S. Provisional Application Ser. No. 60/544,534, filed on Feb. 13, 2004, the contents of which are incorporated herein by reference. Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein cited references"), as well as each document or reference cited in each of the herein-cited references (including any manufacturer's specifications, instructions, etc.), is hereby expressly incorporated herein by reference.

STATEMENT OF RIGHTS TO INVENTION MADE UNDER FEDERALLY SPONSORED RESEARCH

This work was supported by the government, in part, by grants from the National Institute on Drug Abuse (DA02615 and DA07241); a Senior Scientist Award (DA00220) to Gavril W. Pasternak; a research grant (DA13997) to Ying-Xian Pan; a grant from the National Genetics Foundation; and a core grant to Memorial Sloan-Kettering Cancer Center, New York, N.Y. (CA08748) from the National Cancer Institute. The government may have certain rights to this invention.

TECHNICAL FIELD

The present invention relates to mu-opioid receptor-1 (MOR-1) splice variant polypeptides, to DNA sequences encoding the splice variants, to DNA sequences encompassing non-coding region splice variants, to methods of screening compositions for agonists and antagonists of the splice variant receptor activities and to methods of measuring splice variant binding activities.

BACKGROUND ART

Opiates are drugs derived from opium and include morphine, codeine and a wide variety of semisynthetic opioid congeners derived from them and from thebaine, another component of opium. Opioids include the opiates and all agonists and antagonists with morphine-like activity and naturally occurring endogenous and synthetic opioid peptides. Morphine and other morphine-like opioid agonists are commonly used pharmaceutically to produce analgesia.

There are now many compounds with pharmacological properties similar to those produced by morphine, but none has proven to be clinically superior in relieving pain. References to morphine herein will be understood to include morphine-like agonists as well. The effects of morphine on human beings are relatively diverse and include analgesia, drowsiness, changes in mood, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. For instance, the typical initial dose of morphine (10 mg/70 kg) relieves post-operative pain satisfactorily in only two-thirds of patients. Likewise, responses of an individual patient may vary dramatically with different morphine-like drugs and patients may have side effects with one such drug and not another. For example, it is known that some patients who are unable to tolerate morphine may have no problems with an equianalgesic dose of methadone. The mechanisms underlying variations in individual responses to morphine and morphine-like agonists have not been defined.

The analgesic effects of morphine are transduced through opioid receptors in the central nervous system (CNS), located at both spinal and multiple supraspinal sites. Morphine and other agonists induce profound analgesia when administered intrathecally or instilled locally into the dorsal horn of the spinal cord. Several mechanisms of action are believed to mediate the inhibition of nociceptive reflexes from reaching higher centers of the brain, including the inhibition of neurotransmitter release by opioid receptors on the termini of primary afferent nerves and post synaptic inhibitory actions on interneurons and on the out-put neurons of the spinothalamic tract.

Profound analgesia can also be produced by the instillation of morphine into the third ventricle or within various sites in the midbrain and medulla, most notably the periaqueductal gray matter, the nucleus raphe magnus, and the locus ceruleus. Although the neuronal circuitry responsible has not been defined, these actions produce enhanced activity in the descending aminergic bulbospinal pathways that exert inhibitory effects on the processing of nociceptive information in the spinal cord. Simultaneous administration of morphine at both spinal and supraspinal sites results in a synergized analgesic response, with a ten-fold reduction in the total dose of morphine necessary to produce equivalent analgesia at either site alone.

Morphine also exerts effects on the neuroendocrine system. Morphine acts in the hypothalamus to inhibit the release of gonadotropin releasing hormone (GnRH) and corticotropin-releasing factor (CRF), thus decreasing circulating concentrations of luteinizing hormone (LH), follicle stimulating hormone (FSH), and adrenocorticotropin (ACTH), and β-endorphin. As a result of the decreased concentrations of pituitary trophic hormones, the concentrations of testosterone and cortisol in the plasma decline. The administration of opiates increases the concentration of prolactin (PRL) in plasma, most likely by reducing the dopaminergic inhibition of PRL secretion. With chronic administration, tolerance eventually develops to the effects of morphine on hypothalamic releasing factors.

Opiates can interfere with normal gastrointestinal functioning. Morphine decreases both gastric motility and the secretion of hydrochloric acid in the stomach. Morphine may delay passage of gastric contents through the duodenum for as long as 12 hours. Morphine also decreases biliary, pancreatic and intestinal secretions and delays the digestion of food in the small intestine. Propulsive peristaltic waves in the colon are diminished or abolished after administration of morphine and commonly, constipation occurs. For a detailed review of the physiological effects of morphine, see Reisine and Pasternak (1996) Goodman & Gilman's The pharmacological basis of therapeutics, Ninth Edition (Hardman et al. eds.) McGraw-Hill pp. 521-555.

Morphine also exerts effects on the immune system. The most firmly established effect of morphine is its ability to inhibit the formation of rosettes by human lymphocytes. The administration of morphine to animals causes suppression of the cytotoxic activity of natural killer cells and enhances the growth of implanted tumors. These effects appear to be mediated by actions within the CNS. By contrast, β-endorphin enhances the cytotoxic activity of human monocytes in vitro and increases the recruitment of precursor cells into the killer cell population; this peptide also can exert a potent chemotactic effect on these cells. A novel type of receptor (designated ε) may be involved. These effects, combined with the synthesis of Proopiomelanocortin (POMC) and preproenkephalin by various cells of the immune system, have stimulated studies of the potential role of opioids in the regulation of immune function. Sibing a and Goldstein (1988) Annu. Rev. Immunol. 6:219.

Side effects resulting from the use of morphine range from mild to life threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and an inhibition of baroreceptor reflexes in the cardiovascular system. Additionally, morphine provokes the release of histamines, which can cause hypotension. Morphine depresses respiration, at least in part by direct effects on the brainstem regulatory systems. In humans, death from morphine poisoning is nearly always due to respiratory arrest. Opioid antagonists can produce a dramatic reversal of severe respiratory depression and naloxone is currently the treatment of choice. High doses of morphine and related opioids can produce convulsions that are not always relieved by naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; and Elliott et al. (1994) Pain 56:69. Blockade of the glycine regulatory site on NMDA receptors has similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. U.S.A. 90:5162. These studies indicate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists and/or antagonists, tolerance and dependence in the clinical management of pain can be minimized or disassociated from the therapeutic effects.

In addition to morphine, there are a variety of opioids suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine. The pharmacological effects of levorphanol closely parallel those of morphine although clinical reports suggest that levorphanol produces less nausea.

Meperidine exerts its chief pharmacological effects on the central nervous system and the neural elements in the bowel. Meperidine produces a pattern of effects similar but not identical to those described for morphine. In equianalgesic doses, meperidine produces as much sedation, respiratory depression, and euphoria as morphine. The pattern of unwanted side effects that follow the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacological properties similar to morphine. The properties of methadone include effective analgesic activity, efficacy by the oral route and persistent effects with repeated administration. Side effects include detection of miotic and respiratory-depressant effects for more than 24 hours after a single dose, and marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, and the analgesic effect of codeine is due to its conversion to morphine. However, codeine's antitussive actions probably involve distinct receptors that bind codeine specifically.

Propoxyphene produces analgesia and other CNS effects that are similar to those seen with morphine. It is likely that at equianalgesic doses the incidence of side effects such as nausea, anorexia, constipation, abdominal pain, and drowsiness would be similar to those of codeine.

Opioid antagonists have therapeutic utility in the treatment of overdosage with opioids. As understanding of the role of endogenous opioid systems in pathophysiological states increases, additional therapeutic indications for these antagonists will emerge. If endogenous opioid systems have not been activated, the pharmacological actions of opioid antagonists depend on whether or not an opioid agonist has been administered previously, the pharmacological profile of that opioid and the degree to which physical dependence on an opioid has developed. The antagonist naloxone produces no discernible subjective effects aside from slight drowsiness. Naltrexone functions similarly, but with higher oral efficacy and a longer duration of action. Currently, naloxone and naltrexone are used clinically to treat opioid overdoses. Their potential utility in the treatment of shock, stroke, spinal cord and brain trauma, and other disorders that may involve mobilization of endogenous opioids remains to be established.

The complex interactions of morphine and drugs with mixed agonist/antagonist properties are mediated by multiple classes of opioid receptors. Opioid receptors comprise a family of cell surface proteins, which control a range of biological responses, including pain perception, modulation of affective behavior and motor control, autonomic nervous system regulation and neuroendocrinological function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Morphine produces analgesia primarily through the mu-opioid receptor. However, among the opioid receptors, there is substantial overlap of function as well as of cellular distribution.

The mu-opioid receptor mediates the actions of morphine and morphine-like opioids, including most clinical analgesics. In addition to morphine, several highly selective agonists have been developed for mu-opioid receptors, including [D-Ala$^2$,MePhe$^4$,Gly(ol)$^5$]enkephalin (DAMGO), levorphanol and methadone. Differential sensitivity to antagonists, such as naloxonazine, indicates the pharmacological distinctions between the mu-opioid receptor subtypes, $mu_1$ and $mu_2$. Several of the opioid peptides will also interact with mu-opioid receptors.

There are three distinct families of endogenous opioid peptides, the enkephalins, endorphins and dynorphins, where each peptide is derived from a distinct precursor polypeptide. Mu-opioid receptors have a high affinity for the enkephalins as well as β-endorphin and dynorphin A. For review, see Reisine and Pasternak (1996).

Members of each known class of opioid receptor have been cloned from human cDNA and their predicted amino acid sequences have been determined. Yasuda et al. (1993) Proc. Natl. Acad. Sci. U.S.A. 90:6736; and Chen et al. (1993) Mol. Pharmacol. 44:8. The opioid receptors belong to a class of transmembrane spanning receptors known as G-protein coupled receptors. G-proteins consist of three tightly associated subunits, alpha, beta and gamma (1:1:1) in order of decreasing mass. Following agonist binding to the receptor, a conformational change is transmitted to the G-protein, which causes the G-alpha subunit to exchange a bound GDP for GTP and to dissociate from the beta and gamma subunits. The GTP-bound form of the alpha subunit is typically the effector-modulating moiety. Signal amplification results from the ability of a single receptor to activate many G-protein molecules, and from the stimulation by G-alpha-GTP of many catalytic cycles of the effector.

Most opioid receptor-mediated functions appear to be mediated through G-protein interactions. Standifer and Pasternak (1997) Cell Signal. 9:237. Antisense oligodeoxynucleotides directed against various G-protein alpha subunits were shown to differentially block the analgesic actions of the mu-, delta-, and kappa-opioid agonists in mice. Standifer et al. (1996) Mol. Pharmacol. 50:293.

The amino acid sequences of the opioid receptors are approximately 65% identical, and they have little sequence similarity to other G-protein-coupled receptors except for somatostatin. Reisine and Bell (1993) Trends Neurosci. 16:506. The regions of highest similarity in sequence are the sequences predicted to lie in the seven transmembrane-spanning regions and the intracellular loops. Regions of amino acid sequence divergence are the amino and carboxy termini and the second and third extracellular loops.

Each receptor subtype has a characteristic pattern of expression. Mu-opioid receptor mRNA is present in the periaqueductal gray, spinal trigeminal nucleus, cuneate and gracile nuclei, and thalamus regions of the brain involved in pain perception and associated with morphine analgesia. Defts et al. (1994) J. Comp. Neurol. 345:46. It is also present in nuclei involved in control of respiration, consistent with the ability of morphine to depress respiration, and in neurons of the area postrema, where morphine has been shown to cause nausea and induce vomiting. Other consequences of mu-opioid receptor activation include miosis, reduced gastrointestinal motility, and feelings of well-being or euphoria. Pasternak (1993). The pattern of mu-opioid receptor mRNA expression correlates with the brain centers involved in mediating the biological actions of morphine and mu-selective agonists. Delta-opioid receptor mRNA is found in the dorsal horn of the spinal cord. $Kappa_1$-opioid receptor mRNA is expressed in the hypothalamic regions, which may account for many of the neuroendocrine effects of the kappa selective agonists.

Soon after the mu-opioid receptor MOR-1 was cloned (Chen et al. (1993); and Wang et al. (1993) Proc. Natl. Acad. Sci. U.S.A. 90:10230), antisense experiments confirmed its involvement with morphine analgesia. Rossi et al. (1994) Life Sci. 54:375; and Rossi et al. (1995) FEBS Lett. 369:192. Antisense oligonucleotides directed against MOR-1 mRNA blocked the analgesic actions of morphine in rats, demonstrating that proper translation of the MOR-1 mRNA was essential for modulating morphine analgesia. Antisense approaches have also demonstrated a relationship between MOR-1 activity and ingestive responses. Administration of antisense oligonucleotides directed against MOR-1 mRNA significantly reduced food and water intake and subsequently, body weight in rats.

In recent years, a number of mu-opioid receptor subtypes have been proposed. The first suggestion of $mu_1$ and $mu_2$ receptor subtypes came from a combination of binding and pharmacological studies based on the antagonists naloxonazine and naloxazone. Wolozin and Pasternak (1981) Proc. Natl. Acad. Sci. U.S.A. 78:6181; Reisine and Pasternak (1996); and Pasternak (1993). A gene encoding a mu receptor, MOR-1, has been identified. Min et al. (1994) Proc. Natl. Acad. Sci. U.S.A. 91:9081; Giros et al. (1995) Life Sci. 56:PL369; and Liang et al. (1995) Brain Res. 679:82. The MOR-1 cDNA consists of exons 1-4, which total 1610 bp in length and encode 398 amino acids. More recently, pharmacological and molecular differences between morphine and morphine-6β-glucuronide (M6G) have suggested yet another mu-opioid receptor subtype. Pasternak and Standifer (1995) Trends Pharmacol. Sci. 16:344; Rossi et al. (1995); and Rossi et al. (1996) Neurosci. Lett. 216:1.

Antisense oligonucleotides directed against selected exons within the MOR-1 mRNA revealed interesting therapeutic patterns of morphine and M6G analgesia, with some MOR-1 exons implicated in the analgesic actions of one drug, but not the other. Rossi et al. (1997) J. Pharmacol. Exp. Ther. 281: 109; and Rossi et al. (1995). Although the two analgesics were known to act through different receptors, the sensitivity of the effect of both analgesics to at least six different MOR-1 antisense probes implied that both receptors were closely associated with MOR-1, raising the possibility of pharmacologically relevant MOR-1 splice variants. Pasternak and Standifer (1995); and Rossi et al. (1995). Alternative splicing has been observed with a number of G-protein-coupled receptors, including somatostatin 2 (Vanetti et al. (1998) FEBS Lett. 311:290), dopamine D2 (Guiramand et al. (1995) J. Biol. Chem. 270:7354), prostaglandin EP3 (Namba et al. (1993) Trends Pharmacol. Sci. 16:246), serotonin receptor subtypes 5-HT$_4$ and 5-HT$_7$ (Lucas and Hen. (1995) Trends Pharmacol. Sci. 16:246) and MOR-1 (Bare et al. (1994) FEBS Lett. 354:213; and Zimprich et al. (1995) FEBS Lett. 359:142).

Several opioid receptor splice variants have been identified and characterized. At least two MOR-1 splice variants are known, the human MOR-1A and the rat MOR-1B. Bare et al. (1994); and Zimprich et al. (1995). The hMOR-1A splice variant consists of exons 1, 2, 3 and a new exon 3a, and was determined to possess ligand binding characteristics similar to the full-length MOR-1. Bare et al. (1994). The rMOR-1B splice variant consists of exons 1, 2, 3 and a new exon 5, and like hMOR-1A, differs from MOR-1 only in length and amino acid composition at the carboxy-terminal tail. Zimprich et al. (1995). MOR-1B has affinity to opioid compounds similar to that of MOR-1, but is much more resistant to agonist-induced desensitization than MOR-1. The C-terminal differences between MOR-1 and MOR-1A or MOR-1B could have effects on receptor coupling or receptor transport and localization. About twenty splice variants of the mouse MOR-1 gene (comprised of nine exons) have been identified and characterized. (see, e.g., PCT/US99/15974, published as WO 00/04046 and PCT/US02/20665, published as WO 03/002718 A2). The MOR-1 splice variants are potential targets for the modulation of physiological effects resulting from mu-opioid receptor activity. In addition, five splice variants of the kappa3-related opioid receptor (i.e., opioid receptor-like receptor (ORL-1), OFQ receptor or nociceptin receptor) have been identified and characterized, suggesting an analogous system of modulation to that of the mu class of receptors. (PCT/US99/15977, published as WO 00/04151). Splice variants that were under control of two distinct promoters in the mouse Oprm gene have been reported (see, e.g., Pan et al. (1999) Molecular Pharmacology 56, 396-403, Pan et al. (2000) FEBS Letters 466, 337-340, Pan et al. (2002) Gene 295, 97-108 and Pan et al. (2001) Proc. Natl. Acad. Sci. U.S.A 98, 14084-14089). Two additional human MOR-1 splice variants, hMOR-1O and hMOR-1X (see, e.g., Pan et al. (2003) Biochem Biophys Res Commun. 301, 1057-1061), have also been identified.

Availability of polynucleotide sequences of opioid receptor splice variants, and, in the case of splice variants in coding regions, the corresponding polypeptide sequences, will significantly increase the capability to design pharmaceutical compositions, such as analgesics, with enhanced specificity of function. In general, the availability of these polynucleotide and polypeptide sequences will enable efficient screening of candidate compositions. The principle in operation through the screening process is straightforward: natural agonists and antagonists bind to cell-surface receptors and channels to produce physiological effects; certain other molecules can produce physiological effects and act as therapeutic pharmaceutical agents. Thus, the ability of candidate drugs to bind to opioid receptor splice variants can function as an extremely effective screening criterion for the selection of pharmaceutical compositions with desired functional efficacy and specificity.

DISCLOSURE OF THE INVENTION

The invention encompasses MOR-1 splice variant polypeptides or polypeptide fragments or homologs thereof retaining MOR-1 activity.

The invention further encompasses a MOR-1 splice variant polynucleotide, encoding MOR-1 splice variant polypeptides or polypeptide fragments or homologs thereof retaining MOR-1 activity, and noncoding mRNA splice variants and complementary strands thereto.

The invention further encompasses a polynucleotide, or a complementary strand thereto that hybridizes under stringent conditions, comprising at least 15 consecutive nucleotides of an MOR-1 splice variant polynucleotide where the polynucleotide contains promoter elements.

The invention further encompasses methods of screening compositions for an opioid activity by obtaining a control cell that does not express a recombinant or endogenous opioid receptor, obtaining a test cell that expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further encompasses methods of screening compositions for an opioid activity by obtaining a control polypeptide that is not a recombinant opioid receptor, obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid, and comparing the test polypeptide binding of the composition to that of the opioid, where determination of binding of the composition is expressed relative to that of the opioid.

The invention further encompasses methods of screening compositions for differential or selective opioid activity comprising obtaining a first and second test polypeptide that are MOR-1 splice variant polypeptide fragments and contacting each with a composition, measuring the binding affinity of the composition to the first and second test polypeptides and comparing the binding of the composition and the first test polypeptide to that of the second test polypeptide where differential activity is expressed as a ratio of the two binding affinities.

The invention further encompasses methods of screening compositions for a MOR-1 binding protein by obtaining a control cell that does not express a recombinant or endogenous opioid receptor, obtaining a test cell that expresses a recombinant MOR-1 splice variant polypeptide, contacting the control cell extract and test cell extract with the MOR-1 splice variant polypeptide and comparing the test cell extract binding to that of the control cell extract binding with the MOR-1 splice variant polypeptide of interest to identify a MOR-1 binding protein.

The invention further encompasses a method for regulating morphine analgesia in a subject by altering of MOR-1 splice variant polypeptide activity. Activity can be regulated by administering antigen binding fragments, agonists, antagonists, small molecule ligands, antisense nucleic acids or siRNA to a subject in an amount and for a duration sufficient to regulate morphine analgesia. The antigen binding fragment, agonist, antagonist, small molecule ligand, antisense nucleic acid or siRNA is directed to an MOR-1 splice variant polypeptide fragment or a homolog thereof or an MOR-1 splice variant mRNA. Morphine analgesia can also be regulated by homodimerization or homooligomerization among the MOR-1 splice variants and heterodimerization or heterooligomerization between the variants and other opioid or non-opioid receptors.

The invention further encompasses regulating opioid activity by administering a DNA plasmid vector containing an MOR-1 splice variant polynucleotide. The DNA plasmid vector thereby expresses an mRNA splice variant that may encode an MOR-1 polypeptide in a subject in an amount of and duration sufficient to regulate morphine analgesia. Activity can also be regulated by administering an antisense nucleic acid or siRNA complementary to an MOR-1 splice variant polynucleotide, thereby blocking gene expression in a subject in an amount and duration sufficient to regulate morphine analgesia. Opioid activity can also be regulated by homodimerization or homooligomerization among the MOR-1 splice variants and heterodimerization or heterooligomerization between the variants and other opioid or nonopioid receptors.

The invention further encompasses antigen-binding fragments specific for the MOR-1 splice variant polypeptides described herein.

BRIEF DESCRIPTION OF THE DRAWINGS

FIG. 1B shows the partial cDNA sequences of the variants with translated amino acid sequences. The complete cDNA and deduced amino acid sequences of hMOR-1A, hMOR-1B1, hMOR-1B2, hMOR-1B3, hMOR-1B4, hMOR-1B5, and hMOR-1Y have been deposited in the GenBank database (Accession numbers: AY225404, AY309001, AY309005, AY309006, AY309007, AY309008, and AY309009). The cAMP- and cGMP-dependent protein kinase phosphorylation sites, caseine kinase II phosphorylation sites, tyrosine kinase phosphorylation site and translation stop codon are indicated by #, @, & and * respectively.

FIG. 3A depicts the nucleotide sequence and amino acid sequence of hMOR-1B1.

FIG. 3B depicts the nucleotide sequence and amino acid sequence of hMOR-1B2.

FIG. 3C depicts the nucleotide sequence and amino acid sequence of hMOR-1B3.

FIG. 3D depicts the nucleotide sequence and amino acid sequence of hMOR-1B4.

FIG. 3E depicts the nucleotide sequence and amino acid sequence of hMOR-1B5.

FIG. 3F depicts the nucleotide sequence and amino acid sequence of hMOR-1Y.

FIG. 4 shows an alignment of the human MOR-1 amino acid sequences.

FIG. 5 shows the partial cDNA sequences of the variants with translated amino acid sequences. The stop codons are indicated by *. The complete cDNA and deduced amino acid sequences of rMOR-1A, rMOR-1C1, rMOR-1C2, rMOR-1D, rMOR-1B2 and rMOR-1E have been deposited in the GenBank database (Accession numbers. AY309000, AY225402, AY225403, AY309002, AY309003 and AY309004).

FIG. 6A depicts the nucleotide sequence and amino acid sequence of rMOR-1B2.

FIG. 6B depicts the nucleotide sequence and amino acid sequence of rMOR-1C1.

FIG. 6C depicts the nucleotide sequence and amino acid sequence of rMOR-1C2.

FIG. 6D depicts the nucleotide sequence and amino acid sequence of rMOR-1D.

FIG. 6E depicts the nucleotide sequence and amino acid sequence of rMOR-1E.

BEST MODE FOR CARRYING OUT THE INVENTION

Figure 1A:
FIG. 1A shows the human mu opioid receptor gene structure and alternative splicing. Exons and introns are showed by boxes and horizontal lines, respectively.

In view of the strong pharmacological evidence for distinct mu-opioid receptors, alternative splicing of the MOR-1 gene has been explored further. It has now been determined that the MOR-1 gene is subject to alternative splicing that produces novel splice variant forms of the mRNA and/or receptor. New exons for the MOR-1 gene have been identified, which combine to yield novel MOR-1 splice variant polynucleotides. These splice variant polynucleotides and the polypeptides encoded thereby are potential targets for modulating morphine analgesia and opioid-mediated ingestive responses.

The invention further encompasses isolated MOR-1 splice variant polynucleotides having the sequences of SEQ ID NOS: 50, 52, 54, 56, 58 or 60. In addition to SEQ ID NOS 50, 52, 54, 56, 58 or 60, the polynucleotide sequences can be any sequence of the appropriate genetic code to encode any of the MOR-1 splice variant polypeptides having the sequence of SEQ ID NOS: 51, 53, 55, 57, 59 or 61. Preferably, the polynucleotide is at least 15 consecutive nucleotides.

The invention further encompasses isolated MOR-1 splice variant polynucleotides having the sequences of SEQ ID NOS: 79, 81, 83, 85 or 87. In addition to SEQ ID NOS 79, 81, 83, 85 or 87, the polynucleotide sequences can be any sequence of the appropriate genetic code to encode any of the MOR-1 splice variant polypeptides having the sequence of SEQ ID NOS: 80, 82, 84, 86 or 88. Preferably, the polynucleotide is at least 15 consecutive nucleotides.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, preferably at least 70%, more preferably at least 80%, and even more preferably at least 90% free of these materials.

The invention further comprises a complementary strand to the MOR-1 splice variant polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the MOR-1 splice variant polypeptides and functionally equivalent fragments thereof which may enhance, decrease or not significantly affect properties of the polypeptides encoded thereby. These functionally equivalent variants, derivatives, and fragments display the ability to retain MOR-1 activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

The invention further encompasses the MOR-1 splice variant polynucleotides contained in a vector molecule or an expression vector and operably linked to a promoter element if necessary.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, or it can be obtained directly from the DNA by using a DNA-dependent RNA polymerase.

Expression vectors generally are replicable polynucleotide constructs that contain a polynucleotide encoding the polypeptide of interest. Herein, this means any of the MOR-1 splice variant polypeptides. For expression, one or more translational controlling elements are also usually required, such as ribosome binding sites, translation initiation sites and stop codons. These controlling elements (transcriptional and translational) can be derived from the MOR-1 gene, or heterologous (i.e., derived from other genes or other organisms). A number of expression vectors suitable for expression in eukaryotic cells including yeast, avian, and mammalian cells are well known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of an MOR-1 splice variant polypeptide of interest. Another example of an expression vector system is the baculovirus/insect system.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available for complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., $pUC_{18}$, mp18, mp19, pBR322, pMB9, ColE1, pCR1, RP4, phage DNAs, and shuttle vectors such as pSA3 and pAT28. These and other cloning vectors are available from commercial vendors such as BioRad, Stratagene, and Invitrogen.

According to an embodiment of the invention, the vectors, e.g., in vivo expression vectors, are viral vectors. Viral vectors, e.g., viral expression vectors are advantageously: poxviruses, e.g. vaccinia virus or an attenuated vaccinia virus. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters. When the expression vector is a poxvirus, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia. When the expression vector is a herpes virus, the polynucleotide to be expressed is inserted under the control of a eukaryotic promoter, such as a strong eukaryote promoter, advantageously a CMV-IE (murine or human) promoter; that is, in embodiments herein, the polynucleotide to be expressed is operably linked to a promoter, and in herpes virus embodiments, advantageously the polynucleotide to be expressed is operably linked to a strong eukatyotic promoter such as a mCMV-IE or hCMV-IE promoter.

Figure 2:
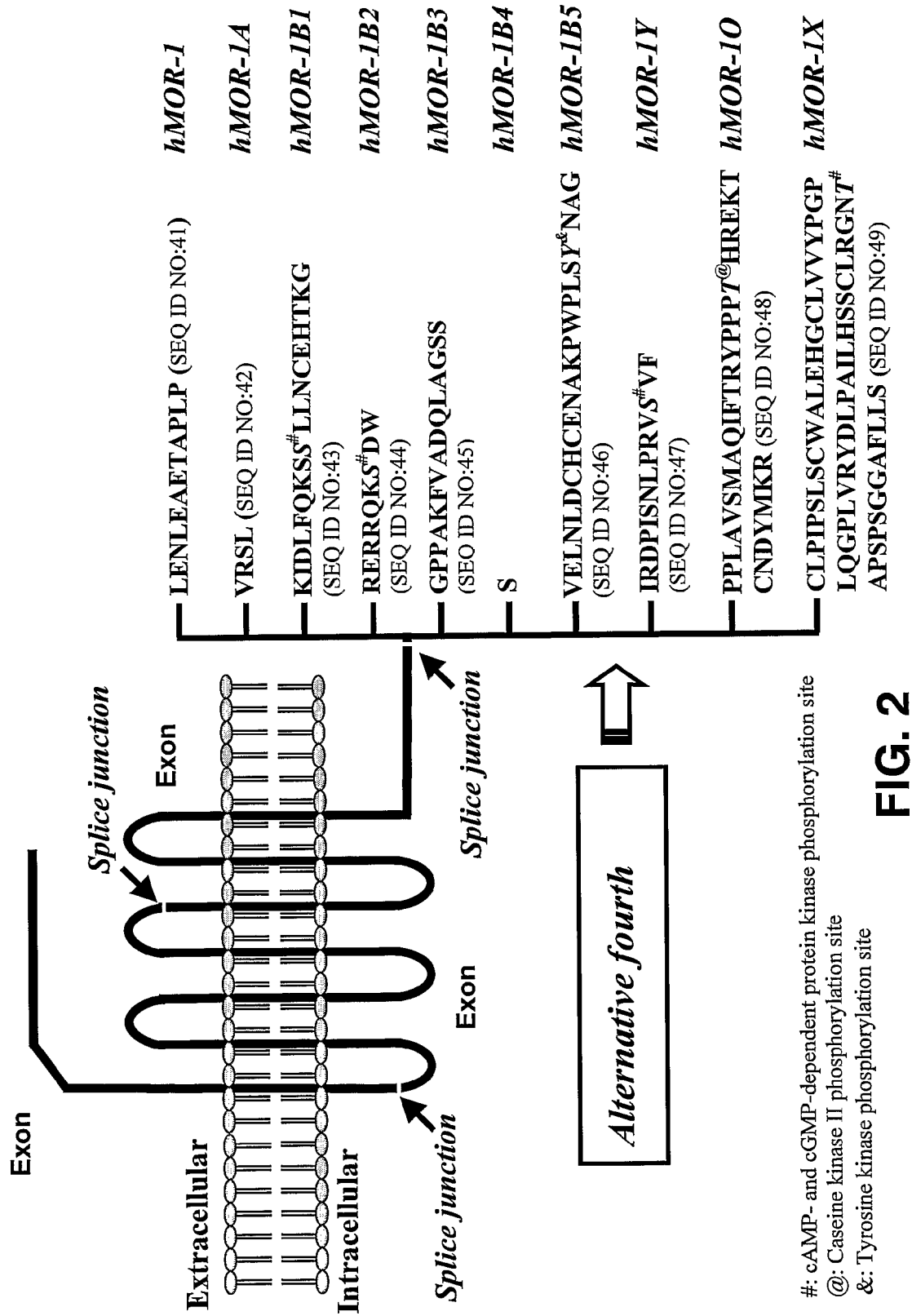
FIG. 2 shows a schematic of the protein structure for the human MOR-1 variants.

The invention further encompasses an isolated polynucleotide, or a complementary strand thereto that hybridizes under stringent conditions, comprising at least 15 consecutive nucleotides of the MOR-1 splice variant polynucleotides depicted in FIG. 2 where the polynucleotide contains promoter elements.

The MOR-1 splice variant promoter elements are contained in exons 1a, 1b, and 1c or in any combination thereof. Promoter elements can control the level, tissue specificity, inducibility and, in gene clusters, the sequence of transcriptional activation and repression. Promoter elements include but are not limited to, enhancer sequences and repressor sequences.

The invention encompasses splice variant polypeptides. The exemplary MOR-1 splice variant polypeptides are composed of the amino acids indicated in FIGS. 3 and 6. Polypeptide fragments comprising 5 amino acids, more preferably 7 amino acids, more preferably 15 amino acids, more preferably 25 amino acids, more preferably 50 amino acids and more preferably 75 amino acids, which are not the same as the known MOR-1 or MOR-1 variants are claimed herein and encompassed in the term "MOR-1 splice variant polypeptides".

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The MOR-1 splice variant polypeptides retain MOR-1 activity. To "retain MOR-1 activity" is to have a similar level of functional activity as the MOR-1 polypeptide. This activity includes, but is not limited to, immunologic and pharmacologic activity.

The "immunologic activity" is binding to anti-opioid receptor antigen binding fragments. The antigen binding fragments can be any functional antibody, fragment or derivative thereof, including, but not limited to, whole native antibodies, bispecific antibodies, chimeric antibodies, Fab, F(ab') 2, single chain V region fragments (scFv), and fusion polypeptides comprising an antigen binding fragment fused to a chemically functional moiety.

The "pharmacologic activity" is activation or deactivation of the MOR-1 splice variant polypeptides upon binding of agonists or antagonists.

The invention further encompasses MOR-1 splice variant polypeptide homologs. A "homolog" is a polypeptide similar in amino acid sequence to other polypeptides among a single species or, a "homolog" in evolution is a polypeptide similar in amino acid sequence to other polypeptides in different species because they have been inherited from a common ancestor. Preferably, homologs of the present invention are human homologs.

Isolation of MOR-1 splice variant human homolog cDNAs can be carried out by any method known in the art. For instance, methods analogous to the isolation of the human and rat MOR-1 splice variants described herein (see Examples 1 and 2). Using primers corresponding to the human MOR-1 gene and a Marathon-Ready human cDNA Library to carry out reactions according to the Marathon cDNA Amplification Kit (Clontech), human MOR-1 splice variants can be obtained. Alternatively, screening of human cDNA libraries with probes corresponding to mouse MOR-1 splice variant sequences can be carried out at reduced stringency to identify human MOR-1 splice variant cDNAs.

The invention further encompasses the MOR-1 splice variant polypeptides in a heterodimeric or homodimeric form. A "heterodimer" is a protein made up of more than one kind of polypeptide. A "homodimer" is a protein made up of more than one kind of polypeptide.

Pharmaceutical compositions and treatment modalities can be detected by the methods of this invention. The MOR-1 splice variant polypeptide fragments and MOR-1 splice variant nucleic acid sequences can be used in screening for compositions that alter variant activity. Compositions that selectively regulate the MOR-1 splice variant polypeptide fragments or selectively modulate physiological processes can be identified.

The invention further encompasses methods of screening compositions for opioid activity by obtaining a control cell that does not express a recombinant opioid receptor and obtaining a test cell that is the same as the control cell except that it expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further comprises a method of screening compositions for opioid activity by obtaining a control polypeptide that is not a recombinant opioid receptor and obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid and comparing the test polypeptide binding of the composition to that of the opioid, where determination of binding of the composition is expressed relative to that of the opioid.

The invention further encompasses a method of screening compositions for differential opioid activity by obtaining a first test polypeptide that is an MOR-1 splice variant polypeptide and contacting it with a composition and obtaining a second test polypeptide that is an MOR-1 splice variant polypeptide, measuring the binding of the composition to the first and second test polypeptides, and comparing the binding of the composition and the first test polypeptide to that of the second test polypeptide where differential activity is expressed as a ratio of the two binding affinities.

The invention further encompasses methods of screening compositions for a MOR-1 binding protein by obtaining a control cell that does not express a recombinant or endogenous opioid receptor, obtaining a test cell that expresses a recombinant MOR-1 splice variant polypeptide, contacting the control cell extract and test cell extract with the MOR-1 splice variant polypeptide and comparing the test cell extract binding to that of the control cell extract binding with the MOR-1 splice variant polypeptide of interest to identify a MOR-1 binding protein. For example, but not by limitation, the MOR-1 binding protein can be identified by two hybrid screen, which is known to one of skill in the art (see, e.g., U.S. Pat. Nos. 5,525,490; 5,948,620; 5,955,280; 5,965,368; 6,051,381; 6,251,676; 6,479,289 and 6,562,576).

The compositions screened include, but are not limited to, chemical, synthetic combinatorial libraries of small molecule ligands, eukaryotic whole cell lysates or extracts, media conditioned by cultured eukaryotic cells, natural products and extracts thereof.

The opioid can be, but is not limited to, morphine, methadone, etorphine, levorphanol, fentanyl, sufentanil, [D-Ala$^2$, MePhe$^4$, Gly(ol)$^5$]enkephalin (DAMGO), pentazocine, ethylketocyclazocine, bremazocine, spiradoline, [D-Ser$^2$, Leu$^5$] enkephalin-Thr$^6$ (DSLET), Met-enkephalin, Leu-enkephalin, β-endorphin, dynorphin A, dynorphin B, α-neoendorphin analogs and combinatorial chemistry products thereof.

The physiological effect can be measured by any method known in the art such as changes in the levels of neuroendocrine hormones, including, but not limited to prolactin, growth hormone, gonadotropin-releasing hormone, adrenocorticotropin, corticotropin-releasing factor, luteinizing hormone, follicle stimulating hormone, testosterone or cortisol. The physiological effect can also be measured by changes in the levels of neurotransmitters, including but not limited to, acetylcholine or dopamine.

Activation of an MOR-1 receptor, and likely, the MOR-1 splice variant polypeptides, stimulates a variety of physiological responses, including analgesia, depression of gastrointestinal motility and respiration, and alterations of the immune, endocrine and autonomic nervous system. Compositions that regulate the activity of the MOR-1 receptor and/or the MOR-1 splice variant polypeptides can elicit responses that have therapeutic effects. The invention is useful in diagnosis, treatment, design and screening of novel reagents. Screening of compounds can result in obtaining those with differential or selective activity. That is, for instance, certain compositions can retain analgesic effects but do not affect peristaltic activity and thus do not cause constipation. Conversely, compositions that lack analgesic effects but affect peristaltic activity would be useful in treating chemotherapy and HIV patients. Other applications relating to the side effects of opiates can be readily envisaged by one of skill in the art.

The invention further encompasses a method for regulating morphine analgesia in a subject by altering the amount of MOR-1 splice variant polypeptide activity in the subject. Activity can be regulated by administering antigen binding fragments, agonists, antagonists or small molecule ligands to a subject in an amount and duration sufficient to regulate morphine analgesia. The antigen binding fragment, agonist, antagonist or small molecule ligand is directed to an MOR-1 splice variant. Activity can also be regulated by homodimerization or homooligomerization among the MOR-1 splice variants and heterodimerization or heterooligomerization between the variants and other opioid or non-opioid receptors.

Activity can also be regulated by administering a DNA plasmid vector containing an MOR-1 splice variant polynucleotide. The DNA plasmid vector thereby expresses an MOR-1 splice variant polynucleotide in a subject in an amount and a duration sufficient to regulate morphine analgesia. Activity can also be regulated by administering an antisense nucleic acid or siRNA complementary to an MOR-1 splice variant polynucleotide, thereby blocking gene expression in a subject in an amount and a duration sufficient to regulate morphine analgesia. Methods for administering antisense and siRNA are known to one of skill in the art (reviewed in Brantl, Biochim Biophys Acta. 2002 May 3; 1575(1-3):15-25 and Lavery & King, Curr Opin Drug Discov Devel. 2003 July; 6(4):561-9).

Agonists and antagonists of MOR-1 splice variant polypeptide activity can include but are not limited to, morphine, methadone, etorphine, levorphanol, fentanyl, sufentanil, [D-Ala$^2$, MePhe$^4$, Gly(ol)$_5$]enkephalin (DAMGO), butorphanol, naloxone, naltrexone, D-Phe-Cys-Tyr-D-Trp-Orn-Thr-Pen-Thr-NH$_2$ (CTOP), diprenorphine, β-funaltrexamine, naloxonazine, nalorphine, pentazocine, nalbuphine, benzoylhydrazone, bremazocine, ethylketocyclazocine, trans-(−)-3,4-dichloro-N-methyl-N-[2-(1-pyrrolidinyl)cyclohexyl]benzeneacetamide (also known as U50488), (5-alpha,7-alpha,8-beta)-(+)-N-methyl-N-[7-(1-pyrrolidinyl)-1-oxaspiro(4,5)dec-8-yl]-benzeneacetamide (also known as U69593), spiradoline, naltrindole, [D-Pen$^2$, D-Pen-$^5$]enkephalin (DPDPE), [D-Ala$^2$,Glu$^4$]deltorphin, [D-Ser$^2$,Leu$^5$] enkephalin-Thr$^6$ (DSLET), Met-enkephalin, Leu-enkephalin, β-endorphin, dynorphin A, dynorphin B, α-neoendorphin and derivatives such as those produced by combinatorial chemistry and their mixtures and physiologically acceptable salts thereof.

A "subject" is a vertebrate, preferably a mammal, and more preferably a human. Mammals include but are not limited to humans, farm animals, sport animals, and pets.

The invention further encompasses antigen binding fragments specific for an MOR-1 splice variant polypeptide. According to the invention, an MOR-1 splice variant polypeptide can be used as an immunogen to generate antigen-binding fragments which immunospecifically bind the immunogen.

Production of antigen binding fragments such as polyclonal antibodies can be carried out by any method known in the art. Various host animals can be immunized by injection with the immunogen, including but not limited to rabbits, mice and rats. Various adjuvants can be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of antigen binding fragments such as monoclonal antibodies, any technique that provides for the production of antibody molecules by continuous cell lines in culture can be used. Examples of such techniques include the original hybridoma technique (Kohler and Milstein (1975) Nature 256:495) as well as the trioma technique, the human B-cell hybridoma technique (Kozbor et al. (1983) Immunol. Today 4:72), and the EBV hybridoma technique to produce human monoclonal antibodies. Cole et al. (1985) in Monoclonal Antibodies and Cancer Therapy, Alan R. Liss, Inc., pp. 77-96. Monoclonal antibodies can also be produced in germ-free animals utilizing known technology. PCT/US90/02545. Human antibodies can be obtained using human hybridomas (Cote et al. (1983) Proc. Natl. Acad. Sci. U.S.A. 80:2026), or by transforming human B cells with EBV virus in vitro. Cole et al. (1985). Techniques developed for the production of "chimeric antibodies" by splicing the genes from a mouse antibody molecule specific for MOR-1 splice variants together with genes from a human antibody of appropriate biological activity can be used. Morrison et al. (1984) Proc. Natl. Acad. Sci. U.S.A. 81:6851; Neuberger et al. (1984) Nature 312:604; and Takeda et al. (1985) Nature 314:452.

Techniques described for the production of single chain antibodies (U.S. Pat. No. 4,946,778) can be adapted to produce MOR-1 splice variant polypeptide-specific single chain antibodies. Techniques described for the production of Fab expression libraries (Huse et al. (1989) Science 246:1275) can be utilized, allowing rapid and easy identification of monoclonal Fab fragments specific for an MOR-1 splice variant polypeptide.

Antibody fragments that contain the idiotype of the molecule can be generated by known techniques. For example, such fragments include but are not limited to: the F(abl), fragment which can be produced by pepsin digestion of the antibody molecule; the Fab' fragments which can be generated by reducing the disulfide bridges of the F(abl) fragment, the Fab fragments which can be generated by treating the antibody molecule with papain and a reducing agent, and Fv fragments.

Single chain V region fragments ("scFv") can also be produced. Single chain V region fragments are made by linking L (light) and/or H (heavy) chain V (variable) regions by using a short linking peptide. Bird et al. (1988) Science 242:423. Any peptide having sufficient flexibility and length can be used as a linker in a scFv. Usually the linker is selected to have little to no immunogenicity. An example of a linking peptide is (GGGGS)$_3$, which bridges approximately 3.5 nm between the carboxy terminus of one V region and the amino terminus of another V region. Other linker sequences can also be used, and can provide additional functions, such as for attaching a drug or a solid support.

All or any portion of the H or L chain can be used in any combination. Typically, the entire V regions are included in the scFv. For instance, the L chain V region can be linked to the H chain V region. Alternatively, a portion of the L chain V region can be linked to the H chain V region or a portion thereof. Also contemplated are scFvs in which the H chain V region is from H11, and the L chain V region is from another immunoglobulin. It is also possible to construct a biphasic, scFv in which one component is an MOR-1 splice variant polypeptide and another component is a different polypeptide, such as a T cell epitope.

The scFvs can be assembled in any order, for example, V$_H$-(linker)-V$_L$ or V$_L$-(linker)-V$_H$. There may be a difference in the level of expression of these two configurations in particular expression systems, in which case one of these forms may be preferred. Tandem scFvs can also be made, such as (X)-(linker)-(X)-(linker)-(X), in which X are MOR-1 splice variant polypeptides, or combinations of MOR-1 splice variant polypeptides with other polypeptides. In another embodiment, single chain antibody polypeptides have no linker polypeptide, or just a short, inflexible linker. Exemplary configurations include V$_L$-V$_H$ and V$_H$-V$_L$. The linkage is too short to permit interaction between V$_L$ and V$_H$ within the chain, and the chains form homodimers with a V$_L$/V$_H$ antigen-binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

The following examples are provided to illustrate but not limit the claimed invention. The examples demonstrate isolation and characterization of MOR-1 splice variants, and are representative of the methods employed for all claimed MOR-1 splice variants.

EXAMPLE 1

Identification and Characterization of Six New Alternatively Spliced Variants from the Human Mu Opioid Receptor Gene, Oprm The mu opioid receptor plays an important role in mediating the actions of morphine and morphine-like drugs. Binding and pharmacological studies have proposed several mu receptor subtypes, but only one mu opioid receptor (Oprm) gene has been isolated. The Examples herein describe the identification and characterization of six new splice variants from the human Oprm gene using an RT-PCR strategy. The variants display differences on their carboxyl termini resulting from alternative splicing of the fourth exon. Northern blot analysis demonstrated expression of the variant mRNAs. Receptor binding assays established that these variants belonged to the mu opioid receptor family with limited differences in opioid ligand affinities. However, adenylyl cyclase assays revealed significant differences in both opiate potency and efficacy among these variants. Dissociation between binding affinity and efficacy/potency among these variants might provide important insights to understanding the varied opioid responses observed clinically, and into designing new selective drugs based upon these differences in efficacy/potency.

Primer design. In order to identify potential mouse homologs containing exons 5 in the human Oprm gene, a sequence alignment was performed among a ~7.7 kb mouse genomic sequence containing exons 5a, 5b, 5c, 5d and 5e, a ~7.3 kb rat and a ~8 kb human corresponding genomic sequences obtained from Public human genome databases (NBCI and Ensembl), with Vector NTI software (Informax). Three sets of antisense primers were designed. One of the primers (primer A) was derived from the human exon 5a that was highly homologous to the mouse or rat exon 5a, while the other two sets of primers (primers B and C) were from the regions homologous to the mouse exons 5c and 5d, respectively.

Reverse transcription-polymerase chain reaction (RT-PCR) cloning. Total RNA was extracted from Be(2)C, a human neuroblastoma cell line, with the guanidinium thiocyanate phenol-chloroform extraction method (see, e.g., Pan et al. (1995) Molecular Pharmacology 47, 1180-1188), and reverse transcribed with primer A (5'-GCT TCC AAT CTT ATA TTC TTT CAC GG-3', SEQ ID NO:1) and Superscript II reverse transcriptase (Invitrogen) as previously described. The first-strand cDNA was then used as a template in PCRs with a sense primer A1 from the 5' untranslated region of exon 1 (5'-GAA AGG AAG CGG CTG AGG CGC T-3', SEQ ID NO:2) and the antisense primer A from exon 5a, or the antisense primer B1 from exon 5c (5'-GTG TAT TGT CTA TTA GAG TGA GGC TAA CAT TTC TTT GG-3', SEQ ID NO:3), or the antisense primer C1 from exon 5d (5'-CCA CAC GGC AGT ACC TTC TCT TGG TCT CC-3', SEQ ID NO:4). Having no visible bands by the first-round PCR, nested PCRs were followed by using the first-round PCR products as templates and nested primers including a sense primer A2 (5'-CGG TGC TCC TGG CTA CCT CGC A-3', SEQ ID NO:5) and the antisense primer A, or the antisense primer B2 (5'-GGT TAG ATG GCT TTT ATC ATC ATA TTG CTG G-3', SEQ ID NO:6), or the antisense primer C2 (5'-GGG AAC AGG AAT TTT AGG GTT CAT GTCATA G-3', SEQ ID NO:7). Six cDNA fragments arranging from ~1.2 to 2.6 kb in size were obtained, subcloned into pCRII-TOPO vector (Invitrogen), and sequenced in both strands. Sequence analysis of the cDNAs showed that all the clones had the same exons 1, 2 and 3 as the original hMOR-1, but contained an alternative fourth exon that was resulted from combination of six different exons (exons 5a, 5b, 5c, 5d, 5e and Y generated by using different splice site within exon 5 and a novel exon, exon Y). The corresponding variants were named as hMOR-1B1, hMOR-B2, hMOR-1B3, hMOR-1B4, hMOR-1B5 and hMOR-1Y, respectively. hMOR-1A was amplified from the first-strand cDNA reverse-transcribed from Be(2)C RNA with random primers in a nested PCR using two sense primers (A1 & A2) from exon1 and two antisense primers (D1: 5'-GCT TCC CCT CTT CCC TCC ATT CTC-3', SEQ ID NO:8; D2: 5'-GGA TTA AAC TCC TAG TTT AGC ACA AAG CC-3', SEQ ID NO:9) from exon 3b sequence obtained from Public genome databases.

Northern blot analysis. Northern blot analysis was performed as described previously (see, e.g., Pan et al. (2001) Proc. Natl. Acad. Sci. U.S.A 98, 14084-14089). In brief, total RNA was isolated from Be(2)C cells (see above). 20 μg of total RNA per lane was loaded, separated on a 0.8% formaldehyde agarose gel, and transferred to a GenePlus membrane. The membrane was then hybridized with $^{32}$P-labeled cDNA probes generated by PCR with appropriate primers. The primers used were a sense primer (E: 5'-GCC ACC AGT ACC CTG CCC TTC C-3', SEQ ID NO:10) from exon 2 and an antisense primer (F: 5'-CTC AAT GTT GGA AGA GGT TGG GAT AC-3', SEQ ID NO:11) from exon 3 for a exons 2&3 probe, a sense primer (G: 5'-GTA CGC AGT CTC TAG AAT TAG GTA TAT CTA CTG-3', SEQ ID NO: 12) and an antisense primer (H: 5'-GGA TTC TAG ATC AGA ATT ATT TCT ATA ATG TGC-3', SEQ ID NO:13) from exon 3b for an exon 3b probe, a sense primer (I: 5'-GAG ACC ACC CCT CCA CGG C-3', SEQ ID NO: 14) from exon 3a and an antisense (J: 5'-GGT CTC CAT TAG GGC TAG CAG CAG-3', SEQ ID NO:15) from exon 5a for na exon 5a probe, a sense primer (K: 5'-CAG AGA GAA AGA AGA CAG AAA TCT GAC TGG TAA G-3', SEQ ID NO:16) and an antisense primer (L: 5'-GAG AGC ACG TGT TGA AAC TGC AAG TCA GAG-3', SEQ ID NO:17) from exon 5b for an exon 5b probe, a sense primer (M: 5'-GGA CCT CCA GCC AAG TTT GTT GCT GAC-3', SEQ ID NO:18) and an antisense primer (N: 5'-CTC TCT GTG CAA ACG GTT GAA TGA ATG G-3', SEQ ID NO:19) from exon 5c for an exon 5c probe, a sense primer (O: 5'-CAG AGC TGA CTA TGA CAT GAA CCC TAA AAT TCC TG-3', SEQ ID NO:20) and an antisense primer (P: 5'-GGT CCC TGA AAC CAA CAA AAA AAC TGG ATG-3', SEQ ID NO:21) from exon 5d for an exon 5d probe, a sense primer (Q: 5'-CAG GTG GAA TTG AAC CTG GAC TGT CAC TGT G-3', SEQ ID NO:22) and an antisense primer (S: 5'-GCT CTA AAA ATC ATA TGA AAT AGT TAC AAG CCT TTG-3', SEQ ID NO:23) from exon 5e for an exon 5e probe, and a sense primer (T: 5'-CAT CAG ATC AGA GAT CCA ATA TCA AAC CTT CCC-3', SEQ ID NO:24) and an antisense primer (U: 5'-GGA GGT CCC TTG ATA ACT GCC AAA TCG C-3', —SEQ ID NO:25) from exon Y for an exon Y probe. The sizes of the probes were 728 bp for exons 2&3 probe, 319 bp for exon 3b probe, 184 bp for exon 5a probe in which a 47 bp sequence was from exon 3a, 309 bp for exon 5b probe, 272 bp for exon 5c probe, 145 bp for exon 5d probe, 156 bp for exon 5e probe, and 122 bp for exon Y probe, respectively. After washing, the membranes were exposed to Kodak BioMax MS film.

Expression of the variants in Chinese Hamster Ovary (CHO) cells. The cDNA fragments containing full-length variants including the original hMOR-1 in pCRII-TOPO were subcloned into pcDNA5FRT (Invitrogen) or pcDNA3 vector. A cDNA fragment containing only exons 1, 2 and 3 was also generated by PCR with the sense primer A2 from exon 1 (see above) and an antisense primer (V: 5'-GAT CTC GAG TCA TTA CTG ATG ATT AGT TCT ATC CAC TGT ATT GGC-3, SEQ ID NO:26) and subcloned into pcDNA5FRT. The resulting plasmids, hMOR-1/pcDNA5FRT, hMOR-1A/pcDNA5FRT, hMOR-1B1/pcDNA3, hMOR-1B2/pcDNA5FRT, hMOR-1B3/pcDNA5FRT, hMOR-1B4/pcDNA5FRT, hMOR-1B5/pcDNA5FRT, hMOR-1Y/pcDNA5FRT and hMOR-1 (exons 1-3)/pcDNA5FRT were transfected into CHO cells with or without pOG44 construct (Flip-In system, Invitrogen) by LipofectAMINE reagent (Invitrogen). Stable transformants were obtained 10-14 days after selection with hygromycin or G418 and screened with [$^3$H]DAMGO binding assay.

Receptor Binding Assays. Membranes were prepared from stable transfectants as described previously (see, e.g., Pan et al. (1999) Molecular Pharmacology 56, 396-403). [$^3$H] DAMGO saturation and competition binding assays were performed at 25° C. for 60 minutes in 50 mM potassium phosphate buffer, pH 7.4, containing 5 mM magnesium sulfate. Specific binding was defined as the difference between total binding and nonspecific binding, determined in the presence of levallorphan (10 μM). $K_D$, Bmax and $K_i$ values were calculated by nonlinear regression analysis (GraphPad Prism, Carslbad, Calif.). Protein concentrations were determined as previously described using BSA as the standard (see, e.g., Lowry et al. (1951) Journal of Biological Chemistry 193, 265-275).

Adenylyl cyclase assay. Adenylyl cyclase activity in intact cells was determined as previously reported (Thakker et al. (2003) Methods Mol. Med. 84, 29-37). Briefly, intact stable transfectant cells (0.07-0.18 mg of protein) were incubated in Hanks' balanced salt solution (137 mM NaCl, 5 mM KCl, 0.6 mM $Na_2HPO_4$, 0.4 mM $KH_2PO_4$, 4 mM $NaHCO_3$, 6 mM D-glucose, 0.5 mM $MgCl_2$, 0.4 mM $MgSO_4$, and 1 mM $CaCl_2$) containing 0.5 mM 3-isobutyl-1-methylxanthine for 5 min at 37° C. after adding forskolin (10 μM) and/or agonists (0.01 nM-10 μM) on ice, cells were then incubated for 10 min at 37° C. The reaction was stopped by incubating the tubes in a boiling water bath for 6 min. The tubes were centrifuged for 5 min at 11,000 g, and cAMP levels from the supernatant were then measured in a competition assay for [$^3$H]cAMP binding. The supernatants were incubated with 0.8 pM [$^3$H]cAMP in binding buffer containing 25 mM Tris-HCl, pH 7.0, 10 mM theophylline, 0.1% BSA, and 0.25 mg/ml adrenal cortex extract for 1 h at 4° C. After adding 75 μl of hydroxyapatite [50% (w/v)] and incubating for 6 min at 4° C. to terminate the reaction, the reaction was then filtered through No. 34 glass-fiber filters (Schleicher & Schuell) and washed three times with 3 ml of ice-cold 10 mM Tris-HCl, pH 7.0 on a semiautomatic cell harvester. Filters were transferred into vials with 5 ml of Liquiscent (National Diagnostics, Atlanta, Ga.), and the radioactivity in vials were determined by scintillation spectroscopy in a Packard TRI-CAEB 2900TR counter. A parallel standard curve setting using unlabeled cAMP (0.4-125 μmol) was performed to calculate the cAMP level in the supernatants.

Cloning new splice variants from the human Oprm Gene. To isolate potential human MOR-1 variants homologous to those identified in mice, three sets of human antisense primers were designed based upon the genomic sequence alignment among mouse, rat and human, and then used these antisense primers together with two sense primers from 5'UTR of exon 1 in an RT-PCR strategy. Six new variants were identified, hMOR-1B1, hMOR-1B2, hMOR-1B3, hMOR-1B4, hMOR-1B5 and hMOR-1Y, from Be(2)C, a human neuroblastoma cell line that expresses high level of mu opioid receptors (FIG. 1A). Sequence analysis revealed that all the variants contained the same exons 1, 2 and 3 as the original MOR-1, but had a different fourth exon, which resembled splicing patterns similar to two earlier human (hMOR-1O and hMOR-1X) as well as eleven mouse (mMOR-1B1, mMOR-1B2, mMOR-1B3, mMOR-1B4, mMOR-1B5, mMOR-1C, mMOR-1D, mMOR-1E, mMOR-1F, mMOR-1O and mMOR-1P) variants (see, e.g., Pan et al. (2000) FEBS Letters 466, 337-340 and Suzuki et al. (1998) Life Sciences 64, PL1-PL7). Therefore, all these variants contained the same protein structure on cell membrane, except with a different intracellular carboxyl terminus (FIG. 2). The common protein sequence includes all seven transmembrane domains and the binding pocket. Similar to the mouse variants associated with exons 5 (mMOR-1B1, mMOR-1B2, mMOR-1B3, mMOR-1B4 and mMOR-1B5), the human exon 5 variants were produced from alternative splicing within exon 5 and all the splice junctions contained consensus splicing sequences. However, the predicted amino acid sequences from the human variants differed from those from the mouse variants, and from each other due to sequence divergence (FIGS. 1B and 2).

In hMOR-1B1, the first five of the total eighteen amino acids deduced from exon 5a were identical to those in mMOR-1B1 and rat MOR-1B. However, there was no termination codon after the fifth amino acid as in mMOR-1B1 and rMOR-1B, and translation stopped after the eighteenth amino acid. Therefore, hMOR-1B1 contained an additional thirteen amino acids on its carboxyl terminal. Exons 5b, 5c, 5e and Y predicted 9, 15, 22 and 14 amino acids in hMOR-1B2, hMOR-1B3, hMOR-1B5 and hMOR-1Y, respectively, whereas exon 5d in hMOR-1B4 deduced only one amino acid, a serine residue, the shortest version of all carboxyl terminal variants cloned so far. Several potential protein kinase phosphorylation sites for cAMP- and cGMP-dependent protein kinase and tyrosin kinase were present in hMOR-1B1, hMOR-1B2 and hMOR-1Y, respectively (FIGS. 1B and 2).

Northern blot analysis of human MOR-1 variant mRNA. Northern blot analysis was performed to estimate the relative size and abundance of the variant mRNAs. Since all the variants contained exons 1, 2 and 3, the exons 2/3a probe was designed as a control to define all the variants. It detected several diffuse and heavy bands ranging from 2 to 15 kb. A similar band pattern was also seen in the mouse and rat Northern blots with their exons 2/3a probes. The exon 5a probe hybridized a strong band around 12 kb, which had a similar size and an intensity when compared to the higher band detected by the exon 4 probe that defines the original human MOR-1. This similarity implied that there was a relatively high abundance for the variants associated with exon 5a. The exon 5a probe also hybridized several light diffuse bands at approximately 15, 3.5 to 5 and 2 to 3 kb, respectively, suggesting that exon 5a may be associated with multiple variants. However, the exons 5b, 5c, 5d, 5e and Y probes as well as exon 3b probe all detected a well-defined band at about 15 kb, suggesting that they may share a similar RNA structure, particularly in the 3'UTR, even if the protein sequences are different. The exon Y probe also hybridized two distinct bands at approximately 12 and 3.5 kb. Although the smaller one may be a degradation product, it also is possible that exon Y may be associated with more than one variant.

Table 1 depicts the identity and homology among the human mu opioid receptor variants.

Table 2 presents the saturation studies with [$^3$H]DAMGO. [$^3$H]DAMGO binding was performed in membranes isolated from stable transfectants containing the indicated cDNA clones. The binding parameters were established by nonlinear regression analysis. Results are the mean ±S.E.M of at least three independent determinations.

Table 3 presents the competition of [$^3$H]DAMGO binding among the human MOR-1 variants. Competition studies against [$^3$H]DAMGO (~1 nM) were performed with indicated ligands using at least three concentrations of drugs and the Ki value calculated as previously described. Results are the means ±S.E.M. of three independent determinations. The ligands that showed significant differences among the variants using ANOVA were DAMGO ($p<0.0262$), Morphine ($p<0.0359$), M6G ($p<0.0003$), DSLET ($p<0.0027$), endomorphin 1 ($p<0.0068$), endomorphin 2 ($p<0.0084$), β-endorphin ($p<0.0005$). For DAMGO, Tukey determined differences between hMOR-1(exons 1-3) and hMOR-1B2, hMOR-1B1 and hMOR-1B2, hMOR-1B3 and hMOR-1B2 ($p<0.05$). For morphine, Tukey determined differences between hMOR-1 (exons 1-3) and hMOR-1B2, hMOR-1B1 and hMOR-1B2, hMOR-1B2 and hMOR-1B3 ($p<0.05$). For M6G, Tukey determined differences between hMOR-1 and hMOR-1B2, hMOR-1(exons 1-3) and hMOR-1B2, hMOR-1A and hMOR-1B2, hMOR-1B1 and hMOR-1B2, hMOR-1B2 and hMOR-1B 3($p<0.01$). For DSLET, Tukey determined differences between hMOR-1 and hMOR-1B2($p<0.05$), hMOR-1 (exons 1-3) and hMOR-1B2 ($p<0.01$), hMOR-1A and hMOR-1B2 ($p<0.05$), hMOR-1B1 and hMOR-1B2, hMOR-1B2 and hMOR-1B3, hMOR-1B2 and hMOR-1B5, hMOR-1B2 and hMOR-1Y ($p<0.01$). For endomorphin 1, Tukey determined differences between hMOR-1 and hMOR-1B2, hMOR-1(exons 1-3) and hMOR-1B2, hMOR-1B1 and hMOR-1B2 ($p<0.05$). For endomorphin 2, Tukey determined differences between hMOR-1 and hMOR-1(exons 1-3), hMOR-1 and hMOR-1A, hMOR-1 and hMOR-1B1, hMOR-1 and hMOR-1B3 ($p<0.05$). For β-endorphin, Tukey determined differences between hMOR-1 and hMOR-1B2, hMOR-1(exons 1-3) and hMOR-1B2, hMOR-1A and hMOR-1B2, hMOR-1B1 and hMOR-1B2, hMOR-1B2 and hMOR-1B3 ($p<0.01$).

Table 4 depicts saturation studies with [$^3$H]DAMGO. [$^3$H]DAMGO binding was performed in membranes isolated from stable transfectants containing the indicated rat cDNA clones. The binding parameters were established by nonlinear regression analysis. Results are the mean ±S.E. of at least three independent determinations.

Table 5 present the relative efficacy of opioid ligands for hMOR-1 and hMOR-1 variants in adenylyl cyclase assay. The highest level of inhibition for any of the drugs (Table 4) for a specific variant was arbitrarily defined as 100%. Efficacy for all the other compounds for the indicated variant was defined as the percentage of the maximal inhibition for that variant.

Table 6 depicts the inhibition of forslolin-stimulated cAMP accumulation by opioids in hMOR-1 variants. The $IC_{50}$ and maximal inhibition were calculated by nonlinear regression analysis (Prism 3.0). Results are the means ±S.E.M. of at least three independent determinations. Significant differences of maximal inhibition analyzed by ANOVA were DAMGO ($p<0.0001$), and morphine ($p<0.0001$). For maximal inhibition by DAMGO, post hoc analysis using Tukey revealed significant differences between hMOR-1 and hMOR-1B1 ($p,0.05$), hMOR-1A and hMOR-1B1 ($p<0.01$), hMOR-1B1 and hMOR-1B2 ($p<0.001$), hMOR-1B1 and hMOR-1B5 ($p<0.01$), hMOR-1B1 and hMOR-1B6 ($p<0.001$), hMOR-1B2 and hMOR-1B4 ($p<0.01$), hMOR-1B3 and hMOR-1B6 ($p<0.05$), hMOR-1B4 and hMOR-1B6 ($p<0.01$). For maximal inhibition by morphine, Tukey determined significant differences between hMOR-1 and hMOR-1B3, hMOR-1(exons 1-3) and hMOR-1B 3, hMOR-1A and hMOR-1B3 ($p<0.001$), hMOR-1B1 and hMOR-1B6 ($p<0.01$), hMOR-1B2 and hMOR-1B4 ($P<0.05$), hMOR-1B3 and hMOR-1B4, hMOR-1B4 and B6 ($p<0.01$), hMOR-1B3 and hMOR-1B5, hMOR-1B3 and hMOR-1B6 ($p<0.001$). Significant differences of $IC_{50}$ by ANOVA were DAMGO ($p<0.0008$), morphine ($p<0.0002$), β-endorphin ($p<0.0001$). For $IC_{50}$ by DAMGO, Tukey determined significant differences between hMOR-1 and hMOR-1B1, hMOR-1B1 and hMOR-1(exons 1-3) ($p<0.01$), hMOR-1 and hMOR-1B3, hMOR-1(exons 1-3) and hMOR-1B3, hMOR-1A and hMOR-1B1, hMOR-1B1 and hMOR-1B6 ($p<0.05$). For $IC_{50}$ by morphine, Tukey determined significant differences between hMOR-1 and hMOR-1B2, hMOR-1(exons 1-3) and hMOR-1B2 ($p<0.001$), hMOR-1A and hMOR-1B2, hMOR-1B2 and hMOR-1B3, hMOR-1B2 and hMOR-1B4, hMOR-1B2 and hMOR-1B5, hMOR-1B2 and hMOR-1B6 ($p<0.01$). For $IC_{50}$ by β-endorphin, Tukey determined significant differences between hMOR-1 and hMOR-1B5, hMOR-1A and hMOR-1B5, hMOR-1B1 and hMOR-1B5, hMOR-1B5 and hMOR-1B6 ($p<0.001$), hMOR-1B3 and hMOR-1B5, hMOR-1B4 and hMOR-1B5 ($p<0.01$)

TABLE 1

| Identity (Homology) | hMOR-1 (400) | hMOR-1A (392) | hMOR-1B1 (406) | hMOR-1B2 (397) | hMOR-1B3 (403) | hMOR-1B4 (389) | hMOR-1B5 (410) | hMOR-1O (418) | hMOR-1X (446) | hMOR-1Y (402) |
|---|---|---|---|---|---|---|---|---|---|---|
| hMOR-1 (400) | | | | | | | | | | |
| hMOR-1A (392) | 97.3 (99.3) | | | | | | | | | |
| hMOR-1B1 (406) | 96.1 (97.5) | 95.8 (99.3) | | | | | | | | |
| hMOR-1B2 (397) | 97.3 (98.0) | 97.7 (99.0) | 96.1 (98.3) | | | | | | | |
| hMOR-1B3 (403) | 96.5 (97.3) | 97.7 (99.0) | 95.8 (96.6) | 96.5 (98.0) | | | | | | |
| hMOR-1B4 (389) | 96.8 (99.5) | 98.7 (99.5) | 95.3 (99.5) | 97.5 (99.5) | 96.0 (99.5) | | | | | |
| hMOR-1B5 (410) | 95.6 (98.0) | 94.5 (99.3) | 94.4 (97.3) | 95.1 (98.3) | 94.9 (96.6) | 94.4 (99.5) | | | | |
| hMOR-1O (418) | 92.8 (97.1) | 92.8 (99.0) | 92.8 (95.7) | 92.8 (97.8) | 93.5 (97.1) | 92.6 (99.5) | 93.3 (95.2) | | | |
| hMOR-1X (446) | 87.0 (97.3) | 87.0 (99.1) | 87.7 (96.6) | 87.4 (98.4) | 87.2 (96.9) | 86.8 (99.6) | 87.7 (95.7) | 87.4 (93.7) | | |
| hMOR-1Y (402) | 96.5 (97.0) | 96.8 (99.3) | 95.8 (96.8) | 96.5 (97.8) | 96.3 (96.5) | 96.3 (99.5) | 94.6 (96.6) | 93.1 (96.9) | 87.2 (97.1) | |

TABLE 2

| Clone | $K_D$ (nM) | $B_{max}$ (pmol/mg protein) |
|---|---|---|
| hMOR-1 | 1.6 ± 0.6 | 1.01 ± 0.20 |
| hMOR-1(exons 1-3) | 1.2 ± 0.3 | 0.66 ± 0.09 |
| hMOR-1A | 1.7 ± 0.6 | 1.04 ± 0.13 |
| hMOR-1B1 | 3.1 ± 0.8 | 0.49 ± 0.08 |
| hMOR-1B2 | 4.4 ± 0.4 | 0.37 ± 0.04 |
| HMOR-1B3 | 1.6 ± 0.5 | 0.37 ± 0.02 |
| hMOR-1B4 | 2.6 ± 0.2 | 0.56 ± 0.10 |
| hMOR-1B5 | 1.4 ± 0.1 | 0.44 ± 0.08 |
| hMOR-1Y | 2.3 ± 0.6 | 0.69 ± 0.15 |

TABLE 3

| | $K_i$ value (nM) | | | | | | | | |
|---|---|---|---|---|---|---|---|---|---|
| Ligand | hMOR-1 wt | hMOR-1 w/o exon 4 | hMOR-1A | hMOR-1B1 | hMOR-1B2 | hMOR-1B3 | hMOR-1B4 | hMOR-1B5 | hMOR-1B6 |
| DAMGO | 2.0 ± 0.8 | 1.5 ± 0.4 | 2.4 ± 0.6 | 1.2 ± 0.7 | 5.8 ± 2.4 | 1.8 ± 0.9 | 2.3 ± 1.1 | 2.1 ± 0.7 | 2.5 ± 1.4 |
| Morphine | 4.2 ± 1.4 | 2.9 ± 0.9 | 4.4 ± 1.7 | 2.4 ± 2 | 11.2 ± 6.1 | 3.2 ± 1.1 | 5.5 ± 3 | 3.9 ± 1.6 | 4.3 ± 3 |
| M6G | 13.9 ± 3.2 | 11 ± 4.6 | 13.2 ± 6.6 | 5 ± 0.4 | 42.2 ± 13.7 | 15.7 ± 2.1 | 22.8 ± 12.9 | 12.2 ± 4.5 | 8.3 ± 3.9 |
| DADLE | 3.9 ± 1.3 | 4.5 ± 1.5 | 4.9 ± 1.1 | 3.6 ± 2.6 | 10 ± 5.9 | 4.6 ± 0.4 | 5.1 ± 2.1 | 6.8 ± 2.8 | 6.5 ± 3 |
| DSLET | 19.1 ± 5.8 | 14 ± 2 | 19.7 ± 7.7 | 13.9 ± 4.9 | 34.4 ± 6.4 | 16.4 ± 2.8 | 22.3 ± 2 | 16 ± 6.6 | 15.4 ± 3.5 |
| Naloxone | 2.9 ± 0.5 | 1.8 ± 0.4 | 4.5 ± 3 | 1.5 ± 0.5 | 5.8 ± 3.5 | 2.2 ± 0.7 | 4.6 ± 1.9 | 2.7 ± 0.3 | 2.9 ± 1.3 |
| Endomorphin 1 | 4.2 ± 2.5 | 3.9 ± 3 | 7.7 ± 3.3 | 3.8 ± 1.3 | 11.5 ± 0.1 | 4.9 ± 2.5 | 9.9 ± 4 | 4.6 ± 0.5 | 5.1 ± 2 |
| Endomorphin 2 | 34.1 ± 25.4 | 4.6 ± 1.3 | 5.6 ± 3 | 5.4 ± 1.1 | 19.9 ± 2.2 | 6.3 ± 2.5 | 22.5 ± 3.4 | 9.6 ± 5.2 | 9.4 ± 5.1 |
| β-Endorphin | 3.5 ± 0.1 | 4.3 ± 2.2 | 6.6 ± 2.9 | 7.8 ± 2.7 | 24.7 ± 8.8 | 8.2 ± 3.8 | 16 ± 0.7 | 10 ± 5.8 | 8.4 ± 3 |
| Dynorphin A | 8.6 ± 0.3 | 47.4 ± 9.6 | 8.4 ± 1.9 | 19.3 ± 11.4 | 49 ± 38.5 | 13.8 ± 4 | 70.5 ± 51.1 | 52.7 ± 39.3 | 24.7 ± 22.5 |
| DPDPE | >500 | >500 | >500 | >500 | >500 | >500 | >500 | >500 | >500 |
| U50, 488H | >500 | >500 | >500 | >500 | >500 | >500 | >500 | >500 | >500 |

TABLE 4

| Clone | $K_D$ (nM) | $B_{max}$ (pmol/mg protein) |
|---|---|---|
| rMOR-1 | 2.8 ± 0.79 | 2.94 ± 0.45 |
| rMOR-1 no E 4 | 4.5 ± 1.1 | 0.39 ± 0.06 |
| rMOR-1A | 2.5 ± 0.2 | 0.81 ± 0.06 |
| rMOR-1C1 | 4.8 ± 0.6 | 1.82 ± 0.29 |
| rMOR-1D | 4.7 ± 1.2 | 0.51 ± 0.05 |

TABLE 5

| (% Maximal Inhibition) | DAMGO | Morphine | B-Endorphin |
|---|---|---|---|
| hMOR-1 | 84 | 89 | 88 |
| hMOR-1 (exons 1-3) | 81 | 83 | 81 |
| hMOR-1A | 90 | 92 | 81 |
| hMOR-1B1 | 63 | 76 | 72 |
| hMOR-1B2 | 99 | 98 | 72 |
| hMOR-1B3 | 80 | 51 | 81 |
| hMOR-1B4 | 71 | 76 | 77 |
| hMOR-1B5 | 91 | 86 | 77 |
| hMOR-1Y | 100 | 100 | 100 |

TABLE 6

| | DAMGO | | | Morphine | | | β-Endorphin | | |
|---|---|---|---|---|---|---|---|---|---|
| Ligand | $IC_{50}$ | $IC_{50}/K_i$ | Max Inhib (%) | $IC_{50}$ | $IC_{50}/K_i$ | Max Inhib (%) | $IC_{50}$ | $IC_{50}/K_i$ | Max Inhib (%) |
| hMOR-1 | 2 ± 0 | 1.0 | 76 ± 4 | 4 ± 1 | 0.9 | 74 ± 6 | 13 ± 3 | 0.3 | 79 ± 2 |
| hMOR-1 (exons 1-3) | 3 ± 1 | 2.0 | 74 ± 3 | 5 ± 1 | 1.7 | 69 ± 6 | 16 ± 4 | 3.7 | 73 ± 4 |
| hMOR-1A | 5 ± 2 | 2.1 | 82 ± 1 | 9 ± 3 | 2.0 | 76 ± 1 | 22 ± 3 | 3.3 | 73 ± 2 |
| hMOR-1B1 | 46 ± 17 | 38.3 | 57 ± 2 | 47 ± 19 | 19.6 | 63 ± 2 | 34 ± 4 | 4.4 | 65 ± 4 |
| hMOR-1B2 | 29 ± 7 | 5.0 | 90 ± 3 | 72 ± 16 | 6.4 | 81 ± 1 | 108 ± 34 | 4.4 | 65 ± 5 |
| hMOR-1B3 | 38 ± 7 | 21.1 | 73 ± 8 | 11 ± 4 | 3.4 | 42 ± 1 | 48 ± 12 | 5.9 | 73 ± 9 |
| hMOR-1B4 | 20 ± 3 | 8.7 | 65 ± 3 | 8 ± 2 | 1.5 | 63 ± 2 | 60 ± 16 | 3.8 | 69 ± 5 |
| hMOR-1B5 | 34 ± 5 | 16.1 | 83 ± 1 | 19 ± 2 | 4.9 | 71 ± 1 | 217 ± 50 | 21.7 | 69 ± 8 |
| hMOR-1Y | 8 ± 2 | 3.2 | 91 ± 2 | 9 ± 2 | 2.1 | 83 ± 3 | 44 ± 16 | 5.2 | 90 ± 2 |

Characterization of expressed variants. In order to study pharmacological functions of the variants, CHO cell lines stably transfected with individual variant cDNAs whose expression was under control of a human cytomegalovirus (CMV) early promoter, a common promoter used in mammalian expression system, were obtained. As a control, a stable cell line expressing a receptor that only contained exons 1-3 without a fourth exon was included. In saturation studies, [³H]DAMGO revealed high affinity for all the variants with little difference among their $K_D$ values (Table 2). Competition studies with a variety of opioids further demonstrated that all the variants encoded a mu opioid receptor (Table 3). The mu ligands such as DAMGO, morphine and M6G all competed binding with high affinities, while the delta-selective ligand DPDPE and the kappa₁-selective opioid, U50, 488H were inactive. The control receptor (hMOR-1 (exons 1-3)) showed a high affinity toward [3H]DAMGO in saturation studies and the similar mu-selective binding profile in competition studies, suggesting that the ligand binding was not very dependent on the carboxyl termini encoded by the different fourth exons. It was not surprising because they all had the same N-terminal seven transmembrane structure that comprises binding motifs for mu ligands. However, the variants did display subtle but significant binding pocket differences. For example, endomorphin 2 competed binding to the hMOR-1 over 5- to 7-fold less potently than against hMOR-1A, hMOR-1B1, hMOR-1B3 and hMOR-1 (exons 1-3) (p<0.05), respectively. β-endorphin showed lower affinities toward hMOR-1B2 and hMOR-1B4 as compared to other variants. Interestingly, compared to the other variants, hMOR-1B2 had relative lower affinities for all the mu agonists including DAMGO, morphine, M6G and endomorphin 1, but maintained a high affinity for naloxone. The carboxyl terminal sequence of hMOR-1B2 which encoded by exon 5b was quite unique with four basic residues in a total of nine amino acids. It also contained a potential cAMP- and cGMP-dependent protein kinase phosphorylation site.

Since the structures of all the variants differ from each other only at their carboxyl termini which are all located at intracellular side, there may be differences in their coupling to G protein transduction pathway. Mu opioid receptors are mainly coupled to Gi/Go and associated with inhibition of adenylyl cyclase to reduce the intracellular level of cAMP, an important second messenger system within cells. The effect of several opioids on forskolin-stimulated cAMP accumulation in intact cells expressing the variants was investigated.

The results showed striking differences in the effect of opioids on inhibiting cAMP production (Tables 3 and 4). This could be seen in both their potency determined by the $IC_{50}$ values, and efficacy indicated by the percentage of maximal inhibition. DAMGO and morphine, which displayed the limited differences among the variants in binding assays, revealed their $IC_{50}$ values that varied from 3- to 23-fold. β-endorphin $IC_{50}$ values also differed from 3- to 16-fold. The ratio of the $IC_{50}/Ki$ values that takes account for binding affinities of the opioids is another measurement for comparing their potencies. Again, there were marked differences of potencies among the variants. For example, the DAMGO $IC_{50}/Ki$ value for hMOR-1B1 was over 38-fold than that for hMOR-1. Although β-endorphin $IC_{50}$ value varied over 16-fold between hMOR-1 and hMOR-1B5, their $IC_{50}/Ki$ value differed by over 72-fold. Therefore, different carboxyl termini can indeed affect the potency of opioids to inhibit forskolin-stimulated cAMP accumulation in intact cells independent of their binding affinities.

Marked differences in the maximal inhibition (%), an indication of the opioid efficacy, were also observed among the variants (Tables 3 and 4). The ranges of the maximal inhibitions for DAMGO, morphine and β-endorphin were 63-100%, 51-100% and 72-100%, respectively (Table 5). Interestingly, hMOR-1Y had the highest efficacy for all the opioids, whereas the lowest efficacies for the opioids varied among the variants. hMOR-1B1 showed the lowest efficacy (63%) for DAMGO, while hMOR-1B1 and hMOR-1B2 had the lowest efficacy (72%) for morphine. hMOR-1B3 displayed only 51% of efficacy. There was little correlation between their potencies and efficacies. For example, morphine had the same efficacy for hMOR-1B1 and hMOR-1B4, but there was a 13-fold difference in their $IC_{50}/Ki$ values. On the other hand, in binding assays hMOR-1B2 had relatively low affinities toward DAMGO and morphine, but both opioids showed higher efficacies for hMOR-1B2, when compared to those for other variants. It also was interesting to observe that the relative efficacy of the different opioids for an individual variant varied (Table 5). For example, DAMGO and morphine were more efficacious than α-endorphin against hMOR-1B2, while β-endorphin and DAMGO were more effective than morphine against hMOR-1B3.

There was no association between binding affinity and potency or efficacy among the human variants for a number of drugs, which was similar to results obtained from the mouse MOR-1 variants by using the [$^{35}$S]GTP(S binding assay (see, e.g., Bolan et al. (2000) Soc. Neurosci. 26, 112), which is another method for assessing receptor signalling. Although different human variants often bind the same ligand equally well, the functional consequences, as indicated by their abilities to inhibit forskolin-stimulated cAMP accumulation, were distinct from each other. One implication of these studies is to potentially develop selective drugs based upon their efficacy and/or potency.

Together with the hMOR-1A, hMOR-1O and hMOR-1X variants previously isolated, there now are a total of nine human splice variants. The extensive alternative splicing first demonstrated in mouse now applies to human. All the nine variants were carboxyl terminal variants resulted from alternative splicing of the fourth exon. The different protein structures at their carboxyl tips had the limited effect on the binding selectivity of the variants, but all dramatically altered signaling thought through their interaction with G protein system. This dissociation of binding affinity and efficacy or potency for the variants, together with their potential region-specific expression, may provide insight to understand different pain thresholds and different opioid responses in human, and to design novel selective or individualized drugs that modulate pain based upon their efficacy/potency.

EXAMPLE 2

Identification and Characterization of Five New Splice Variants (rMOR-1C1, rMOR-1C2, rMOR-1D, rMOR-1B2, and rMOR-1E) of the rat Oprm Gene Five splice variants (rMOR-1C1, rMOR-1C2, rMOR-1D, rMOR-1B2, and rMOR-1E) of the rat Oprm gene from rat brain have been identified. The main strategy used for isolating the human and rat variants was to search the homologous variants in rat using the mouse variant sequences either by comparing with public rat genome databases (NBCI and Ensembl) or by directly using the mouse sequences to perform RT-PCT. All the rat variants contained the same exons 1, 2 and 3 as their original MOR-1, but had a different fourth exon. Therefore, all of the variants are carboxyl terminal variants. Although the variants were obtained by using the mouse sequences and shared some degree of homology at nucleotide level with the mouse sequences, all the predicted amino acid sequences from the alternative fourth exons were totally different from any of the mouse sequences identified so far. Northern blot analysis with appropriate exon probes revealed distinct band patterns with different sizes and intensities.

The variants were expressed in CHO cells and characterized them by opioid binding, [$^{35}$S]GTP-γ-S binding and adenylyl cyclase assays. The binding results showed that all the variants had higher affinity to mu-specific opioids and lower affinity to kappa or delta drugs, a similar profile revealed by the original MOR-1. This could be seen in both their potency determined by the $IC_{50}$ values, and efficacy indicated by the percentage of maximal inhibition. The results from [$^{35}$S]GTP-γ-S binding assay of the rat variants revealed marked differences in the ability of the opioids to stimulate [$^{35}$S]GTP-Y—S binding in terms of both their potency determined by the $EC_{50}$ and efficacy indicated as maximal stimulation. The different protein structures at carboxyl tips among the variants had the limited effect on their binding selectivity, but they do affect forskolin-stimulated adenylyl cyclase activity, presumably through their interaction with G proteins, as well as [$^{35}$S]GTP-γ-S binding. This dissociation of binding affinity and efficacy or potency for the variants, together with their potential region-specific expression, may provide an important insight to understand different pain thresholds and different opioid responses in human and rat, and to design novel selective or individualized drugs that modulate pain based upon their efficacy/potency.

Table 7 presents the selectivity of rMOR-1 splice variants in [$^3$H]DAMGO binding assay. Competition studies were performed in [$^3$H]DAMGO (~1 nM) binding assay using at least three concentrations of the indicated ligand with membranes from the same stable transfectant. ANOVA was performed, followed by Tukey's post hoc analysis. Results are the mean ±S.E. of at least three independent determinations.

Table 8 depicts the effects of opioid on [$^{35}$S]GTPγS binding in the rat MOR-1 splice variants. Basal [$^{35}$S]GTPγS binding was assessed in membranes from cells stably transfected with the individual variants. The ability multiple concentrations of the indicated opioid to stimulate [$^{35}$S]GTPγS binding was determined. The maximal stimulation was defined as the percent increase over basal binding, and the dose of drug needed to elicit 50% of the maximal response, the EC50. Results are the means ±S.E.M. of at least three independent determinations.

TABLE 7

| | Ki Value (nM) | | | | | Tukey | |
|---|---|---|---|---|---|---|---|
| | rMOR-1 | | | | | | |
| Ligand | rMOR-1 | (no E4) | rMOR-1A | rMOR-1C1 | rMOR-1D | ANOVA rMOR | p |
| Morphine | 5.6 ± 0.8 | 6.5 ± 0.6 | 8.0 ± 0.4 | 7.4 ± 0.3 | 7.4 ± 0.5 | N.S. | |
| M6G | 16.9 ± 2.2 | 20.5 ± 2.8 | 25.7 ± 2.1 | 24.8 ± 2.4 | 21.0 ± 1.8 | N.S. | |
| DAMGO | 3.3 ± 0.6 | 2.4 ± 0.4 | 6.0 ± 0.9 | 4.5 ± 0.9 | 4.7 ± 1.2 | N.S. | |
| DADLE | 4.3 ± 0.5 | 6.8 ± 1.3 | 8.1 ± 0.4 | 8.6 ± 1.0 | 5.4 ± 0.3 | N.S. | |
| DSLET | 30.9 ± 1.9 | 24.2 ± 1.9 | 44.5 ± 5.1 | 45.0 ± 8.7 | 27.3 ± 7.3 | N.S. | |

TABLE 7-continued

| | Ki Value (nM) | | | | | | Tukey | |
|---|---|---|---|---|---|---|---|---|
| | rMOR-1 | | | | | | | |
| Ligand | rMOR-1 | (no E4) | rMOR-1A | rMOR-1C1 | rMOR-1D | ANOVA | rMOR | p |
| Endomorphin 1 | 4.1 ± 0.7 | 4.4 ± 0.1 | 6.5 ± 0.3 | 3.9 ± 0.1 | 3.9 ± 0.4 | <0.05 | 1 vs 1A | <0.05 |
| | | | | | | | 1A vs 1C1 | <0.05 |
| | | | | | | | 1A vs 1C2 | <0.05 |
| Endomorphin 2 | 8.0 ± 2.0 | 9.1 ± 0.7 | 11.5 ± 0.6 | 10.1 ± 0.6 | 7.5 ± 0.4 | N.S. | | |
| β-Endorphin | 3.7 ± 0.4 | 10.0 ± 0.8 | 10.5 ± 0.6 | 8.8 ± 0.5 | 8.5 ± 0.6 | <0.0005 | 1 vs 1(no E4) | <0.001 |
| | | | | | | | 1 vs 1A | <0.001 |
| | | | | | | | 1 vs 1C1 | <0.01 |
| | | | | | | | 1 vs 1C2 | <0.01 |
| Dynorphin A | 12.4 ± 3.0 | 14.0 ± 1.4 | 22.8 ± 1.6 | 12.5 ± 2.3 | 10.8 ± 1.7 | <0.05 | 1A vs 1C2 | <0.05 |
| Naloxone | 3.2 ± 0.4 | 4.1 ± 0.4 | 5.0 ± 0.9 | 5.4 ± 0.9 | 2.6 ± 0.8 | N.S. | | |
| U50, 488H | >500 | >500 | >500 | >500 | >500 | | | |
| DPDPE | >500 | >500 | >500 | >500 | >500 | | | |

TABLE 8

| | rMOR-1 | | | rMOR-1 (no Exon 4) | | | rMOR-1A | | |
|---|---|---|---|---|---|---|---|---|---|
| Ligand | EC50 (nM) | EC50/ Ki | Max Stim (%) | EC50 (nM) | EC50/ Ki | Max Stim (%) | EC50 (nM) | EC50/ Ki | Max Stim (%) |
| DAMGO | 12 ± 3 | 3.6 | 233 ± 44 | 86 ± 16 | 35.8 | 196 ± 37 | 13 ± 5 | 2.2 | 176 ± 24 |
| DADLE | 24 ± 5 | 5.6 | 298 ± 26 | 401 ± 38 | 59.0 | 225 ± 24 | 63 ± 23 | 7.8 | 175 ± 8 |
| DSLET | 76 ± 17 | 2.5 | 251 ± 5 | 690 ± 179 | 28.5 | 226 ± 15 | 127 ± 45 | 2.9 | 206 ± 23 |
| Endomorphine1 | 14 ± 4 | 3.4 | 320 ± 23 | 114 ± 11 | 25.9 | 189 ± 16 | 15 ± 3 | 2.3 | 205 ± 34 |
| β-Endorphin | 4 ± 2 | 1.1 | 246 ± 52 | 90 ± 20 | 9.0 | 240 ± 16 | 13 ± 5 | 1.2 | 177 ± 28 |

| | rMOR-1C1 | | | rMOR-1D | | |
|---|---|---|---|---|---|---|
| Ligand | EC50 (nM) | EC50/ Ki | Max Stim (%) | EC50 (nM) | EC50/ Ki | Max Stim (%) |
| DAMGO | 4 ± 22 | 16.4 | 233 ± 45 | 125 ± 26 | 26.6 | 113 ± 22 |
| DADLE | 128 ± 15 | 14.8 | 379 ± 62 | 300 ± 29 | 55.6 | 204 ± 23 |
| DSLET | 253 ± 75 | 5.6 | 312 ± 19 | 540 ± 129 | 19.7 | 187 ± 19 |
| Endomorphine1 | 54 ± 8 | 13.8 | 377 ± 40 | 100 ± 26 | 25.6 | 145 ± 29 |
| β-Endorphin | 48 ± 4 | 5.5 | 361 ± 41 | 91 ± 14 | 10.7 | 165 ± 42 |

All references cited herein, are hereby incorporated herein. Although the foregoing invention has been described in some detail, by way of illustration and example for the purposes of clarity and understanding, it will be apparent to those skilled in the art that certain changes and modifications can be practice. Therefore, the description and examples should not be construed as limiting the scope of the invention, which is delineated by the appended claims and/or claims.

We claim:

1. An isolated hMOR-1B1 splice variant polypeptide that consists essentially of the amino acid residues having the sequence of SEQ ID NO: 51.

2. An isolated hMOR-1B2 splice variant polypeptide that consists essentially of the amino acid residues having the sequence of SEQ ID NO: 53.

3. An isolated hMOR-1B3 splice variant polypeptide that consists essentially of the amino acid residues having the sequence of SEQ ID NO: 55.

4. An isolated hMOR-1B4 splice variant polypeptide that consists essentially of the amino acid residues having the sequence of SEQ ID NO: 57.

5. An isolated hMOR-1B5 splice variant polypeptide that consists essentially of the amino acid residues having the sequence of SEQ ID NO: 59.

6. An isolated hMOR-1Y splice variant polypeptide that consists essentially of the amino acid residues having the sequence of SEQ ID NO: 61.

7. A homodimer or heterodimer consisting of two polypeptides having sequences selected from the group consisting of SEQ ID NOs: 51, 53, 55, 57, 59, and 61.

8. An isolated polynucleotide consisting essentially of hMOR-1B1 having the sequence of SEQ ID NO: 50 or a polynucleotide that is filly complementary thereto.

9. An isolated polynucleotide consisting essentially of hMOR-1B2 having the sequence of SEQ ID NO: 52 or a polynucleotide that is fully complementary thereto.

10. An isolated polynucleotide consisting essentially of hMOR-1B3 having the sequence of SEQ ID NO: 54 or a polynucleotide that is fully complementary thereto.

11. An isolated polynucleotide consisting essentially of hMOR-1B4 having the sequence of SEQ ID NO: 56 or a polynucleotide that is fully complementary thereto.

12. An isolated polynucleotide consisting essentially of hMOR- 1B5 having the sequence of SEQ ID NO: 58.

13. An isolated polynucleotide consisting essentially of hMOR-1Y having the sequence of SEQ ID NO: 60 or a polynucleotide that is fully complementary thereto.

14. A method of screening compositions for opioid activity comprising the steps of: a) contacting a cell comprising an MOR-1 splice variant polypeptide selected from the group consisting of SEQ ID NOs: 51, 53, 55, 57, 59, and 61 with a composition in an amount sufficient to exert a physiologic effect and an opioid in an amount sufficient to exert a physiologic effect; b) measuring the physiologic effect of the composition and the opioid on the cell, relative to their effects on a control cell lacking the MOR-1 splice variant polypeptide, where determination of a physiologic effect of the composition is expressed relative to the physiologic effect of the opioid.

15. The method according to claim 14, where the composition is selected from the group consisting of synthetic combinatorial libraries of small molecule ligands, eukaryotic whole cell lysates or extracts, or media conditioned by cultured eukaryotic cells.

16. The method according to claim 14, where the opioid is selected from the group consisting of morphine, methadone, etorphine, levorphanol, fentanyl, sufentanil, [D-Ala2,Me-Phe4,Gly(ol)5]enkephalin, pentazocine, ethylketocyclazocine, bremazocine, spiradoline, [D-Ser2,Leu5]enkephalin-Thr6, Met-enkephalin, Leu-enkephalin, (3-endorphin, dynorphin A, dynorphin B, or a-neoendorphin.

17. The method according to claim 14, wherein the physiological effect is assayed by detecting a hormone is selected from the group consisting of prolactin, growth hormone, gonadoftopin-releasing hormone, adrenocorticotropin, corticotropin-releasing factor, luteinizing hormone, follicle stimulating hormone, testosterone or cortisol.

18. A method of screening compositions for opioid binding activity comprising the steps of: a) contacting an MOR-1 splice variant polypeptide selected from the group consisting of SEQ ID NOs: 51, 53, 55, 57, 59, and 61, with a composition and an opioid: b) measuring binding of the composition and the opioid to said MOR-1 splice variant polypeptide; and c) comparing MOR-1 splice variant polypeptide binding of the composition to MOR-1 spike variant polypeptide binding to the opioid, where determination of binding of the composition is expressed relative to that of the opioid.

19. The method according to claim 18, where the composition is selected from the group consisting of synthetic combinatorial libraries of small molecule ligands, eukaryotic whole cell lysates or extracts, or media conditioned by cultured eukaryotic cells.

* * * * *

UNITED STATES PATENT AND TRADEMARK OFFICE
CERTIFICATE OF CORRECTION

| | | |
|---|---|---|
| PATENT NO. | : 7,585,941 B2 | Page 1 of 1 |
| APPLICATION NO. | : 10/588679 | |
| DATED | : September 8, 2009 | |
| INVENTOR(S) | : Gavril W. Pasternak | |

It is certified that error appears in the above-identified patent and that said Letters Patent is hereby corrected as shown below:

Specification

In column 1, beginning at line 35 and ending at line 43, please delete:

"This work was supported by the government, in part, by grants from the National Institute on Drug Abuse (DA02615 and DA07241); a Senior Scientist Award (DA00220) to Gavril W. Pasternak; a research grant (DA13997) to Ying-Xian Pan; a grant from the National Genetics Foundation; and a core grant to Memorial Sloan-Kettering Cancer Center, New York, N.Y. (CA08748) from the National Cancer Institute. The government may have certain rights to this invention."

and insert:

-- This invention was made with US government support under grant numbers: DA000220, DA002615, DA007241, DA013997 awarded by National Institutes of Health. The US government has certain rights in the invention. --

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 89

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcttccaatc ttatattctt tcacgg                                           26

<210> SEQ ID NO 2
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
gaaaggaagc ggctgaggcg ct                                               22

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtgtattgtc tattagagtg aggctaacat ttctttgg                              38

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacacggca gtaccttctc ttggtctcc                                        29

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggtgctcct ggctacctcg ca                                               22

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggttagatgg cttttatcat catattgctg g                                     31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggaacagga attttagggt tcatgtcata g                                     31

<210> SEQ ID NO 8
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
gcttcccctc ttccctccat tctc                                            24

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 ggattaaaact cctagtttag cacaaagcc                                      29

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccaccagta ccctgccctt cc                                              22

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcaatgttg gaagaggttg ggatac                                          26

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtacgcagtc tctagaatta ggtatatcta ctg                                  33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggattctaga tcagaattat ttctataatg tgc                                  33

<210> SEQ ID NO 14
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 14
gagaccaccc ctccacggc                                                 19

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtctccatt agggctagca gcag                                           24

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagagagaaa gaagacagaa atctgactgg taag                                34

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagagcacgt gttgaaactg caagtcagag                                     30

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggacctccag ccaagtttgt tgctgac                                        27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctctctgtgc aaacggttga atgaatgg                                       28

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cagagctgac tatgacatga accctaaaat tcctg                                35

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtccctgaa accaacaaaa aaactggatg                                      30

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caggtggaat tgaacctgga ctgtcactgt g                                    31

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctctaaaaa tcatatgaaa tagttacaag cctttg                               36

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
catcagatca gagatccaat atcaaacctt ccc                                  33

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggaggtccct tgataactgc caaatcgc                                        28

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 26
gatctcgagt cattactgat gattagttct atccactgta ttggc              45

<210> SEQ ID NO 27
<211> LENGTH: 8
<212> TYPE: PRT
<213> ORGANISM: Homo sapiens

<400> SEQUENCE: 27

Thr Asn His Gln Val Arg Ser Leu
 1               5

<210> SEQ ID NO 28
<211> LENGTH: 136
<212> TYPE: DNA
<213> ORGANISM: Homo sapiens
<220> FEATURE:
<221> NAME/KEY: CDS
<222> LOCATION: (1)..(24)

<400> SEQUENCE: 28 act aat cat cag gta cgc agt ctc tagaattagg tatatctact ggggatgaca    54
Thr Asn His Gln Val Arg Ser Leu
 1               5 taaaaattat aaggctttgt gctaaactag gagtttaatc cattatagag gatgagaatg  114
gagggaagag gggaagcaag gg                                          136

<210> SEQ ID NO 29
<211> LENGTH: 22
<212> TYPE: PRT
<213> ORGANISM: Homo sapiens

<400> SEQUENCE: 29

Thr Asn His Gln Lys Ile Asp Leu Phe Gln Lys Ser Ser Leu Leu Asn
 1               5                  10                  15

Cys Glu His Thr Lys Gly
            20

<210> SEQ ID NO 30
<211> LENGTH: 111
<212> TYPE: DNA
<213> ORGANISM: Homo sapiens
<220> FEATURE:
<221> NAME/KEY: CDS
<222> LOCATION: (1)..(66)

<400> SEQUENCE: 30 act aat cat cag aaa ata gat tta ttt caa aag tca tct tta ctc aac    48
Thr Asn His Gln Lys Ile Asp Leu Phe Gln Lys Ser Ser Leu Leu Asn
 1               5                  10                  15 tgt gag cat acc aag ggc taataattac aatattttcc cgtgaaagaa            96
Cys Glu His Thr Lys Gly
            20 tataagattg gaagc                                                  111

<210> SEQ ID NO 31
<211> LENGTH: 13
<212> TYPE: PRT
<213> ORGANISM: Homo sapiens

<400> SEQUENCE: 31

Thr Asn His Gln Arg Glu Arg Arg Gln Lys Ser Asp Trp
```

```
<210> SEQ ID NO 32
<211> LENGTH: 138
<212> TYPE: DNA
<213> ORGANISM: Homo sapiens
<220> FEATURE:
<221> NAME/KEY: CDS
<222> LOCATION: (1)..(39)

<400> SEQUENCE: 32 act aat cat cag aga gaa aga aga cag aaa tct gac tgg taagaaattg      49
Thr Asn His Gln Arg Glu Arg Arg Gln Lys Ser Asp Trp
 1               5                  10 ttacccttt tgccagcatgc caggcttctg ggttcccttt ccctgagcgg ccctagtgat   109
ccggcttgcg gcaccatcgc ctacgggcc                                     138

<210> SEQ ID NO 33
<211> LENGTH: 19
<212> TYPE: PRT
<213> ORGANISM: Homo sapiens

<400> SEQUENCE: 33

Thr Asn His Gln Gly Pro Pro Ala Lys Phe Val Ala Asp Gln Leu Ala
 1               5                  10                  15

Gly Ser Ser

<210> SEQ ID NO 34
<211> LENGTH: 142
<212> TYPE: DNA
<213> ORGANISM: Homo sapiens
<220> FEATURE:
<221> NAME/KEY: CDS
<222> LOCATION: (1)..(57)

<400> SEQUENCE: 34 act aat cat cag gga cct cca gcc aag ttt gtt gct gac caa ctt gcc     48
Thr Asn His Gln Gly Pro Pro Ala Lys Phe Val Ala Asp Gln Leu Ala
 1               5                  10                  15 ggg tcg tct tgaaaagggg gcttacaggt gttccaagcc cgtgttttat              97
Gly Ser Ser cctgaagtat ccctcaacac agaaaaacga cctcataaca caaaa                    142

<210> SEQ ID NO 35
<211> LENGTH: 49
<212> TYPE: DNA
<213> ORGANISM: Homo sapiens
<220> FEATURE:
<221> NAME/KEY: CDS
<222> LOCATION: (1)..(15)

<400> SEQUENCE: 35 act aat cat cag agc tgactatgac atgaacccta aaattcctgt tccc            49
Thr Asn His Gln Ser
 1               5

<210> SEQ ID NO 36
<211> LENGTH: 5
<212> TYPE: PRT
<213> ORGANISM: Homo sapiens

<400> SEQUENCE: 36

Thr Asn His Gln Ser
 1               5
```

<210> SEQ ID NO 37
<211> LENGTH: 118
<212> TYPE: DNA
<213> ORGANISM: Homo sapiens
<220> FEATURE:
<221> NAME/KEY: CDS
<222> LOCATION: (1)..(78)

<400> SEQUENCE: 37

```
act aat cat cag gtg gaa ttg aac ctg gac tgt cac tgt gaa aat gca      48
Thr Asn His Gln Val Glu Leu Asn Leu Asp Cys His Cys Glu Asn Ala
 1               5                  10                  15 aag cct tgg cca ctg agc tac aat gca ggg tagtctccat ttcccttccc       98
Lys Pro Trp Pro Leu Ser Tyr Asn Ala Gly
             20                  25 aggaagagtc tagagcgtta                                              118
```

<210> SEQ ID NO 38
<211> LENGTH: 26
<212> TYPE: PRT
<213> ORGANISM: Homo sapiens

<400> SEQUENCE: 38

```
Thr Asn His Gln Val Glu Leu Asn Leu Asp Cys His Cys Glu Asn Ala
 1               5                  10                  15

Lys Pro Trp Pro Leu Ser Tyr Asn Ala Gly
             20                  25
```

<210> SEQ ID NO 39
<211> LENGTH: 18
<212> TYPE: PRT
<213> ORGANISM: Homo sapiens

<400> SEQUENCE: 39

```
Thr Asn His Gln Ile Arg Asp Pro Ile Ser Asn Leu Pro Arg Val Ser
 1               5                  10                  15

Val Phe
```

<210> SEQ ID NO 40
<211> LENGTH: 142
<212> TYPE: DNA
<213> ORGANISM: Homo sapiens
<220> FEATURE:
<221> NAME/KEY: CDS
<222> LOCATION: (1)..(54)

<400> SEQUENCE: 40

```
act aat cat cag atc aga gat cca ata tca aac ctt ccc agg gtg tct      48
Thr Asn His Gln Ile Arg Asp Pro Ile Ser Asn Leu Pro Arg Val Ser
 1               5                  10                  15 gta ttc tgacaactgt ccactgaggc aatttccata cagcgcaaag tggagtggcg     104
Val Phe atttggcagt atcaaggga cctccagcca agtttgtt                           142
```

<210> SEQ ID NO 41
<211> LENGTH: 12
<212> TYPE: PRT
<213> ORGANISM: Homo sapiens

<400> SEQUENCE: 41

```
Leu Glu Asn Leu Glu Ala Glu Thr Ala Pro Leu Pro
 1               5                  10
```

```
<210> SEQ ID NO 42
<211> LENGTH: 4
<212> TYPE: PRT
<213> ORGANISM: Homo sapiens

<400> SEQUENCE: 42

Val Arg Ser Leu
  1

<210> SEQ ID NO 43
<211> LENGTH: 18
<212> TYPE: PRT
<213> ORGANISM: Homo sapiens

<400> SEQUENCE: 43

Lys Ile Asp Leu Phe Gln Lys Ser Ser Leu Leu Asn Cys Glu His Thr
  1               5                  10                  15

Lys Gly

<210> SEQ ID NO 44
<211> LENGTH: 9
<212> TYPE: PRT
<213> ORGANISM: Homo sapiens

<400> SEQUENCE: 44

Arg Glu Arg Arg Gln Lys Ser Asp Trp
  1               5

<210> SEQ ID NO 45
<211> LENGTH: 15
<212> TYPE: PRT
<213> ORGANISM: Homo sapiens

<400> SEQUENCE: 45

Gly Pro Pro Ala Lys Phe Val Ala Asp Gln Leu Ala Gly Ser Ser
  1               5                  10                  15

<210> SEQ ID NO 46
<211> LENGTH: 22
<212> TYPE: PRT
<213> ORGANISM: Homo sapiens

<400> SEQUENCE: 46

Val Glu Leu Asn Leu Asp Cys His Cys Glu Asn Ala Lys Pro Trp Pro
  1               5                  10                  15

Leu Ser Tyr Asn Ala Gly
              20

<210> SEQ ID NO 47
<211> LENGTH: 14
<212> TYPE: PRT
<213> ORGANISM: Homo sapiens

<400> SEQUENCE: 47

Ile Arg Asp Pro Ile Ser Asn Leu Pro Arg Val Ser Val Phe
  1               5                  10

<210> SEQ ID NO 48
<211> LENGTH: 30
<212> TYPE: PRT
<213> ORGANISM: Homo sapiens

<400> SEQUENCE: 48
```

```
Pro Pro Leu Ala Val Ser Met Ala Gln Ile Phe Thr Arg Tyr Pro Pro
 1               5                  10                  15
Pro Thr His Arg Glu Lys Thr Cys Asn Asp Tyr Met Lys Arg
            20                  25                  30

<210> SEQ ID NO 49
<211> LENGTH: 58
<212> TYPE: PRT
<213> ORGANISM: Homo sapiens

<400> SEQUENCE: 49

Cys Leu Pro Ile Pro Ser Leu Ser Cys Trp Ala Leu Glu His Gly Cys
 1               5                  10                  15
Leu Val Val Tyr Pro Gly Pro Leu Gln Gly Pro Leu Val Arg Tyr Asp
            20                  25                  30
Leu Pro Ala Ile Leu His Ser Ser Cys Leu Arg Gly Asn Thr Ala Pro
        35                  40                  45
Ser Pro Ser Gly Gly Ala Phe Leu Leu Ser
    50                  55

<210> SEQ ID NO 50
<211> LENGTH: 1354
<212> TYPE: DNA
<213> ORGANISM: Homo sapiens

<400> SEQUENCE: 50
cggaaaggaa gcggctgagg cgcttggaac ccgaaaagtc tcggtgctcc tggctacctc      60
gcacagcggt gcccgcccgg ccgtcagtac catggacagc agcgctgccc ccacgaacgc     120
cagcaattgc actgatgcct ggcgtactca agttgctccc cagcaccca gccccggttc     180
ctgggtcaac ttgtcccact agatggcaa cctgtccgac ccatgcggtc gaaccgcac      240
cgacctgggc gggagagaca gcctgtgccc tccgaccggc agtccctcca tgatcacggc     300
catcacgatc atggccctct actccatcgt gtgcgtggtg gggctcttcg aaacttcct     360
ggtcatgtat gtgattgtca gatacaccaa gatgaagact gccaccaaca tctacatttt     420
caaccttgct ctggcagatg ccttagccac cagtaccctg ccctttcaga gtgtgaatta     480
cctaatggga acatggccat ttggaaccat cctttgcaag atagtgatct ccatagatta     540
ctataacatg ttcaccagca tattcacccct ctgcaccatg agtgttgatc gatacattgc     600
agtctgccac cctgtcaagg ccttagattt ccgtactccc cgaaatgcca aaattatcaa     660
tgtctgcaac tggatcctct cttcagccat ggtcttcct gtaatgttca tggctacaac     720
aaaatacagg caaggttcca tagattgtac actaacattc tctcatccaa cctggtactg     780
ggaaaacctg ctgaagatct gtgttttcat cttcgccttc attatgccag tgctcatcat     840
taccgtgtgc tatggactga tgatcttgcg cctcaagagt gtccgcatgc tctctggctc     900
caaagaaaag gacaggaatc ttcgaaggat caccaggatg gtgctggtgg tggtggctgt     960
gttcatcgtc tgctggactc ccattcacat ttacgtcatc attaaagcct tggttacaat    1020
cccagaaact acgttccaga ctgtttcttg gcacttctgc attgctctag gttacacaaa    1080
cagctgcctc aacccagtcc tttatgcatt tctggatgaa acttcaaac gatgcttcag    1140
agagttctgt atcccaacct cttccaacat tgagcaacaa aactccactc gaattcgtca    1200
gaacactaga gaccaccccct ccacggccaa tacagtggat agaactaatc atcagaaaat    1260
agatttattt caaaagtcat ctttactcaa ctgtgagcat accaagggct aataattaca    1320
``` atatttccc gtgaaagaat ataagattgg aagc                                  1354

<210> SEQ ID NO 51
<211> LENGTH: 406
<212> TYPE: PRT
<213> ORGANISM: Homo sapiens

<400> SEQUENCE: 51

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

```
Arg Gln Asn Thr Arg Asp His Pro Ser Thr Ala Asn Thr Val Asp Arg
    370                 375                 380

Thr Asn His Gln Lys Ile Asp Leu Phe Gln Lys Ser Ser Leu Leu Asn
385                 390                 395                 400

Cys Glu His Thr Lys Gly
            405

<210> SEQ ID NO 52
<211> LENGTH: 2218
<212> TYPE: DNA
<213> ORGANISM: Homo sapiens

<400> SEQUENCE: 52
cggtgctcct ggctacctcg cacagcggtg cccgcccggc cgtcagtacc atggacagca      60
gcgctgcccc cacgaacgcc agcaattgca ctgatgcctt ggcgtactca agttgctccc     120
cagcacccag ccccggttcc tgggtcaact tgtcccactt agatggcaac ctgtccgacc     180
catgcggtcc gaaccgcacc gacctgggcg ggagagacag cctgtgccct ccgaccggca     240
gtccctccat gatcacggcc atcacgatca tggccctcta ctccatcgtg tgcgtggtgg     300
ggctcttcgg aaacttcctg gtcatgtatg tgattgtcag atacaccaag atgaagactg     360
ccaccaacat ctacattttc aaccttgctc tggcagatgc cttagccacc agtaccctgc     420
ccttccagag tgtgaattac ctaatgggaa catggccatt tggaaccatc ctttgcaaga     480
tagtgatctc catagattac tataacatgt tcaccagcat attcaccctc tgcaccatga     540
gtgttgatcg atacattgca gtctgccacc ctgtcaaggc cttagatttc cgtactcccc     600
gaaatgccaa aattatcaat gtctgcaact ggatcctctc ttcagccatt ggtcttcctg     660
taatgttcat ggctacaaca aaatacaggc aaggttccat agattgtaca ctaacattct     720
ctcatccaac ctggtactgg gaaaacctgc tgaagatctg tgttttcatc ttcgccttca     780
ttatgccagt gctcatcatt accgtgtgct atggactgat gatcttgcgc ctcaagagtg     840
tccgcatgct ctctggctcc aaagaaaagg acaggaatct tcgaaggatc accaggatgg     900
tgctggtggt ggtggctgtg ttcatcgtct gctggactcc cattcacatt tacgtcatca     960
ttaaagcctt ggttacaatc ccagaaacta cgttccagac tgtttcttgg cacttctgca    1020
ttgctctagg ttacacaaac agctgcctca acccagtcct ttatgcattt ctggatgaaa    1080
acttcaaacg atgcttcaga gagttctgta tcccaacctc ttccaacatt gagcaacaaa    1140
actccactcg aattcgtcag aacactagag accaccctc cacggccaat acagtggata    1200
gaactaatca tcagagagaa agaagacaga atctgactg gtaagaaatt gttacccttt    1260
tgccagcatg ccaggcttct gggttccctt ccctgagcg gccctagtga tccggcttgc    1320
ggcaccatcg cctacgggcc aagctgcatc ataaggaaa tttttttttt cattctggcc    1380
agagcaaaac acatgtgata aaacataggc attagctact ctgcttagca ccaaatatca    1440
gactagctta aatttgcccc cagatgggtt ccatcatctt taatccgacc tctgacttgc    1500
agtttcaaca cgtgctctct tgggcaaaac agttgcctg agtaacagaa agataggaa    1560
aggaaaagga gagagagaaa aatgtgccca gtggaagggt ggggaaggtg aaatgatcaa    1620
ggaggccaga gaaagactca cctattgcag caacactgta gaagttcagg cagctgcttc    1680
tcggtagcaa aaggatcttt tccagcaatc ctattagctc tcaagtttcc ccttttaggg    1740
aggaaaaagc tccccatgtc ccgcgatcct gtacatgtcc aaccctgcca tccacagccaa    1800
tcagcaaaga gtgcaagaca gattaatcca aagagaatag caattaatat cccatagcat    1860
```

-continued

```
caaagctgtt cttagccaag agggacttta acgggagggg tctctaacac cctaaatctt    1920
agaagagact ctaaccatcc taagtagggc ctctaaccccc gctttataaa cttttaattg   1980
actcccatct taacagttgc aatccatgga ggaatgcttg ataacctcgg tgataagata    2040
aaaaaccaag catactagaa gtgttctcta aaattaaaaa tacagtagtt gctagagaaa    2100
aattttagtc caaaaatcca actatagaaa catagaatgt gagaggtagc acataagaaa    2160
taagtcatgg ggatttttatt tcatggacca gcaatatgat gataaaagcc atctaacc    2218
```

<210> SEQ ID NO 53
<211> LENGTH: 397
<212> TYPE: PRT
<213> ORGANISM: Homo sapiens

<400> SEQUENCE: 53

```
Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320
```

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Arg Glu Arg Arg Gln Lys Ser Asp Trp
385                 390                 395

<210> SEQ ID NO 54
<211> LENGTH: 2483
<212> TYPE: DNA
<213> ORGANISM: Homo sapiens

<400> SEQUENCE: 54

| | | |
|---|---|---|
| cggtgctcct ggctacctcg cacagcggtg cccgcccggc cgtcagtacc atggacagca | 60 |
| gcgctgcccc cacgaacgcc agcaattgca ctgatgcctt ggcgtactca agttgctccc | 120 |
| cagcacccag ccccggttcc tgggtcaact tgtcccactt agatggcaac ctgtccgacc | 180 |
| catgcggtcc gaaccgcacc gacctgggcg ggagagacag cctgtgccct ccgaccggca | 240 |
| gtccctccat gatcacggcc atcacgatca tggccctcta ctccatcgtg tgcgtggtgg | 300 |
| ggctcttcgg aaacttcctg gtcatgtatg tgattgtcag atacaccaag atgaagactg | 360 |
| ccaccaacat ctacattttc aaccttgctc tggcagatgc cttagccacc agtaccctgc | 420 |
| ccttccagag tgtgaattac ctaatgggaa catggccatt tggaaccatc ctttgcaaga | 480 |
| tagtgatctc catagattac tataacatgt tcaccagcat attcaccctc tgcaccatga | 540 |
| gtgttgatcg atacattgca gtctgccacc ctgtcaaggc cttagatttc cgtactcccc | 600 |
| gaaatgccaa aattatcaat gtctgcaact ggatcctctc ttcagccatt ggtcttcctg | 660 |
| taatgttcat ggctacaaca aaatacaggc aaggttccat agattgtaca ctaacattct | 720 |
| ctcatccaac ctggtactgg gaaaacctgc tgaagatctg tgttttcatc ttcgccttca | 780 |
| ttatgccagt gctcatcatt accgtgtgct atggactgat gatcttgcgc ctcaagagtg | 840 |
| tccgcatgct ctctggctcc aaagaaaagg acaggaatct tcgaaggatc accaggatgg | 900 |
| tgctggtggt ggtggctgtg ttcatcgtct gctggactcc cattcacatt tacgtcatca | 960 |
| ttaaagcctt ggttacaatc ccagaaacta cgttccagac tgtttcttgg cacttctgca | 1020 |
| ttgctctagg ttacacaaac agctgcctca cccagtcct ttatgcattt ctggatgaaa | 1080 |
| acttcaaacg atgcttcaga gagttctgta tcccaacctc ttccaacatt gagcaacaaa | 1140 |
| actccactcg aattcgtcag aacactagag accacccctc cacggccaat acagtggata | 1200 |
| gaactaatca tcagggacct ccagccaagt tgttgctga ccaacttgcc gggtcgtctt | 1260 |
| gaaaaggggg cttacaggtg ttccaagccc gtgttttatc ctgaagtatc cctcaacaca | 1320 |
| gaaaaacgac ctcataacac aaaatacacc agcttaaaaa tagcctttga attattttc | 1380 |
| acattaatca aaactttaca gaggagataa acactgattt tttattttat tttattttat | 1440 |
| tttattttat tttattgcca ttcattcaac cgtttgcaca gagagaaaga agacagaaat | 1500 |
| ctgactggta agaaattgtt accctttgc cagcatgcca ggcttctggg ttccctttcc | 1560 |
| ctgagcggcc ctagtgatcc ggcttgcggc accatcgcct acgggccaag ctgcatcata | 1620 |
| aaggaaattt ttttttttcat tctggccaga gcaaaacaca tgtgataaaa cataggcatt | 1680 |

```
agctactctg cttagcacca aatatcagac tagcttaaat ttgccccag acgggttcca   1740 tcatctttaa tccgacctct gacttgcagt ttcaacacgt gctctctggg caaaacagtt   1800
gccctgagta acagaaaaga taggaaagga aaaggagaga gagaaaaacg tgccagtgga   1860
agggtgggga aggtgaaatg atcaaggagg ccagagaaag actcacctat tgcagcaaca   1920
ctgtagaagt tcaggcagct gcttctcggt agcaaaagga tcttttccag caatcctatt   1980
agctctcaag tttccccttt tagggaggaa aaagctcccc atgtcccgcg atcctgtaca   2040
tgtccaaccc tgccgtccac agccatcagc aaagagtgca agacagatta atccaaagag   2100
aatagcgatt aatatcccat agcatcaaag ctgttcttag ccaagaggga ctttaacgag   2160
aggggtctct aacaccctaa atcttagaag agactctaac catcctaagt agggcctcta   2220
accccgcttt ataaactttt aattgactcc atcttaaca gttgcaatcc atggaggaat   2280
gcttgataac ctcggtgata agataaaaaa ccaagcatac tagaagtgtt ctctaaaatt   2340
aaaaatacag tagttgctag agaaaaattt tagtccaaaa atccaactat agaaacatag   2400
aatgtgagag gcagcacata agaaataagt catggggatt ttatttcatg gaccagcaat   2460
atgatgataa aagccatcta acc                                           2483
```

<210> SEQ ID NO 55
<211> LENGTH: 403
<212> TYPE: PRT
<213> ORGANISM: Homo sapiens

<400> SEQUENCE: 55

```
Met Asp Ser Ser Ala Ala Pro Thr Asn Ala Ser Asn Cys Thr Asp Ala
  1               5                  10                  15

Leu Ala Tyr Ser Ser Cys Ser Pro Ala Pro Ser Pro Gly Ser Trp Val
             20                  25                  30

Asn Leu Ser His Leu Asp Gly Asn Leu Ser Asp Pro Cys Gly Pro Asn
         35                  40                  45

Arg Thr Asp Leu Gly Gly Arg Asp Ser Leu Cys Pro Pro Thr Gly Ser
     50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220
```

-continued

```
His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
        260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
        340                 345                 350

Cys Ile Pro Thr Ser Ser Asn Ile Glu Gln Gln Asn Ser Thr Arg Ile
    355                 360                 365

Arg Gln Asn Thr Arg Asp His Pro Ser Thr Ala Asn Thr Val Asp Arg
370                 375                 380

Thr Asn His Gln Gly Pro Pro Ala Lys Phe Val Ala Asp Gln Leu Ala
385                 390                 395                 400

Gly Ser Ser
```

<210> SEQ ID NO 56
<211> LENGTH: 1251
<212> TYPE: DNA
<213> ORGANISM: Homo sapiens

<400> SEQUENCE: 56

```
cggtgctcct ggctacctcg cacagcggtg cccgcccggc cgtcagtacc atggacagca      60
gcgctgcccc cacgaacgcc agcaattgca ctgatgcctt ggcgtactca agttgctccc     120
cagcacccag cccggttcc tgggtcaact tgtcccactt agatggcaac ctgtccgacc     180
catgcggtcc gaaccgcacc gacctgggcg ggagagacag cctgtgccct ccgaccggca     240
gtccctccat gatcacggcc atcacgatca tggccctcta ctccatcgtg tgcgtggtgg     300
ggctcttcgg aaacttcctg gtcatgtatg tgattgtcag atacaccaag atgaagactg     360
ccaccaacat ctacgttttc aaccttgctc tggcagatgc cttagccacc gtaccctgc     420
ccttccagag tgtgaattac ctaatgggaa catggccatt ggaaccatc ctttgcaaga     480
tagtgatctc catagattac tataacatgt tcaccagcat attcacccte tgcaccatga     540
gtgttgatcg atacattgca gtctgccacc ctgtcaaggc cttagatttc cgtactcccc     600
gaaatgccaa aattatcaat gtctgcaact ggatcctctc ttcagccatt ggtcttcctg     660
taatgttcat ggctacaaca aaatacaggc aaggttccat agattgtaca ctaacattct     720
ctcatccaac ctggtactgg gaaaacctgc tgaagatctg tgttttcatc ttcgccttca     780
ttatgccagt gctcatcatt accgtgtgct atggactgat gatcttgcgc tcaagagtg     840
tccgcatgct ctctggctcc aaagaaaagg acaggaatct tcgaaggatc accaggatgg     900
tgctggtggt ggtggctgtg ttcatcgtct gctggactcc cattcacatt tacgtcatca     960
ttaaagcctt ggttacaatc ccagaaacta cgttccagac tgtttcttgg cacttctgca    1020
ttgctctagg ttacacaaac agctgcctca acccagtcct ttatgcattt ctggatgaaa    1080
```
acttcaaacg atgcttcaga gagttctgta tcccaacctc ttccaacatt gagcaacaaa 1140
actccactcg aattcgtcag aacactagag accaccctc cacggccaat acagtggata 1200
gaactaatca tcagagctga ctatgacatg aaccctaaaa ttcctgttcc c 1251

<210> SEQ ID NO 57
<211> LENGTH: 389
<212> TYPE: PRT
<213> ORGANISM: Homo sapiens

<400> SEQUENCE: 57

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Val Phe Asn Leu
                100                 105                 110

Ala Leu Ala Asp Ala Leu Ala Thr Ser Thr Leu Pro Phe Gln Ser Val
            115                 120                 125

Asn Tyr Leu Met Gly Thr Trp Pro Phe Gly Thr Ile Leu Cys Lys Ile
        130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
                260                 265                 270

Lys Asp Arg Asn Leu Arg Arg Ile Thr Arg Met Val Leu Val Val Val
            275                 280                 285

Ala Val Phe Ile Val Cys Trp Thr Pro Ile His Ile Tyr Val Ile Ile
        290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
                340                 345                 350

```
Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
    370                 375                 380

Thr Asn His Gln Ser
385

<210> SEQ ID NO 58
<211> LENGTH: 1402
<212> TYPE: DNA
<213> ORGANISM: Homo sapiens

<400> SEQUENCE: 58
cggtgctcct ggctacctcg cacagcggtg cccgcccggc cgtcagtacc atggacagca    60
gcgctgcccc cacgaacgcc agcaattgca ctgatgcctt ggcgtactca agttgctccc   120
cagcacccag ccccggttcc tgggtcaact tgtcccactt agatggcaac ctgtccgacc   180
catgcggtcc gaaccgcacc gacctgggcg ggagagacag cctgtgccct ccgaccggca   240
gtccctccat gatcacggcc atcacgatca tggccctcta ctccatcgtg tgcgtggtgg   300
ggctcttcgg aaacttcctg gtcatgtatg tgattgtcag atacaccaag atgaagactg   360
ccaccaacat ctacatttc aaccttgctc tggcagatgc cttagccacc agtaccctgc   420
ccttccagag tgtgaattac ctaatgggaa catggccatt ggaaccatc ctttgcaaga   480 tagtgatctc catagattac tataacatgt tcaccagcat attcaccctc tgcaccatga   540
gtgttgatcg atacattgca gtctgccacc ctgtcaaggc cttagatttc cgtactcccc   600
gaaatgccaa aattatcaat gtctgcaact ggatcctctc ttcagccatt ggtcttcctg   660
taatgttcat ggctacaaca aaatacaggc aaggttccat agattgtaca ctaacattct   720
ctcatccaac ctggtactgg gaaaacctgc tgaagatctg tgttttcatc ttcgccttca   780
ttatgccagt gctcatcatt accgtgtgct atggactgat gatcttgcgc tcaagagtg   840 tccgcatgct ctctggctcc aaagaaaagg acaggaatct tcgaaggatc accaggatgg   900
tgctggtggt ggtggctgtg ttcatcgtct gctggactcc cattcacatt tacgtcatca   960
ttaaagcctt ggttacaatc ccagaaacta cgttccagac tgtttcttgg cacttctgca  1020
ttgctctagg ttacacaaac agctgcctca acccagtcct ttatgcattt ctggatgaaa  1080
acttcaaacg atgcttcaga gagttctgta tcccaacctc ttccaacatt gagcaacaaa  1140
actccactcg aattcgtcag aacactagag accacccctc cacggccaat acagtggata  1200
gaactaatca tcaggtggaa ttgaacctgg actgtcactg tgaaaatgca aagccttggc  1260
cactgagcta caatgcaggg tagtctccat ttcccttccc aggaagagtc tagagcgtta  1320
attttgagtt tgcgaaggct tgtaactatt tcatatgatt tttagagctg actatgacat  1380
gaaccctaaa attcctgttc cc                                            1402

<210> SEQ ID NO 59
<211> LENGTH: 410
<212> TYPE: PRT
<213> ORGANISM: Homo sapiens

<400> SEQUENCE: 59

Met Asp Ser Ser Ala Ala Pro Thr Asn Ala Ser Asn Cys Thr Asp Ala
  1               5                  10                  15

Leu Ala Tyr Ser Ser Cys Ser Pro Ala Pro Ser Pro Gly Ser Trp Val
             20                  25                  30
```

```
Asn Leu Ser His Leu Asp Gly Asn Leu Ser Asp Pro Cys Gly Pro Asn
             35                  40                  45

Arg Thr Asp Leu Gly Gly Arg Asp Ser Leu Cys Pro Pro Thr Gly Ser
 50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
    355                 360                 365

Arg Gln Asn Thr Arg Asp His Pro Ser Thr Ala Asn Thr Val Asp Arg
    370                 375                 380

Thr Asn His Gln Val Glu Leu Asn Leu Asp Cys His Cys Glu Asn Ala
385                 390                 395                 400

Lys Pro Trp Pro Leu Ser Tyr Asn Ala Gly
                405                 410

<210> SEQ ID NO 60
<211> LENGTH: 2601
<212> TYPE: DNA
<213> ORGANISM: Homo sapiens
```

-continued

```
<400> SEQUENCE: 60
cggtgctcct ggctacctcg cacagcggtg cccgcccggc cgtcagtacc atggacagca      60
gcgctgcccc cacgaacgcc agcaattgca ctgatgcctt ggcgtactca agttgctccc     120
cagcacccag ccccggttcc tgggtcaact tgtcccactt agatggcaac ctgtccgacc     180
catgcggtcc gaaccgcacc gacctgggcg gagagacag cctgtgccct ccgaccggca      240
gtccctccat gatcacggcc atcacgatca tggccctcta ctccatcgtg tgcgtggtgg     300
ggctcttcgg aaacttcctg gtcatgtatg tgattgtcag atacaccaag atgaagactg     360
ccaccaacat ctacatttc aaccttgctc tggcagatgc cttagccacc agtaccctgc      420
ccttccagag tgtgaattac ctaatgggaa catggccatt tggaaccatc ctttgcaaga     480
tagtgatctc catagattac tataacatgt tcaccagcat attcacccctc tgcaccatga    540
gtgttgatcg atacattgca gtctgccacc ctgtcaaggc cttagatttc cgtactcccc     600
gaaatgccaa aattatcaat gtctgcaact ggatcctctc ttcagccatt ggtcttcctg     660
taatgttcat ggctacaaca aaatacaggc aaggttccat agattgtaca ctaacattct     720
ctcatccaac ctggtactgg gaaaacctgc tgaagatctg tgttttcatc ttcgccttca     780
ttatgccagt gctcatcatt accgtgtgct atggactgat gatcttgcgc ctcaagagtg     840
tccgcatgct ctctggctcc aaagaaaagg acaggaatct tcgaaggatc caggatgg      900
tgctggtggt ggtggctgtg ttcatcgtct gctggactcc cattcacatt tacgtcatca    960
ttaaagcctt ggttacaatc ccagaaacta cgttccagac tgtttcttgg cacttctgca   1020
ttgctctagg ttacacaaac agctgcctca acccagtcct ttatgcattt ctggatgaaa   1080
acttcaaacg atgcttcaga gagttctgta tcccaacctc ttccaacatt gagcaacaaa   1140
actccactcg aattcgtcag aacactagag accacccctc cacggccaat acagtggata   1200
gaactaatca tcagatcaga gatccaatat caaaccttcc cagggtgtct gtattctgac   1260
aactgtccac tgaggcaatt tccatacagc gcaaagtgga gtggcgattt ggcagttatc   1320
aagggacctc cagccaagtt tgttgctgac caacttgccg ggtcgtcttg aaaaggggc    1380
ttacaggtgt tccaagcccg tgtttatcc tgaagtatcc ctcaacacag aaaaacgacc    1440
tcataacaca aaatacacca gcttaaaaat agcctttgaa ttattttca cattaatcaa     1500
aactttacag aggagataaa cactgatttt ttatttatt ttattttatt ttattttatt    1560
ttattgccat tcattcaacc gtttgcacag agagaaagaa gacagaaatc tgactggtaa   1620
gaaattgtta ccctttgcc agcatgccag gcttctgggt tccctttccc tgagcggccc    1680
tagtgatccg gcttgcggca ccatcgccta cgggccaagc tgcatcataa aggaaatttt   1740
ttttttttca ttctggccag agcaaaacac atgtgataaa acataggcat tagctactct   1800
gcttagcacc aaatatcaga ctagcttaaa tttgccccca gatgggttcc atcatcttta   1860
atccgacctc tgacttgcag ttttcaccac gtgctctctg gcaaaacagt tgccctgagt   1920
aacagaaaag ataggaaagg aaaaggagag agagaaaaac gtgccagtgg aaggggtggg   1980
gaaggtgaaa tgatcaagga ggccagagaa agactcacct attgcagcaa cactgtagaa   2040
gttcaggcag ctgcttctcg gtagcaaaag gatcttttcc ggcaatccta ttagctctca   2100
agtttcccct tttagggagg aaaaagctcc ccatgtcccg cgatcctgta catgtccaac   2160
cctgccatcc acagccatca gcaaagagtg caagacagat taatccaaag agaatagcaa   2220
ttaatatccc atagcatcaa agctgttctt agccaagagg gactttaacg agagggtct    2280
ctaacaccct aaatcttaga agagacccta accatcctaa gtagggcctc taaccccgct   2340
```

-continued

```
ttataaactt ttaattgact cccatcttaa cagttgcaat ccatggagga atgcttgata    2400
acctcggtga taagataaaa aaccaagcat actagaagtg ttctctaaaa ttaaaaatac    2460
agtagttgct agagaaaaat tttagtccaa aaatccaact atagaaacat agaatgtgag    2520
aggtagcaca taagaaataa gtcatgggga tttta tttca tggaccagca atatgatgat    2580
aaaagccatc taaccaaggg c                                              2601
```

<210> SEQ ID NO 61
<211> LENGTH: 402
<212> TYPE: PRT
<213> ORGANISM: Homo sapiens

<400> SEQUENCE: 61

```
Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320
```

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
        370                 375                 380

Thr Asn His Gln Ile Arg Asp Pro Ile Ser Asn Leu Pro Arg Val Ser
385                 390                 395                 400

Val Phe

<210> SEQ ID NO 62
<211> LENGTH: 400
<212> TYPE: PRT
<213> ORGANISM: Homo sapiens

<400> SEQUENCE: 62

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
            85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
            165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

```
Ala Val Phe Ile Val Cys Trp Thr Pro Ile His Ile Tyr Val Ile Ile
            290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
                340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
            370                 375                 380

Thr Asn His Gln Leu Glu Asn Leu Glu Ala Gly Thr Ala Pro Leu Pro
385                 390                 395                 400

<210> SEQ ID NO 63
<211> LENGTH: 392
<212> TYPE: PRT
<213> ORGANISM: Homo sapiens

<400> SEQUENCE: 63

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270
```

```
Lys Asp Arg Asn Leu Arg Arg Ile Thr Arg Met Val Leu Val Val Val
            275                 280                 285

Ala Val Phe Ile Val Cys Trp Thr Pro Ile His Ile Tyr Val Ile Ile
        290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
        370                 375                 380

Thr Asn His Gln Val Arg Ser Leu
385                 390

<210> SEQ ID NO 64
<211> LENGTH: 418
<212> TYPE: PRT
<213> ORGANISM: Homo sapiens

<400> SEQUENCE: 64

Met Asp Ser Ser Ala Ala Pro Thr Asn Ala Ser Asn Cys Thr Asp Ala
  1               5                  10                  15

Leu Ala Tyr Ser Ser Cys Ser Pro Ala Pro Ser Pro Gly Ser Trp Val
             20                  25                  30

Asn Leu Ser His Leu Asp Gly Asn Leu Ser Asp Pro Cys Gly Pro Asn
         35                  40                  45

Arg Thr Asp Leu Gly Gly Arg Asp Ser Leu Cys Pro Pro Thr Gly Ser
     50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
```

-continued

```
                    245                 250                 255
Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
                275                 280                 285

Ala Val Phe Ile Val Cys Trp Thr Pro Ile His Ile Tyr Val Ile Ile
            290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
                355                 360                 365

Arg Gln Asn Thr Arg Asp His Pro Ser Thr Ala Asn Thr Val Asp Arg
            370                 375                 380

Thr Asn His Gln Pro Pro Leu Ala Val Ser Met Ala Gln Ile Phe Thr
385                 390                 395                 400

Arg Tyr Pro Pro Pro Thr His Arg Glu Lys Thr Cys Asn Asp Tyr Met
                    405                 410                 415

Lys Arg

<210> SEQ ID NO 65
<211> LENGTH: 446
<212> TYPE: PRT
<213> ORGANISM: Homo sapiens

<400> SEQUENCE: 65

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
65              70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145             150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
```

-continued

```
                195                 200                 205
Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Cys Leu Pro Ile Pro Ser Leu Ser Cys Trp Ala Leu
385                 390                 395                 400

Glu His Gly Cys Leu Val Val Tyr Pro Gly Pro Leu Gln Gly Pro Leu
                405                 410                 415

Val Arg Tyr Asp Leu Pro Ala Ile Leu His Ser Ser Cys Leu Arg Gly
            420                 425                 430

Asn Thr Ala Pro Ser Pro Ser Gly Gly Ala Phe Leu Leu Ser
        435                 440                 445

<210> SEQ ID NO 66
<211> LENGTH: 388
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 66

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
                20                  25                  30

Asn Leu Ser His Leu Asp Gly Asn Leu Ser Asp Pro Cys Gly Pro Asn
            35                  40                  45

Arg Thr Asp Leu Gly Gly Arg Asp Ser Leu Cys Pro Pro Thr Gly Ser
        50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110
```

-continued

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
            165                 170                 175

Ala Leu Asp Phe Arg Thr Pro Arg Asn Ala Lys Ile Ile Asn Val Cys
        180                 185                 190

Asn Trp Ile Leu Ser Ser Ala Ile Gly Leu Pro Val Met Phe Met Ala
    195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
        260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
        340                 345                 350

Cys Ile Pro Thr Ser Ser Asn Ile Glu Gln Gln Asn Ser Thr Arg Ile
    355                 360                 365

Arg Gln Asn Thr Arg Asp His Pro Ser Thr Ala Asn Thr Val Asp Arg
    370                 375                 380

Thr Asn His Gln
385

<210> SEQ ID NO 67
<211> LENGTH: 7
<212> TYPE: PRT
<213> ORGANISM: Rattus norvegicus

<400> SEQUENCE: 67

Asn His Gln Val Cys Ala Phe
 1               5

<210> SEQ ID NO 68
<211> LENGTH: 111
<212> TYPE: DNA
<213> ORGANISM: Rattus norvegicus
<220> FEATURE:
<221> NAME/KEY: CDS
<222> LOCATION: (1)..(21)

<400> SEQUENCE: 68 aac cac cag gta tgt gct ttc tagaattacg gataacatat aaaaatacca      51
Asn His Gln Val Cys Ala Phe
 1               5

-continued

```
tatctggtac cagtctaaga tttaaatctt taagaaggtc agtaacttga ggcaaagtcc        111
```

<210> SEQ ID NO 69
<211> LENGTH: 246
<212> TYPE: DNA
<213> ORGANISM: Rattus norvegicus
<220> FEATURE:
<221> NAME/KEY: CDS
<222> LOCATION: (1)..(204)

<400> SEQUENCE: 69

```
aac cac cag cca gcc ctg gca gtc agc gtg gcc cag atc ttt aca gga         48
Asn His Gln Pro Ala Leu Ala Val Ser Val Ala Gln Ile Phe Thr Gly
  1               5                  10                  15 tat cct tct ccg act cat ggt gaa aaa ccc tgc aag agt tac agg gac         96
Tyr Pro Ser Pro Thr His Gly Glu Lys Pro Cys Lys Ser Tyr Arg Asp
             20                  25                  30 aga cct aga ccc tgt gga aga acg tgg tct ttg aaa tcg cgt gca gaa        144
Arg Pro Arg Pro Cys Gly Arg Thr Trp Ser Leu Lys Ser Arg Ala Glu
         35                  40                  45 tcc aat gtg gag cac ttc cat tgt gga gcc gca tta atc tat aac aat        192
Ser Asn Val Glu His Phe His Cys Gly Ala Ala Leu Ile Tyr Asn Asn
     50                  55                  60 gtg aat ttc atc taaacacagg gatgtgctag tgagaagttt ggaggtgcag gc         246
Val Asn Phe Ile
 65
```

<210> SEQ ID NO 70
<211> LENGTH: 68
<212> TYPE: PRT
<213> ORGANISM: Rattus norvegicus

<400> SEQUENCE: 70

```
Asn His Gln Pro Ala Leu Ala Val Ser Val Ala Gln Ile Phe Thr Gly
  1               5                  10                  15

Tyr Pro Ser Pro Thr His Gly Glu Lys Pro Cys Lys Ser Tyr Arg Asp
             20                  25                  30

Arg Pro Arg Pro Cys Gly Arg Thr Trp Ser Leu Lys Ser Arg Ala Glu
         35                  40                  45

Ser Asn Val Glu His Phe His Cys Gly Ala Ala Leu Ile Tyr Asn Asn
     50                  55                  60

Val Asn Phe Ile
 65
```

<210> SEQ ID NO 71
<211> LENGTH: 293
<212> TYPE: DNA
<213> ORGANISM: Rattus norvegicus
<220> FEATURE:
<221> NAME/KEY: CDS
<222> LOCATION: (1)..(255)

<400> SEQUENCE: 71

```
aac cac cag cca gcc ctg gca gtc agc gtg gcc cag atc ttt aca gga         48
Asn His Gln Pro Ala Leu Ala Val Ser Val Ala Gln Ile Phe Thr Gly
  1               5                  10                  15 tat cct tct ccg act cat ggt gaa aaa ccc tgc aag agt tac agg gac         96
Tyr Pro Ser Pro Thr His Gly Glu Lys Pro Cys Lys Ser Tyr Arg Asp
             20                  25                  30 aga cct aga ccc tgt gga aga acg tgg tct ttg aaa tcg cgt gca gaa        144
Arg Pro Arg Pro Cys Gly Arg Thr Trp Ser Leu Lys Ser Arg Ala Glu
         35                  40                  45
```

```
tcc aat gtg gag cac ttc cat tgt gga gcc gca tta atc tat aac aat    192
Ser Asn Val Glu His Phe His Cys Gly Ala Ala Leu Ile Tyr Asn Asn
    50                  55                  60 gaa cta aaa ata ggg cca gtg tcc tgg ctc cag atg cct gcg cac gtg    240
Glu Leu Lys Ile Gly Pro Val Ser Trp Leu Gln Met Pro Ala His Val
65                  70                  75                  80 ctc gtg cgc ccc tgg taatgaacac gggctccgat tctgaatatc cttctgtg     293
Leu Val Arg Pro Trp
                85
```

<210> SEQ ID NO 72
<211> LENGTH: 85
<212> TYPE: PRT
<213> ORGANISM: Rattus norvegicus

<400> SEQUENCE: 72

```
Asn His Gln Pro Ala Leu Ala Val Ser Val Ala Gln Ile Phe Thr Gly
1               5                   10                  15

Tyr Pro Ser Pro Thr His Gly Glu Lys Pro Cys Lys Ser Tyr Arg Asp
                20                  25                  30

Arg Pro Arg Pro Cys Gly Arg Thr Trp Ser Leu Lys Ser Arg Ala Glu
            35                  40                  45

Ser Asn Val Glu His Phe His Cys Gly Ala Ala Leu Ile Tyr Asn Asn
    50                  55                  60

Glu Leu Lys Ile Gly Pro Val Ser Trp Leu Gln Met Pro Ala His Val
65                  70                  75                  80

Leu Val Arg Pro Trp
                85
```

<210> SEQ ID NO 73
<211> LENGTH: 4
<212> TYPE: PRT
<213> ORGANISM: Rattus norvegicus

<400> SEQUENCE: 73

```
Asn His Gln Thr
  1
```

<210> SEQ ID NO 74
<211> LENGTH: 204
<212> TYPE: DNA
<213> ORGANISM: Rattus norvegicus
<220> FEATURE:
<221> NAME/KEY: CDS
<222> LOCATION: (1)..(12)

<400> SEQUENCE: 74

```
aac cac cag acc tagaccctgt ggaagaacgt ggtctttgaa atcgcgtgca        52
Asn His Gln Thr
  1 gaatccaatg tggagcactt ccattgtgga gccgcattaa tctataacaa tgaactaaaa   112 atagggccag tgtcctggct ccagatgcct gcgcacgtgc tcgtgcgccc tggtaatga   172 acacgggctc cgattctgaa tatccttctg tg                                204
```

<210> SEQ ID NO 75
<211> LENGTH: 10
<212> TYPE: PRT
<213> ORGANISM: Rattus norvegicus

<400> SEQUENCE: 75

Asn His Gln Glu Pro Gln Ser Val Glu Thr
 1               5                  10

<210> SEQ ID NO 76
<211> LENGTH: 438
<212> TYPE: DNA
<213> ORGANISM: Rattus norvegicus
<220> FEATURE:
<221> NAME/KEY: CDS
<222> LOCATION: (1)..(30)

<400> SEQUENCE: 76 aac cac cag gag cct cag tca gta gag aca tgatgtgaat gaaccaactg      50
Asn His Gln Glu Pro Gln Ser Val Glu Thr
 1               5                  10 attaaacaag gttttctgaa cactgaaata caacacaaat gtagaggtta ctagagaaaa   110
tttgtagcct gaaaattcaa ttacggaaac caaatgagtg tgagtgtata cattttaagg   170
cctcagagag attttatttc atgactaaca acatgaccca agcacctaa actgtggtga    230 ttagattaca aagacaattc tagagcctgg gactaaagaa atgttagccc tcacacagac   290
aggcctcaca cttcagtaat ggaatgagca aattagatta gtgagaaaga tggaggaaag   350
actcgaaata ttttcatatc ttcctgtgga actccacaag aaaaccaata gaataaacca   410
acctgctgga cccttggtgg ctcttacc                                      438

<210> SEQ ID NO 77
<211> LENGTH: 7
<212> TYPE: PRT
<213> ORGANISM: Rattus norvegicus

<400> SEQUENCE: 77

Asn His Gln Gly Ala Glu Leu
 1               5

<210> SEQ ID NO 78
<211> LENGTH: 891
<212> TYPE: DNA
<213> ORGANISM: Rattus norvegicus
<220> FEATURE:
<221> NAME/KEY: CDS
<222> LOCATION: (1)..(21)

<400> SEQUENCE: 78 aac cac cag gga gca gag tta tgaggattaa tacaaaaga ctaccacgtc         51
Asn His Gln Gly Ala Glu Leu
 1               5 cttcagagga gcagccagag ggaggccctt ggcccccaca atggtaggtg ctcccacttg   111
ctgtctcccc atcacacatc tctcactgtt ccctttgttt tcagctatgg ctacccggca   171
tagcctttat tcagtctttc tgactgacct cagatttatg caatacaacc tagatggatc   231
cgcctcagga gacaggaatg ctcataccga agtgggaagt gtggctaatg caatacacgt   291
gagccaacac ccccagagag catggtggta atggcggcag agtcatcccc cactcaaagg   351
caattattaa caaatttatc tccctgcttc cagctcagaa atcagagcca gacagaaatg   411
ggtttctctg ttgccttctc tctctctctc tctctctctc tctctctctc tctctctctc   471
tcattgttat ccacatcaac acataaccct tttactttt ctaagcagcc ctcttttag    531 gggttttcaa actctcgcct gcactttgaa agggtaagga tttaaattga tttttttttc   591
ttctttctcc aacccaggga taacattcta gagcaagcaa tttgaaacta tctatacaaa   651
ctgagcttca aatctttggc atttaaatat tttgctttca ttggagaaaa ggaagagcat   711

```
aggaaagctt gggctcttcc tccctccct aggtgtcctg ctttgtcttc cctcccaggc    771
ttgtaggggt gtggctgctt ggtagcttcc tctaggacac tgttgggcct tcttatcctg    831
cctgacccac ctgaccttcc tctaatggtc aacctctcta ttccagcaca ttcctgtttc    891
```

<210> SEQ ID NO 79
<211> LENGTH: 1628
<212> TYPE: DNA
<213> ORGANISM: Rattus norvegicus

<400> SEQUENCE: 79

```
gttacagcct acctagtccg cagcaggcct tcagcaccat ggacagcagc accggcccag     60
ggaacaccag cgactgctca gacccctag ctcaggcaag ttgctcccca gcacctggct    120
cctggctcaa cttgtcccac gttgatggca accagtccga tccatgcggt ctgaaccgca    180
ccgggcttgg cgggaacgac agcctgtgcc ctcagaccgg cagcccttcc atggtcacag    240
ccattaccat catggccctc tactctatcg tgtgtgtagt gggcctcttc ggaaacttcc    300
tggtcatgta tgtgattgta agatacacca aaatgaagac tgccaccaac atctacattt    360
tcaaccttgc tctggcagac gccttagcga ccagtacact gcccttcag agtgtcaact    420 acctgatggg aacatggccc ttcggaacca tcctctgcaa gatcgtgatt tcaatagatt    480
actacaacat gttcaccagc atattcaccc tctgcaccat gagcgtggac cgctacattg    540
ctgtctgcca cccagtcaaa gccctggatt ccgtacccc cgaaatgcc aaaatcgtca    600 acgtctgcaa ctggatcctc tcttctgcca tcggtctgcc tgtaatgttc atggcaacca    660
caaaatacag gcaggggtcc atagattgca ccctcacgtt ctcccaccca acctggtact    720
gggagaacct gctcaaaatc tgtgtcttta tcttcgcttt catcatgccg gtcctcatca    780
tcactgtgtg ttacggcctg atgatcttac gactcaagag cgttcgcatg ctatcgggct    840
ccaaagaaaa ggacaggaat ttgcgcagga tcacccggat ggtgctggtg gtcgtggctg    900
tatttatcgt ctgctggacc cccatccaca tctacgtcat catcaaagcg ctgatcacga    960
ttccagaaac cacatttcag accgtttcct ggcacttctg cattgctttg ggttacacga   1020
acagctgcct gaatccagtt cttttacgcc ttcctgggat gaaaacttca agcgatgctt   1080
cagaagagtt ctgcatccca acctcgtcca cgatcgaaca gcaaaactcc actcgagtcc   1140
gtcagaacac tagggaacat ccctccacgg ctaatacagt ggatcgaact aaccaccagg   1200
agcctcagtc agtagagaca tgatgtgaat gaaccaactg attaaacaag gttttctgaa   1260
cactgaaata caacacaaat gtagaggtta ctagagaaaa tttgtagcct gaaaattcaa   1320
ttacggaaac caaatgagtg tgagtgtata cattttaagg cctcagagag attttatttc   1380
atgactaaca acatgaccca agcacctaa actgtggtga ttagattaca aagacaattc    1440
tagagcctgg gactaaagaa atgttagccc tcacacagac aggcctcaca cttcagtaat   1500
ggaatgagca aattagatta gtgagaaaga tggaggaaag actcgaaata ttttcatatc   1560
ttcctgtgga actccacaag aaaaccaata gaataaacca acctgctgga cccttggtgg   1620
ctcttacc                                                              1628
```

<210> SEQ ID NO 80
<211> LENGTH: 394
<212> TYPE: PRT
<213> ORGANISM: Rattus norvegicus

<400> SEQUENCE: 80

-continued

```
Met Asp Ser Ser Thr Gly Pro Gly Asn Thr Ser Asp Cys Ser Asp Pro
 1               5                  10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Gly Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
 65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
        130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
        290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Leu
                325                 330                 335

Arg Leu Pro Gly Met Lys Thr Ser Ser Asp Ala Ser Glu Glu Phe Cys
                340                 345                 350

Ile Pro Thr Ser Ser Thr Ile Glu Gln Gln Asn Ser Thr Arg Val Arg
            355                 360                 365

Gln Asn Thr Arg Glu His Pro Ser Thr Ala Asn Thr Val Asp Arg Thr
        370                 375                 380

Asn His Gln Glu Pro Gln Ser Val Glu Thr
385                 390
```

<210> SEQ ID NO 81
<211> LENGTH: 1433
<212> TYPE: DNA

<213> ORGANISM: Rattus norvegicus

<400> SEQUENCE: 81

```
gttacagcct acctagtccg cagcaggcct tcagcaccat ggacagcagc accggcccag      60
ggaacaccag cgactgctca gacccttag ctcaggcaag ttgctcccca gcacctggct     120
cctggctcaa cttgtcccac gttgatggca accagtccga tccatgcggt ctgaaccgca     180
ccgggcttgg cgggaacgac agcctgtgcc ctcagaccgg cagcccttcc atggtcacag     240
ccattaccat catggccctc tactctatcg tgtgtgtagt gggcctcttc ggaaacttcc     300
tggtcatgta tgtgattgta agatacacca aaatgaagac tgccaccaac atctacattt     360
tcaaccttgc tctggcagac gccttagcga ccagtacact gcccttcag agtgtcaact      420
acctgatggg aacatggccc ttcggaacca tcctctgcaa gatcgtgatc tcaatagatt     480
actacaacat gttcaccagc atattcaccc tctgcaccat gagcgtggac cgctacattg     540
ctgtctgcca cccagtcaaa gccctggatt ccgtacccc ccgaaatgcc aaaatcgtca      600
acgtctgcaa ctggatcctc tcttctgcca tcggtctgcc tgtaatgttc atggcaacca     660
caaatacag gcaggggtcc atagattgca ccctcacgtt ctcccaccca acctggtact      720
gggagaacct gctcaaaatc tgtgtcttta tcttcgcttt catcatgccg gtcctcatca     780
tcactgtgtg ttacggcctg atgatcttac gactcaagag cgttcgcatg ctatcgggct     840
ccaaagaaaa ggacaggaat ctgcgcagga tcacccggat ggtgctggtg gtcgtggctg     900
tatttatcgt ctgctggacc cccatccaca tctacgtcat catcaaagcg ctgatcacga     960
ttccagaaac cacatttcag accgtttcct ggcacttctg cattgctttg ggttacacga    1020
acagctgcct gaatccagtt ctttacgcct tcctggatga aaacttcaag cgatgcttca    1080
gagagttctg catcccaacc tcgtccacga tcgaacagca aaactccact cgagtccgtc    1140
agaacactag ggaacatccc tccacggcta atacagtgga tcgaactaac caccagccag    1200
ccctggcagt cagcgtggcc cagatcttta caggatatcc ttctccgact catggtgaaa    1260
aaccctgcaa gagttacagg gacagaccta gaccctgtgg aagaacgtgg tcttttgaaat   1320
cgcgtgcaga atccaatgtg gagcacttcc attgtggagc cgcattaatc tataacaatg    1380
tgaatttcat ctaaacacag ggatgtgcta gtgagaagtt tggaggtgca ggc            1433
```

<210> SEQ ID NO 82
<211> LENGTH: 451
<212> TYPE: PRT
<213> ORGANISM: Rattus norvegicus

<400> SEQUENCE: 82

```
Met Asp Ser Ser Thr Gly Pro Gly Asn Thr Ser Asp Cys Ser Asp Pro
  1               5                  10                  15

Leu Ala Gln Ala Ser Cys Ser Pro Ala Pro Gly Ser Trp Leu Asn Leu
                 20                  25                  30

Ser His Val Asp Gly Asn Gln Ser Asp Pro Cys Gly Leu Asn Arg Thr
             35                  40                  45

Gly Leu Gly Gly Asn Asp Ser Leu Cys Pro Gln Thr Gly Ser Pro Ser
         50                  55                  60

Met Val Thr Ala Ile Thr Ile Met Ala Leu Tyr Ser Ile Val Cys Val
 65                  70                  75                  80

Val Gly Leu Phe Gly Asn Phe Leu Val Met Tyr Val Ile Val Arg Tyr
                 85                  90                  95

Thr Lys Met Lys Thr Ala Thr Asn Ile Tyr Ile Phe Asn Leu Ala Leu
```

|       |       |       |       |       |       | 100   |       |       |       |       | 105   |       |       |       |       | 110   |       |       |
|-------|-------|-------|-------|-------|-------|-------|-------|-------|-------|-------|-------|-------|-------|-------|-------|-------|-------|-------|

Ala Asp Ala Leu Ala Thr Ser Thr Leu Pro Phe Gln Ser Val Asn Tyr
              115                 120                 125

Leu Met Gly Thr Trp Pro Phe Gly Thr Ile Leu Cys Lys Ile Val Ile
        130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
    370                 375                 380

His Gln Pro Ala Leu Ala Val Ser Val Ala Gln Ile Phe Thr Gly Tyr
385                 390                 395                 400

Pro Ser Pro Thr His Gly Glu Lys Pro Cys Lys Ser Tyr Arg Asp Arg
                405                 410                 415

Pro Arg Pro Cys Gly Arg Thr Trp Ser Leu Lys Ser Arg Ala Glu Ser
            420                 425                 430

Asn Val Glu His Phe His Cys Gly Ala Ala Leu Ile Tyr Asn Asn Val
        435                 440                 445

Asn Phe Ile
    450

<210> SEQ ID NO 83
<211> LENGTH: 1480
<212> TYPE: DNA
<213> ORGANISM: Rattus norvegicus

<400> SEQUENCE: 83
gttacagcct acctagtccg cagcaggcct tcagcaccat ggacagcagc accggcccag    60
ggaacaccag cgactgctca gacccctag ctcaggcaag ttgctcccca gcacctggct    120

```
cctggctcaa cttgtcccac gttgatggca accagtccga tccatgcggt ctgaaccgca    180
ccgggcttgg cgggaacgac agcctgtgcc ctcagaccgg cagcccttcc atggtcacag    240
ccattaccat catggccctc tactctatcg tgtgtgtagt gggcctcttc ggaaacttcc    300
tggtcatgta tgtgattgta agatacacca aaatgaagac tgccaccaac atctacattt    360
tcaaccttgc tctggcagac gccttagcga ccagtacact gcccttcag agtgtcaact     420
acctgatggg aacatggccc ttcggaacca tcctctgcaa gatcgtgatc tcaatagatt    480
actacaacat gttcaccagc atattcaccc tctgcaccat gagcgtggac cgctacattg    540
ctgtctgcca cccagtcaaa gccctggatt ccgtacccc ccgaaatgcc aaaatcgtca     600
acgtctgcaa ctggatcctc tcttctgcca tcggtctgcc tgtaatgttc atggcaacca    660
caaaatacag gcagggtcc atagattgca ccctcacgtt ctcccaccca acctggtact     720
gggagaacct gctcaaaatc tgtgtcttta tcttcgcttt catcatgccg gtcctcatca    780
tcactgtgtg ttacggcctg atgatcttac gactcaagag cgttcgcatg ctatcgggct    840
ccaaagaaaa ggacaggaat ctgcgcagga tcacccggat ggtgctggtg gtcgtggctg    900
tatttatcgt ctgctggacc cccatccaca tctacgtcat catcaaagcg ctgatcacga    960
ttccagaaac cacatttcag accgtttcct ggcacttctg cattgctttg ggttacacga   1020
acagctgcct gaatccagtt ctttacgcct tcctggatga aaacttcaag cgatgcttca   1080
gagagttctg catcccaacc tcgtccacga tcgaacagca aaactccact cgagtccgtc   1140
agaacactag ggaacatccc tccacggcta atacagtgga tcgaactaac caccagccag   1200
ccctggcagt cagcgtggcc cagatcttta caggatatcc ttctccgact catggtgaaa   1260
aaccctgcaa gagttacagg gacagaccta gaccctgtgg aagaacgtgg tctttgaaat   1320
cgcgtgcaga atccaatgtg gagcacttcc attgtggagc cgcattaatc tataacaatg   1380
aactaaaaat agggccagtg tcctggctcc agatgcctgc gcacgtgctc gtgcgccct    1440
ggtaatgaac acgggctccg attctgaata tccttctgtg                         1480
```

<210> SEQ ID NO 84
<211> LENGTH: 468
<212> TYPE: PRT
<213> ORGANISM: Rattus norvegicus

<400> SEQUENCE: 84

```
Met Asp Ser Ser Thr Gly Pro Gly Asn Thr Ser Asp Cys Ser Asp Pro
  1               5                  10                  15

Leu Ala Gln Ala Ser Cys Ser Pro Ala Pro Gly Ser Trp Leu Asn Leu
             20                  25                  30

Ser His Val Asp Gly Asn Gln Ser Asp Pro Cys Gly Leu Asn Arg Thr
         35                  40                  45

Gly Leu Gly Gly Asn Asp Ser Leu Cys Pro Gln Thr Gly Ser Pro Ser
     50                  55                  60

Met Val Thr Ala Ile Thr Ile Met Ala Leu Tyr Ser Ile Val Cys Val
 65                  70                  75                  80

Val Gly Leu Phe Gly Asn Phe Leu Val Met Tyr Val Ile Val Arg Tyr
                 85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125
```

```
Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
            275                 280                 285

Phe Ile Val Cys Trp Thr Pro Ile His Ile Tyr Val Ile Ile Lys Ala
            290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Thr Arg Val Arg Gln
            355                 360                 365

Asn Thr Arg Glu His Pro Ser Thr Ala Asn Thr Val Asp Arg Thr Asn
    370                 375                 380

His Gln Pro Ala Leu Ala Val Ser Val Ala Gln Ile Phe Thr Gly Tyr
385                 390                 395                 400

Pro Ser Pro Thr His Gly Glu Lys Pro Cys Lys Ser Tyr Arg Asp Arg
                405                 410                 415

Pro Arg Pro Cys Gly Arg Thr Trp Ser Leu Lys Ser Arg Ala Glu Ser
                420                 425                 430

Asn Val Glu His Phe His Cys Gly Ala Ala Leu Ile Tyr Asn Asn Glu
            435                 440                 445

Leu Lys Ile Gly Pro Val Ser Trp Leu Gln Met Pro Ala His Val Leu
    450                 455                 460

Val Arg Pro Trp
465

<210> SEQ ID NO 85
<211> LENGTH: 1385
<212> TYPE: DNA
<213> ORGANISM: Rattus norvegicus

<400> SEQUENCE: 85
gcctacctag tccgcagcag gccttcagca ccatggacag cagcaccggc ccagggaaca      60
ccagcgactg ctcagacccc ttagctcagg caagttgctc cccagcacct ggctcctggc     120
tcaacttgtc ccacgttgat ggcaaccagt ccgatccatg cggtctgaac cgcaccgggc     180
```

-continued

```
ttggcgggaa cgacagcctg tgccctcaga ccggcagccc ttccatggtc acagccatta      240
ccatcatggc cctctactct atcgtgtgtg tagtgggcct cttcggaaac ttcctggtca      300
tgtatgtgat tgtaagatac accaaaatga agactgccac caacatctac attttcaacc      360
ttgctctggc agacgcctta gcgaccagta cactgccctt tcagagtgtc aactacctga      420
tgggaacatg gccttcgga accatcctct gcaagatcgt gatctcaata gattactaca      480
acatgttcac cagcatattc accctctgca ccatgagcgt ggaccgctac attgctgtct      540
gccacccagt caaagccctg gatttccgta cccccccgaaa tgccaaaatc gtcaacgtct      600
gcaactggat cctctcttct gccatcggtc tgcctgtaat gttcatggca accacaaaat      660
acaggcaggg gtccatagat tgcaccctca cgttctccca cccaacctgg tactgggaga      720
acctgctcaa aatctgtgtc tttgtcttcg ctttcatcat gccggtcctc atcatcactg      780
tgtgttacgg cctgatgatc ttacgactta agagcgttcg catgctatcg ggctccaaag      840
aaaaggacag gaatctgcgc aggatcaccc ggatggtgct ggtggtcgtg gctgtatttta      900 tcgtctgctg gaccccccatc cacatctacg tcatcatcaa agcgctgatc acgattccag      960
aaaccacatt tcagaccgtt tcctggcact tctgcattgc tttgggttac acgaacagct     1020
gcctgaatcc agttctttac gccttcctgg atgaaaactt caagcgatgc ttcagagagt     1080
tctgcatccc aacctcgtcc acgatcgaac agcaaaactc cactcgagtc cgtcagaaca     1140
ctagggaaca tccctccacg gctaatacag tggatcgaac taaccaccag acctagaccc     1200
tgtggaagaa cgtggtcttt gaaatcgcgt gcagaatcca atgtggagca cttccattgt     1260
ggagccgcat taatctataa caatgaacta aaaatagggc cagtgtcctg gctccagatg     1320
cctgcgcacg tgctcgtgcg ccctggtaa tgaacacggg ctccgattct gaatatcctt     1380
ctgtg                                                                 1385
```

<210> SEQ ID NO 86
<211> LENGTH: 387
<212> TYPE: PRT
<213> ORGANISM: Rattus norvegicus

<400> SEQUENCE: 86

```
Met Asp Ser Ser Thr Gly Pro Gly Asn Thr Ser Asp Cys Ser Asp Pro
 1               5                  10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
```

```
                145                 150                 155                 160
Met Ser Val Asp Arg Tyr Ile Ala Val Cys His Pro Val Lys Ala Leu
                    165                 170                 175
Asp Phe Arg Thr Pro Arg Asn Ala Lys Ile Val Asn Val Cys Asn Trp
                180                 185                 190
Ile Leu Ser Ser Ala Ile Gly Leu Pro Val Met Phe Met Ala Thr Thr
            195                 200                 205
Lys Tyr Arg Gln Gly Ser Ile Asp Cys Thr Leu Thr Phe Ser His Pro
        210                 215                 220
Thr Trp Tyr Trp Glu Asn Leu Leu Lys Ile Cys Val Phe Val Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
                260                 265                 270
Arg Asn Leu Arg Arg Ile Thr Arg Met Val Leu Val Val Val Ala Val
                275                 280                 285
Phe Ile Val Cys Trp Thr Pro Ile His Ile Tyr Val Ile Ile Lys Ala
            290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
                340                 345                 350
Pro Thr Ser Ser Thr Ile Glu Gln Gln Asn Ser Thr Arg Val Arg Gln
                355                 360                 365
Asn Thr Arg Glu His Pro Ser Thr Ala Asn Thr Val Asp Arg Thr Asn
            370                 375                 380
His Gln Thr
385

<210> SEQ ID NO 87
<211> LENGTH: 2078
<212> TYPE: DNA
<213> ORGANISM: Rattus norvegicus

<400> SEQUENCE: 87
gttacagcct acctagtccg cagcaggcct tcagcaccat ggacagcagc accggcccag      60
ggaacaccag cgactgctca gaccccttag ctcaggcaag ttgctcccca gcacctggct     120
cctggctcaa cttgtcccac gttgatggca accagtccga tccatgcggt ctgaaccgca     180
ccgggcttgg cgggaacgac agcctgtgcc ctcagaccgg cagcccttcc atggtcacag     240
ccattaccat catgggcctc tactctatcg tgtgtgtagt gggcctcttc ggaaacttcc     300
tggtcatgta tgtgattgta agatacacca aaatgaagac tgccaccaac atctacattt     360
tcaaccttgc tctggcagac gccttagcga ccagtacact gccctttcag agtgtcaact     420
acctgatggg aacatggccc ttcggaacca tcctctgcaa gatcgtgatc tcaatagatt     480
actacaacat gttcaccagc atattcaccc tctgcaccat gagcgtggac cgctacattg     540
ctgtctgcca cccagtcaaa gcctggatt tccgtacccc cgaaatgcc aaaatcgtca     600 acgtctgcaa ctggatcctc tcttctgcca tcggtctgcc tgtaatgttc atggcaacca     660
caaaatacag gcaggggtcc atagattgca ccctcacgtt ctcccaccca acctggtact     720
```

```
gggagaacct gctcaaaatc tgtgtcttta tcttcgcttt catcatgccg gtcctcatca      780
tcactgtgtg ttacggcctg atgatcttac gactcaagag cgttcgcatg ctatcgggct      840
ccaaagaaaa ggacaggaat ctgcgcggga tcacccggat ggtgctggtg gtcgtggctg      900
tatttatcgt ctgctggacc cccatccaca tctacgtcat catcaaagcg ctgatcacga      960
ttccagaaac acatttcag accgtttcct ggcacttctg cattgctttg ggttacacga     1020
acagctgcct gaatccagtt ctttacgcct tcctggatga aaacttcaag cgatgcttca     1080
gagagttctg catcccaacc tcgtccacga tcgaacagca aaactccact cgagtccgtc     1140
agaacactag ggaacatccc tccacggcta atacagtgga tcgaactaac caccagggag     1200
cagagttatg aggattaata caaaaagact accacgtcct tcagaggagc agccagaggg     1260
aggcccttgg cccccacaat ggtaggtgct cccacttgct gtctccccat cacacatctc     1320
tcactgttcc ctttgttttc agctatggct acccggcata gcctttattc agtctttctg     1380
actgacctca gatttatgca atacaaccta gatggatccg cctcaggaga caggaatgct     1440
cataccgaag tgggaagtgt ggctaatgca atacacgtga gccaacaccc ccagagagca     1500
tggtggtaat ggcggcagag tcatccccca ctcaaaggca attattaaca aatttatctc     1560
cctgcttcca gctcagaaat cagagccaga cagaaatggg tttctctgtt gccttctctc     1620
tctctctctc tctctctctc tctctctctc tctctctctc attgttatcc acatcaacac     1680
ataacccttt tactttttct aagcagccct ctttttaggg gttttcaaac tctcgcctgc     1740
actttgaaag ggtaaggatt taaattgatt ttttttttctt ctttctccaa cccagggata     1800
acattctaga gcaagcaatt tgaaactatc tatacaaact gagcttcaaa tctttggcat     1860
ttaaatattt tgctttcatt ggagaaaagg aagagcatag gaaagcttgg gctcttcctc     1920
ccctccctag gtgtcctgct tgtcttccc tcccaggctt gtaggggtgt ggctgcttgg     1980
tagcttcctc taggacactg ttgggccttc ttatcctgcc tgacccacct gaccttcctc     2040
taatggtcaa cctctctatt ccagcacatt cctgtttc                            2078
```

<210> SEQ ID NO 88
<211> LENGTH: 390
<212> TYPE: PRT
<213> ORGANISM: Rattus norvegicus

<400> SEQUENCE: 88

```
Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
```

```
                130             135             140
Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
                180                 185                 190

Ile Leu Ser Ser Ala Ile Gly Leu Pro Val Met Phe Met Ala Thr Thr
                195                 200                 205

Lys Tyr Arg Gln Gly Ser Ile Asp Cys Thr Leu Thr Phe Ser His Pro
210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
                260                 265                 270

Arg Asn Leu Arg Gly Ile Thr Arg Met Val Leu Val Val Val Ala Val
                275                 280                 285

Phe Ile Val Cys Trp Thr Pro Ile His Ile Tyr Val Ile Ile Lys Ala
                290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
                340                 345                 350

Pro Thr Ser Ser Thr Ile Glu Gln Gln Asn Ser Thr Arg Val Arg Gln
                355                 360                 365

Asn Thr Arg Glu His Pro Ser Thr Ala Asn Thr Val Asp Arg Thr Asn
                370                 375                 380

His Gln Gly Ala Glu Leu
385                 390

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 89

Gly Gly Gly Gly Ser Gly Gly Gly Gly Ser Gly Gly Gly Gly Ser
1               5                   10                  15
```